US012748002B2

(12) United States Patent
Ong et al.

(10) Patent No.: US 12,748,002 B2
(45) Date of Patent: Sep. 29, 2026

(54) STRESS AND DISPLACEMENT SENSORS AND METHODS OF SENSING

(71) Applicant: University of Oregon, Eugene, OR (US)

(72) Inventors: Keat Ghee Ong, Eugene, OR (US); Michael McGeehan, Eugene, OR (US)

(73) Assignee: University of Oregon, Eugene, OR (US)

( * ) Notice: Subject to any disclaimer, the term of this patent is extended or adjusted under 35 U.S.C. 154(b) by 308 days.

(21) Appl. No.: 18/286,093

(22) PCT Filed: Apr. 8, 2022

(86) PCT No.: PCT/US2022/024116
§ 371 (c)(1),
(2) Date: Oct. 6, 2023

(87) PCT Pub. No.: WO2022/217120
PCT Pub. Date: Oct. 13, 2022

(65) Prior Publication Data

US 2024/0192066 A1 Jun. 13, 2024

Related U.S. Application Data

(60) Provisional application No. 63/172,615, filed on Apr. 8, 2021.

(51) Int. Cl.

| | |
|---|---|
| ***G01L 1/24*** | (2006.01) |
| ***A61B 5/00*** | (2006.01) |
| ***G01B 11/16*** | (2006.01) |

(52) U.S. Cl.
CPC .............. *G01L 1/24* (2013.01); *A61B 5/0082* (2013.01); *A61B 5/6807* (2013.01);
(Continued)

(58) Field of Classification Search
CPC ....... G01L 1/24; A61B 5/0082; A61B 5/6807; A61B 5/6811; A61B 2562/0266; G01B 11/16
(Continued)

(56) References Cited

U.S. PATENT DOCUMENTS

| | | | | |
|---|---|---|---|---|
| 7,518,737 B2 * | 4/2009 | Hall | H04R 23/008 356/498 |
| 9,391,216 B2 * | 7/2016 | Papadopoulos | H10F 77/407 |

(Continued)

FOREIGN PATENT DOCUMENTS

| | | | |
|---|---|---|---|
| CN | 108291852 A * | 7/2018 | H04N 23/90 |
| EP | 1724652 | 11/2006 | |

(Continued)

OTHER PUBLICATIONS

Lucas Samuel Lincoln et al, An elastomeric insole for 3-axis ground reaction force measurement, The Fourth IEEE RAS/EMBS International Conference on Biomedical Robotics and Biomechatronics Roma, Italy. Jun. 24-27, 2012, pp. 1512-1517 (Year: 2012).*

(Continued)

*Primary Examiner* — Stephanie E Bloss
*Assistant Examiner* — Kevin C Butler
(74) *Attorney, Agent, or Firm* — Klarquist Sparkman, LLP

(57) ABSTRACT

Sensors include an optical source configured to emit a beam directed to an opposing surface having a reflectance pattern, and an optical detector situated in relation to the optical source to detect a portion of the beam reflected by the opposing surface and to produce an output signal that varies based on (i) a relative displacement between the reflectance pattern and the optical detector and (ii) a spatially variable reflectance resulting from the relative displacement. Reflectance patterns can be spatially variable and/or randomly
(Continued)

arranged. Displacements in a compressive or tensile direction can be detected. Methods of operation and fabrication of sensors are also disclosed.

33 Claims, 39 Drawing Sheets

(52) U.S. Cl.
CPC ............ *A61B 5/6811* (2013.01); *G01B 11/16* (2013.01); *A61B 2562/0266* (2013.01)

(58) Field of Classification Search
USPC ...................................................... 73/862.624
See application file for complete search history.

(56) References Cited

U.S. PATENT DOCUMENTS

| | | | | |
|---|---|---|---|---|
| 10,602,981 | B2 * | 3/2020 | Karnik | A61B 5/681 |
| 11,829,180 | B2 * | 11/2023 | Wang | G06F 3/038 |
| 2006/0192976 | A1 * | 8/2006 | Hall | G01B 9/02051<br>356/521 |
| 2007/0040107 | A1 * | 2/2007 | Mizota | G01L 5/228<br>250/221 |
| 2009/0302242 | A1 * | 12/2009 | Papadopoulos | H10F 77/50<br>250/552 |
| 2010/0213360 | A1 * | 8/2010 | Daiku | G01L 1/247<br>250/231.19 |
| 2018/0066937 | A1 * | 3/2018 | Ikeda | G01B 11/18 |
| 2018/0328814 | A1 * | 11/2018 | Panda | G01N 3/303 |

FOREIGN PATENT DOCUMENTS

| | | | | | |
|---|---|---|---|---|---|
| EP | 1724652 | A2 | * | 11/2006 | A47L 11/00 |
| EP | 3 693 139 | | | 8/2020 | |
| EP | 3693139 | A1 | * | 8/2020 | G01L 1/24 |
| JP | 4780204 | B2 | * | 9/2011 | G01L 1/247 |
| JP | 6794727 | B2 | * | 12/2020 | G01B 11/18 |
| KR | 100677279 | B1 | * | 2/2007 | A47L 11/00 |
| WO | WO-2005029028 | A1 | * | 3/2005 | G01L 5/166 |

OTHER PUBLICATIONS

Leal-Junior et al, 3D-printed POF insole: Development and applications of a low-cost, highly customizable device for plantar pressure and ground reaction forces monitoring, Optics and Laser Technology 116 (2019) 256-264 (Year: 2019).*
Jeroen Missinne et al., Two axis optoelectronic tactile shear stress sensor, Sensors and Actuators A 186 (2012) 63-68 (Year: 2012).*
International Search Report and Written Opinion for related International Application No. PCT/US2022/024116, mailed Oct. 5, 2022, 20 pages.
Lincoln et al., "An elastomeric insole for 3-axis ground reaction force measurement," *The Fourth IEEE RAS/EMBS International Conference on Biomedical Robotics and Biomechatronics*, pp. 1512-1517 (Jun. 24-27, 2012).
Missinne et al., "Embedded Flexible Optical Shear Sensor," *Sensors*, 5 pages, (Nov. 2010).
Missinne et al., "Flexible Shear Sensor Based on Embedded Optoelectronic Components," *IEEE Photonics Technology Letters*, 23(12):771-773 (Jun. 15, 2011).
Missinne et al., "Two Axis Optoelectronic Tactile Shear Stress Sensor," *Sensors and Actuators A: Physical*, 186:63-68 (Oct. 1, 2012).
Missinne et al., "Ultra Thin Optical Tactile Shear Sensor," *Procedia Engineering*, 25:1393-1396 (Dec. 2011).

* cited by examiner

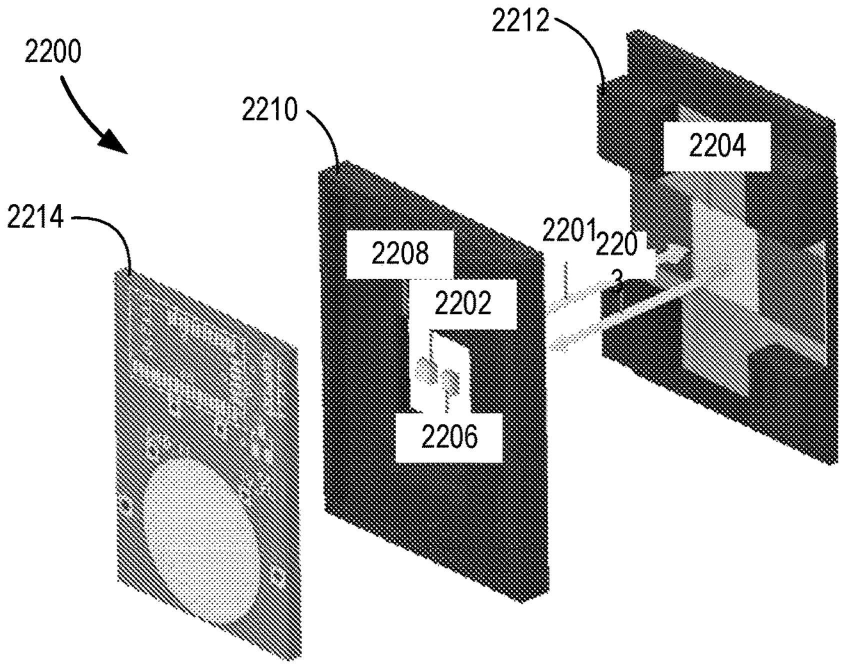
FIG. 22
FIG. 23A
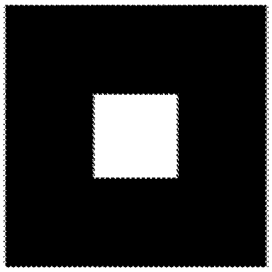
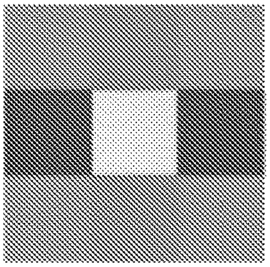
FIG. 23B
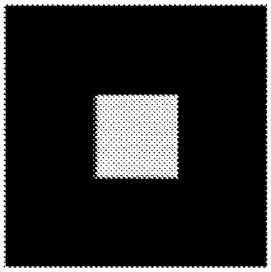
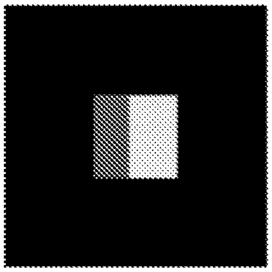
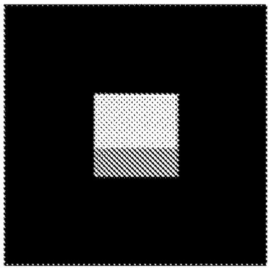
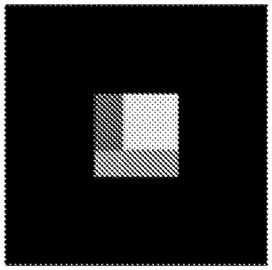
FIG. 23C
FIG. 23D
FIG. 23E
FIG. 23F

STRESS AND DISPLACEMENT SENSORS AND METHODS OF SENSING

CROSS REFERENCE TO RELATED APPLICATIONS

This to is the U.S. National Stage of International Application No. PCT/US2022/024116, filed Apr. 8, 2022, which was published in English under PCT Article 21(2), which in turn claims the benefit of U.S. Provisional Application No. 63/172,615, filed Apr. 8, 2021. The provisional application is incorporated herein in its entirety.

FIELD

The field is displacement sensing, including shear sensing based on displacement.

BACKGROUND

Use of prostheses can improve mobility, health, and quality of life; however, short and long-term variation in residual limb volume and shape can compromise the integrity of the residual limb-prosthetic socket interface, even for sockets that initially fit optimally. Sub-optimal socket fit exposes the residual limb to elevated localized shear stresses, which can macerate tissue giving rise to skin ulceration and pain. These conditions can lead to mobility deficits, prosthesis disuse, and reduced quality of life. Thus, there is a need for non-invasive sensors capable of measuring shear stresses occurring at the prosthetic socket and residual limb interface.

Other types of shear stress sensors for this application have been developed previously. However, many previous designs were based on capacitive sensing principles, which often necessitate bulky packaging and are sensitive to electromagnetic interface from the human body and surrounding environment. Such designs also typically require modifications to the prosthetic socket to accommodate bulky housing, wires, and power supplies. Another drawback to many previous designs for in-socket shear sensors is the inability to measure stress in more than one direction. Prohibiting measurement of the resultant stress can make the sensors extremely sensitive to placement and orientation errors, or increase bulk, complexity, or require numerous sensor units to achieve sensing of different shear axes. Furthermore, there is a more general need for displacement, shear, and/or strain sensors for a variety of applications which currently suffer from similar problems. Accordingly, a need remains for improved sensors and related techniques that can address the drawbacks of existing sensors.

SUMMARY OF THE INVENTION

Examples of the disclosed technology include sensors and sensing techniques for measuring shear stress and/or shear strain and/or shear displacement and/or compressive/tension stress compressive/tension strain and/or compressive/tensile displacement, with an optical detector and optical source arranged in relation to a first surface and an opposing surface having a reflective pattern. Characteristics of a detected reflected beam change in response to loading causing relative displacement of the surfaces.

According to a first aspect of the disclosed technology, sensors include an optical source situated in relation to a first surface and configured to emit a beam directed to an opposing surface having a spatially variable reflectance pattern, and an optical detector situated in relation to the optical source to detect a portion of the beam reflected by the opposing surface and to produce an output signal that varies based on (i) a relative displacement between the reflectance pattern and the optical detector and (ii) a spatially variable reflectance resulting from the relative displacement. In some examples, the optical detector comprises a single detection element and the output signal provides multi-axis displacement information along perpendicular shear axes. Some examples further include an intermediate transparent layer situated adjacent to the optical source and optical detector, wherein the layer is configured to deform to provide the displacement through a mechanical coupling with the opposing surface. In some examples, the intermediate transparent layer is situated to receive and transmit the beam and the reflected portion through the intermediate transparent layer. In some examples the intermediate transparent layer comprises an elastomer transducer layer. In some examples the elastomer transducer layer comprises polydimethylsiloxane (PDMS). In some examples, the elastomer transducer layer comprises a thickness and curing characteristics configured to define a shear modulus. Some examples further include a sensor housing configured to support the optical source, optical detector, and/or intermediate transparent layer in fixed relation to each other. Some examples further include a base plate attached to the sensor housing, and/or intermediate transparent layer, wherein the base plate comprises the opposing surface. In some examples, the optical detector comprises an aperture mask configured to define the amount of the detected portion by controlling the amount of area of the opposing surface viewed by the optical detector. In some examples, the spatially variable reflectance pattern comprises a repeating reflectance pattern and the aperture mask comprises a repeating aperture mask pattern associated with the repeating reflectance pattern. In some examples, respective repetition periods of the repeating reflectance pattern and repeating reflectance pattern are configured to provide a tolerance for recalibrating the sensor after a slip displacement between the optical detector and the opposing surface. In some examples, the spatially variable reflectance pattern comprises a spatially variable color reflectance pattern configured to reflect light by different amounts according to the spatially variable color. In some examples, the spatially variable color reflectance pattern comprises a first pattern area having a first color profile, a pair of second pattern areas having a common second color profile and situated on opposing sides of the first pattern area along a first shear axis, and a pair of third pattern areas having a common third color profile and situated on opposing sides of the first pattern area along a second shear axis perpendicular to the first shear axis. In some examples, the spatially variable color reflectance pattern further comprises four fourth pattern area having a fourth color profile having a reflectance common with the second and third color profiles, wherein the four fourth pattern areas are situated in a corner relationship to the first pattern area and the second and third opposing pattern areas. In some examples, the optical source comprises a red, green, blue (RGB) light emitting diode (LED). In some examples, the first color profile is a green color configured to reflect the green light of the RGB LED, the second color profile is one of blue or red color configured to reflect the corresponding blue or red light of the RGB LED, and the third color profile is other one of the blue or red color configured to reflect the corresponding blue or red light of the RGB LED. In some examples, the fourth color profile is a magenta color configured to reflect both the blue and the red light of the RGB LED. Some examples further include a processor and memory configured with processor-executable instructions that cause the processor to vary the spectral content of the beam produced by the optical source over time, receive the output signal from the optical detector and associate different output signal times with the timing of the variable spectral content, and determine a reflectance change associated with the relative displacement. In some examples, the memory is configured with processor-executable instructions that cause the processor to measure, based on the reflectance change, a shear stress and/or displacement between (i) the opposing surface and the (ii) optical source and optical detector. In some examples, the spatially variable reflectance pattern comprises a spatially variable gray scale reflectance pattern configured to reflect light by different amounts according to an intensity dependent gray scale spatial variation. In some examples, the optical source comprises a white light source. In some examples, the optical detector comprises one or more optical filters configured to attenuate light outside of a selected wavelength or wavelength range. In some examples, the one or more optical filters comprise a plurality of bandpass filters configured to attenuate different wavelengths or wavelength ranges of a spectrum of light of the beam reflected by the opposing surface. Some examples further include a processor and memory configured with processor-executable instructions that cause the processor to receive the output signal from the optical detector, wherein the optical detector is configured to detect a variation of spectral content of the reflected beam based on the optical filters, and determine a reflectance change associated with the relative displacement and the detected variation of spectral content. In some examples, the memory is configured with processor-executable instructions that cause the processor to measure, based on the reflectance change, a shear stress and/or displacement between (i) the opposing surface and the (ii) optical source and optical detector. In some examples, the optical detector comprises a photoresistor and the output signal comprises a variable resistance signal. In some examples, the optical detector comprises a phototransistor and the output signal comprises a variable voltage or current signal. In some examples the optical detector comprises a photodiode and the output signal comprises a variable voltage or current signal. In some examples the opposing surface comprises an integral or attached part of an object. In some examples, the opposing surface comprises an adhesive layer arranged on one or both of a side presenting the opposing surface and a side opposite the side presenting the opposing surface. In some examples, the adhesive layer is configured to adhere to a sensor housing or an elastomer transducer layer arranged between the sensor housing and the opposing surface. In some examples, the adhesive layer is configured to adhere the side opposite the side presenting the opposing surface, to a shearing surface. Some examples further include a shade expander configured to expand in a direction of the relative displacement in response to a displacement perpendicular to a plane of the relative displacement, wherein the expansion in the direction of the relative displacement is configured to reduce the portion of the reflected detected by the optical detector. In some examples, the shade expander comprises at least one set of opposing extension members configured to displace towards each other under compressive load and produce the expansion in the direction of the relative displacement based on a contact between the set of opposing extension members. In some examples, the shade expander comprises at least one expandable column extending between the opposing surface and the first surface and configured to expand in the direction of the relative displacement based on the perpendicular displacement. Some examples further include a processor and memory configured with processor-executable instructions that cause the processor to determine a reflectance change associated with the perpendicular displacement. In some examples, the memory is configured with processor-executable instructions that cause the processor to measure, based on the reflectance change, a compressive stress between (i) the opposing surface and the (ii) optical source and optical detector. In some examples, the opposing surface comprises a randomized pixel pattern. In some examples, the randomized pixel pattern is configured to provide a variation in the output signal through the relative displacement, wherein the variation is configured to provide a discrimination between a positive and negative directionality based on the randomized pixel pattern and a data classifier. In some example, the data classifier is a k-nearest-neighbor classifier.

According to another aspect of the disclosed technology, prosthesis comprise at least one sensor of any of the examples described herein. In some examples the opposing surface of the sensor is arranged on a residual limb. In some examples, the prosthesis comprises a prosthetic socket and the sensor housing is embedded within the socket.

According to another aspect of the disclosed technology, a shoe comprises at least one sensor of any of the examples described herein. In some examples, the opposing surface of the sensor is arranged at an insole of the shoe such that it is facing down towards a midsole. In some examples, the sensor housing is embedded within a midsole of the shoe.

According to another aspect of the disclosed technology, methods include emitting a beam from an optical source and directing the beam to an opposing surface having a spatially variable reflectance pattern, and with an optical detector situated in relation to the optical source, detecting a portion of the beam reflected by the opposing surface and producing an output signal that varies based on (i) a relative displacement between the reflectance pattern and the optical detector and (ii) a spatially variable reflectance resulting from the relative displacement. Further methods comprise operation of any of the sensor components of any of the sensors described herein. Further methods include fabrication, manufacture, or installation of any of the sensors or components of the any of the sensors described herein.

According to another aspect of the disclosed technology, methods include receiving sensor data describing a reflectance of a portion of a reflectance pattern, wherein the reflectance pattern has a spatially variable reflectance, and estimating a position of the portion by processing the data through a classifier trained on the spatially variable reflectance. In some examples, the classifier is a k-nearest-neighbor classifier. In some examples, the reflectance pattern is a 2D array of pixels with a random reflectance. In some examples, the portion comprises a plurality of the pixels. In some examples, the pixels include color, gray scale, rotated, solid, and/or axially aligned pixels. Some examples further include determining a displacement, shear stress, and/or shear strain based on the estimated position and a previous position of the reflectance pattern. Some examples further include any of the methods in which a beam is emitted from an optical source and directed to an opposing surface having a spatially variable reflectance pattern, and with an optical detector situated in relation to the optical source, a portion of the beam reflected by the opposing surface is detected and an output signal is produced that varies based on (i) a relative displacement between the reflectance pattern and the optical detector and (ii) a spatially variable reflectance resulting from the relative displacement, wherein the data corresponds to or is based on the output signal. Some examples further include training the classifier with the reflectance pattern by measuring a reflectance at a plurality of positions across an area of the reflectance pattern.

According to another aspect of the disclosed technology, sensors include an optical source situated in relation to a first surface and configured to emit a beam directed to an opposing surface having a reflectance pattern, a shade expander configured to expand in a direction laterally to the emission direction of the beam in response to a relative displacement of the first surface and the opposing surface towards each other, and an optical detector situated in relation to the optical source to detect a portion of the beam reflected by the opposing surface and to produce an output signal that varies based on the expansion of the shade expander in the lateral direction.

According to a further aspect of the disclosed technology, methods include emitting a beam from an optical source situated in relation to a first surface and directing the beam to an opposing surface having a reflectance pattern to produce a reflected beam, changing a light intensity of the reflected beam with a shade expander in response to a relative displacement between the first surface and opposing surface, with an optical detector situated in relation to the optical source, detecting a portion of the reflected beam and producing an output signal that varies based on the relative displacement, and estimating a compressive or tensile force and/or displacement based on the output signal.

The foregoing and other objects, features, and advantages of the disclosed technology will become more apparent from the following detailed description, which proceeds with reference to the accompanying figures.

BRIEF DESCRIPTION OF THE DRAWINGS

FIGS. 20A-2B are graphs of accuracy and misclassification cost for tested patterns. Data are mean±standard deviation.

FIG. 22 is an exploded perspective view of another example sensor.

FIGS. 23A-23F are schematics showing relative displacement between Surfaces A and B under resting and shearing conditions.

DETAILED DESCRIPTION

Figure 1A:
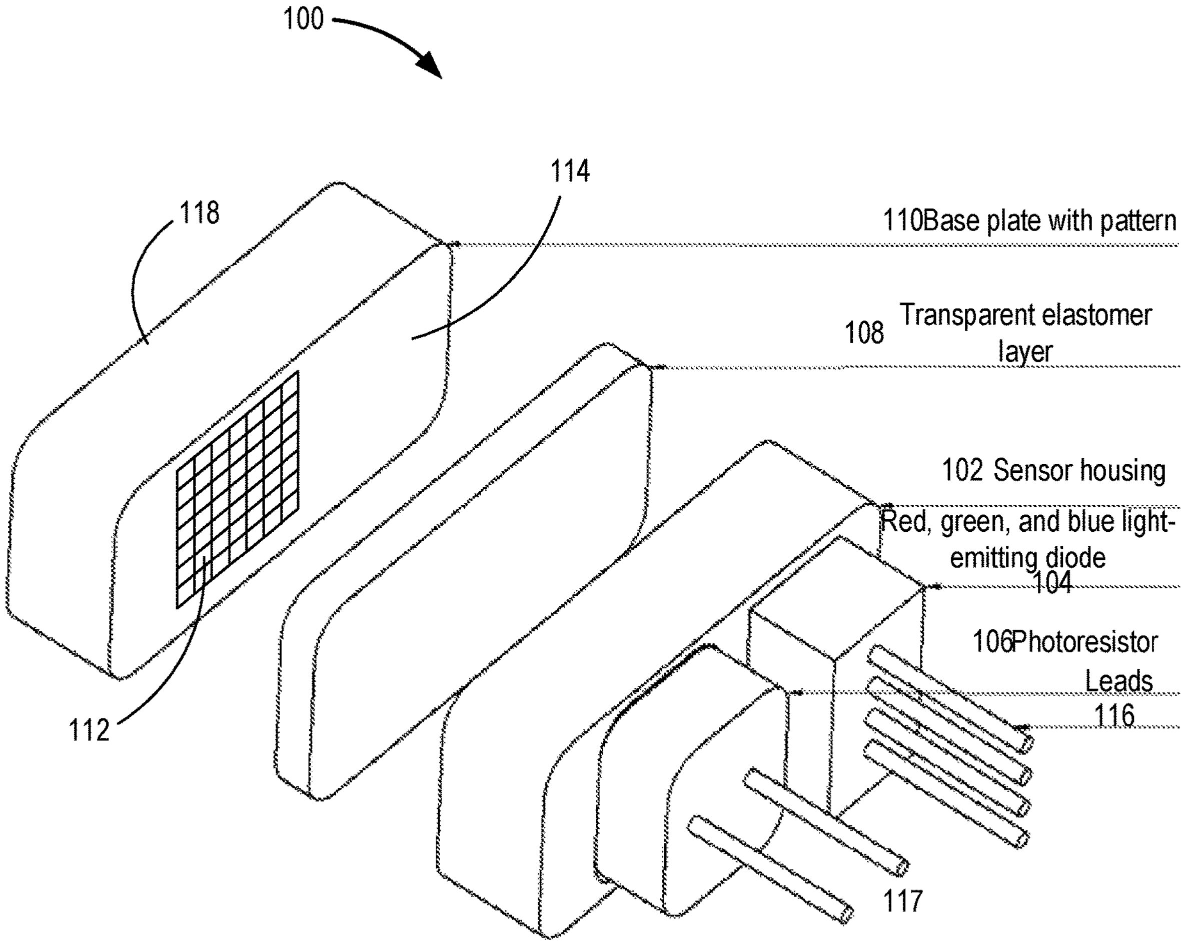
FIGS. 1A-1E are perspective views of an example arrangement of sensor components.
Figure 1B:
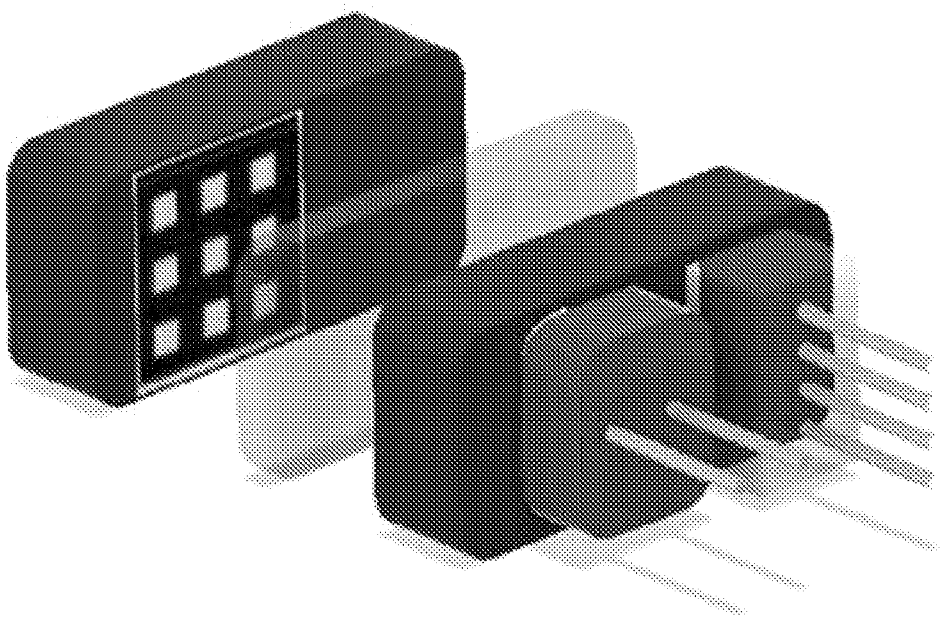
Figure 1C:
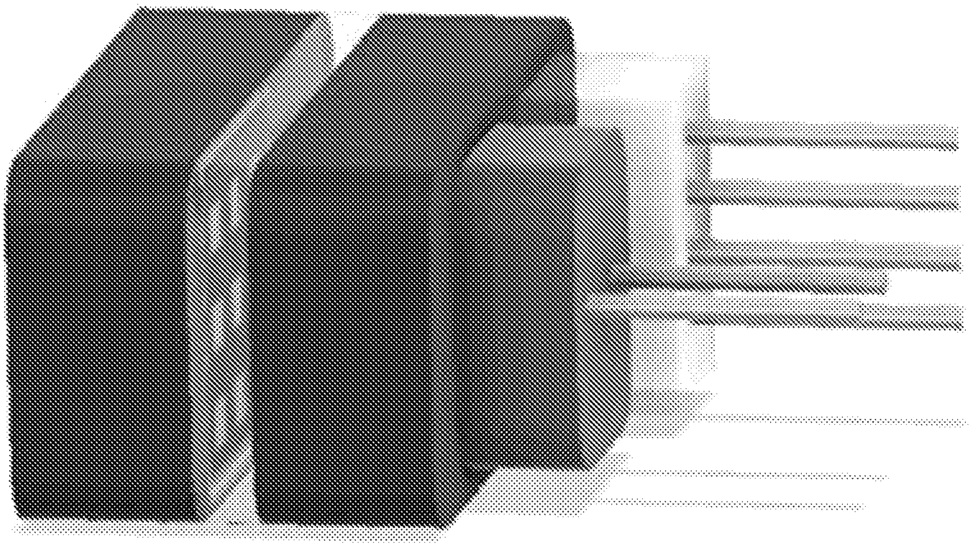
Figure 1D:
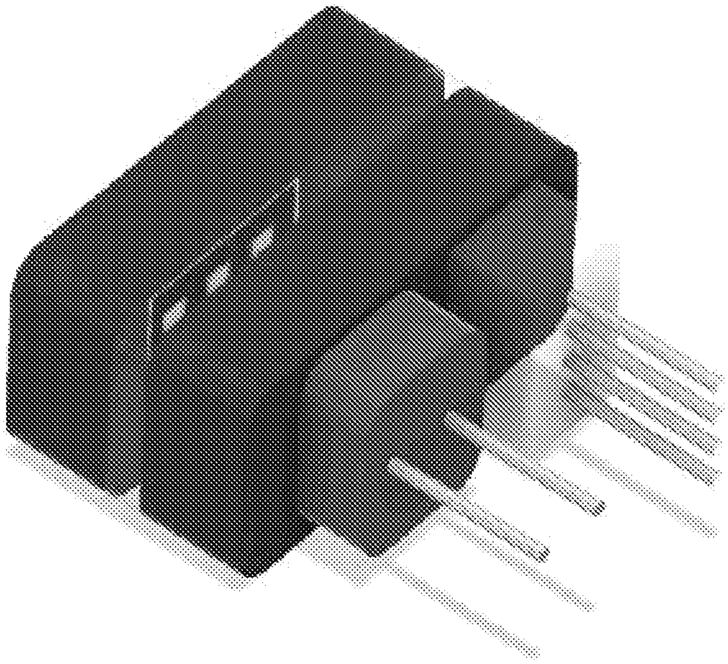
Figure 1E:
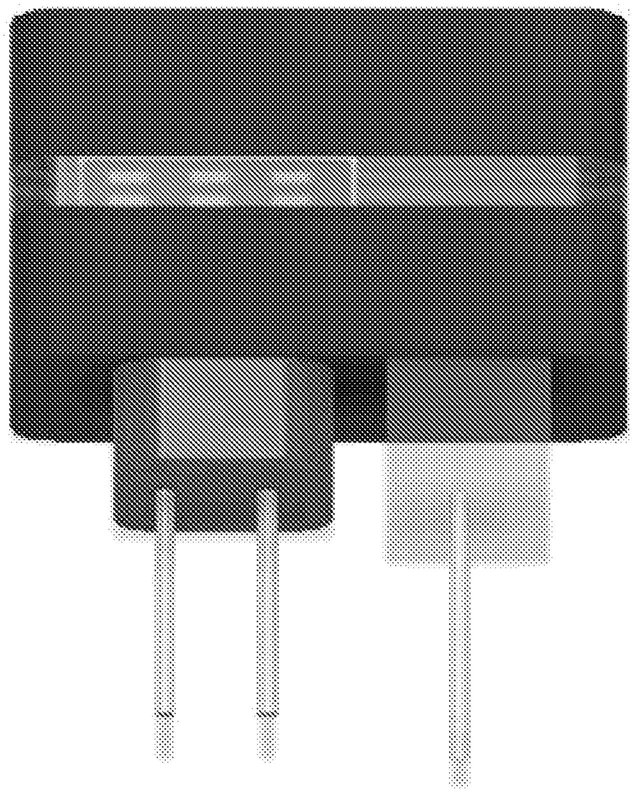

Examples of the disclosed technology can be used in numerous applications for optical-based sensing of compression, displacement, shear stress, and shear strain. Numerous disclosed examples sense shear stress based on optical coupling of reflected light. Selected examples can include contactless sensors for measuring shear stresses based on coupling of red, green, and blue light intensities. For example, color intensity of reflected light changes based on shearing between two bodies, which alters the visible color components of a surface having a colored grid. Shear stress can be calculated based on the intensity of light reflected by the various color(s) showing. Further examples can use changes in gray scale. Representative examples include a light source, light sensor, deformable transducer layer, and color grid for reflecting light, with parts coupled between first and second shearing bodies.

Sensor examples can have low power requirements and a small footprint, providing suitability for measuring shear stress in constrained environments. Example sensors can measure shear stress based on variations in light intensity, including using optical wavelength color reflectance variations or other reflectance variations, based on shearing of a surface with a reflecting pattern grid (such as a color or gray-scale pattern) with respect to a surface with a transparent window or window pattern.

Some example sensors can measure shear stresses along two perpendicular axes based on optical coupling between an optical source (e.g., a red, green, and blue light-emitting diode) and an optical detector (e.g., a photoresistor). Example sensors can enable measurement of interfacial shear stresses between two structures where shear strains appear. Selected applications can include monitoring of interfacial shear stresses between a residual limb and prosthetic socket. Additional applications in the medical space can include monitoring foot plantar tissue health in individuals with diabetic peripheral neuropathy and/or vascular dysfunction, or other scenarios requiring a contactless sensor with low power requirements and a small footprint.

Opto-electronics based sensing techniques are used to advantageously measure shear stress using thin and flexible housing packages, requiring minimal power, while being relatively unaffected by electromagnetism or normal force magnitude. Some disclosed sensor examples can be contactless, have a small footprint, remain unaffected by electromagnetic fields, and be able to measure shear stresses across a continuous range of orientations. In some examples that may be particularly advantageous in prosthetic arrangements, sensors can be integrated within current prosthetic socket systems without requiring substantial modifications or retrofits to that system, such as drilled holes to house sensors or port wires.

Introduction to Sensor Technology

The utility of tactile shear sensors is increasing rapidly, particularly for robotics, medical, geological, and orthopedic applications. Within the field of robotics, shear sensors are useful for detecting slippage in grasping devices or ground contact dynamics in walking devices. Among the many medical and orthopedic applications, measuring interfacial shear stresses between a residual limb and prosthetic socket can be used to manage socket fit and residual limb tissue health. Measuring shearing between a foot sole and shoe can be used to measure performance in athletes or to manage tissue ulceration among individuals with diabetic neuropathy and/or dysvascular conditions. Example disclosed sensors can be configured to satisfy the various design constraints associated with these applications, including by having a small footprint and flexible housings thereby making the sensors discreet or mechanically imperceptible to the user. Further, disclosed sensors can also be very light weight, have low power requirements, and be relatively unaffected by motion artifacts, normal force, or electromagnetic fields.

As discussed above, many existing shear sensors are based on capacitive sensing principles, which often necessitate bulky packaging and are sensitive to electromagnetic interference from the environment, nearby mechatronic systems, or human body. For example, Sanders and Daly (1993) used metal-foil strain gauges embedded in the wall of a prosthetic socket to measure residual limb-prosthetic socket interfacial shear stresses. However, the bulk and mass of these sensors necessitated that holes be cut in the wall of socket, thus limiting their usefulness in clinical or daily use settings. Cheng et al. (2010) developed a polymer-based capacitive sensing array for normal and shear force measurement in robotics and orthopedics. This design is more flexible but has a larger footprint than the metal-foil strain gauges. It also offers a relatively limited shear sensing capacity (<1 N), making it unsuitable for many robotic and orthopedic applications. Laszczak et al. (2015, 2016) developed a 3D-printed capacitive shear stress sensor. This sensor has a miniaturized design (20×20×4 mm), but is unable to differentiate between shear stresses along different axes.

In contrast to capacitive designs, optoelectronics-based sensors can be advantageous for measuring shear stress because they can be made thin, require minimal power, and be relatively unaffected by magnitude of normal force. Furthermore, devices based on optical sensing principles are generally unaffected by electromagnetic interference induced by the surroundings, human body, or other devices interacting with the sensor. Missinne et al. developed and validated a thin optical tactile shear sensor that senses shear stress based on optical coupling between a vertical-cavity surface-emitting later (VCSEL) and a photodiode, separated by a transparent elastomeric transducer layer. The sensor exhibited a repeatable sigmoidal relationship between photodiode current and shear stress for stresses up to 5 N. However, the device had a limited range of shear sensing, required high power to drive the VCSEL, and was generally unable to measure directionality of shear stresses, thereby limiting its usefulness for robotics, medical, and orthopedic applications.

As will be discussed further hereinbelow, disclosed optical-based sensors can be miniaturized with scalable designs that can be tuned to sense shearing of different magnitudes, including larger than 5 N, shear displacement and strain, and/or compressive force or displacement. Some disclosed examples can also be configured to differentiate directionality of the shear stresses and require low power. Disclosed sensors can be fabricated using a simple, low-cost, optoelectronic sensor based designs for measuring uni-axial or multi-axial shear stresses. Some examples can differentiate direction along an axis, e.g., left from right.

Examples of the Disclosed Technology

An example of a shear sensor 100 is depicted in FIGS. 1A-1E. The sensor 100 includes a structural housing 102 for supporting a light source 104 (e.g., a red, green, and blue light emitting diode is depicted) and an optical detector 106 for sensing resistance changes based on changes in light intensity. Example optical detectors can include photodetectors, photoresistors, photodiodes, phototransistors, etc. A transparent elastomer transducer layer 108 separates the sensor housing 102 from a base plate 110 having a spatially variable reflectance pattern, such as a color pattern grid 112 printed on the adjacent surface 114. The layer 108 can be transparent, such as with a continuous layer of PDMS. Other examples of the layer 108 can be non-transparent and arranged so that light can pass through, e.g., with blocks arranged over selected portions of the color pattern grid 112. Pattern examples can include gray scale patterns, and herein "color pattern" can sometimes refer to gray scale patterns. Some pattern examples can be arranged linearly. The color pattern grid 112 forms a two-dimensional pattern. The design can be contactless, in that the sensor 100 can be configured such that sensor does not require contact or adhesion with both shearing bodies or can be configured such that all electronics and wiring can be placed on one side of the sensor. Leads 116 from the light source 104 and leads 117 from the optical detector 106 can be coupled to separate electronic circuitry (not shown) including one or more processors, e.g., in a microcontroller unit, to control emission and sensing. For example, the microcontroller can be configured to control generation and timing of light emitted by the light source 104, and the detection of light by the optical detector 106. For example, in some timed examples, RGB light can be pulsed (e.g., sequentially at different wavelengths) and detection can occur with a broad spectrum photodetector. Some examples can be untimed, such as with a constant illumination of broad spectrum light and detection can occur with an RGB photodetector.

In various examples, the sensor housing 102 or the optical detector 106 fixedly arranged relative to the transparent elastomer layer 108 displaces relative to the base plate 110 during a shear event, using the deformability of the transparent elastomer layer 108. The light emitted from the light source 104 can be directed through the transparent layer 108 or it can be transmitted through another medium including free space. In some examples, the base plate 110 can be attached to the layer 108, e.g., at the surface 114, and another surface 118 of the base plate 110 can provide a surface through which shear force is transmitted with an adjacent shearing body. In this way, the sensor 100 can form a unit that can be attached to one of the two shearing bodies without being attached to the other. In further examples, the base plate 110 can be attached to one of the two shearing bodies (e.g., as a flexible substrate that can be affixed with an adhesive, as an integrated part of a shearing body) and the sensor housing 102 with transparent elastomer layer 108 can be attached to the other of the two shearing bodies. An interface between the layer 108 and the surface 114 of the base plate 110 can provide the surface through which shear force is transmitted between the two shearing bodies. In some examples, the layer 108 can comprise a portion on each of the base plate 110 and the sensor housing 102. In selected examples, the base plate 110 could be replaced by another body to fit a variety of sensing needs, including an existing surface of the other of the two shearing bodies. In a particular example, the sensor housing 102 could be embedded within a prosthetic socket and the base plate 110 could be replaced by a residual limb with the pattern 112 printed or placed thereon. FIGS. 1B-1E show various exploded and perspective views of the sensor 100.

Figure 2A:
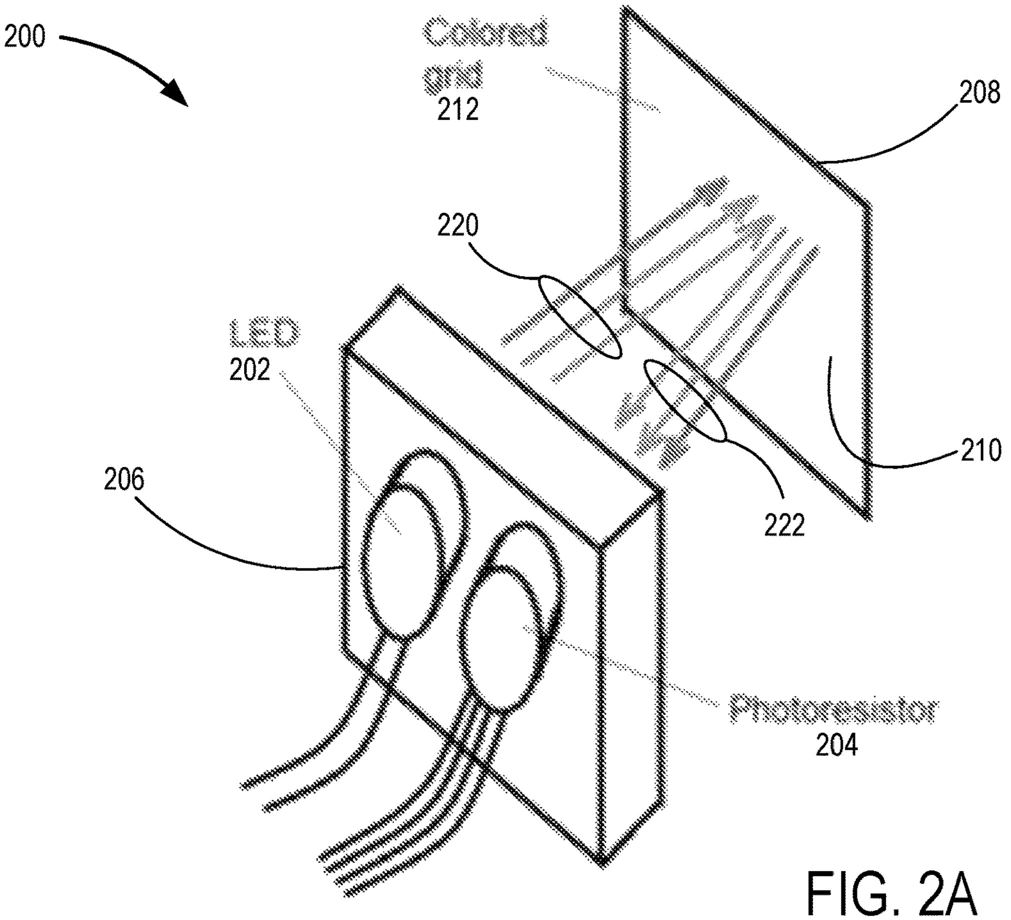
FIGS. 2A-2D are illustrative examples of sensing principles, showing contactless opto-electronics sensor (left), and schematic of shear sensing principles based on optical coupling between a red, green, and blue light-emitting diode and photoresistor (right).
Figure 2B:
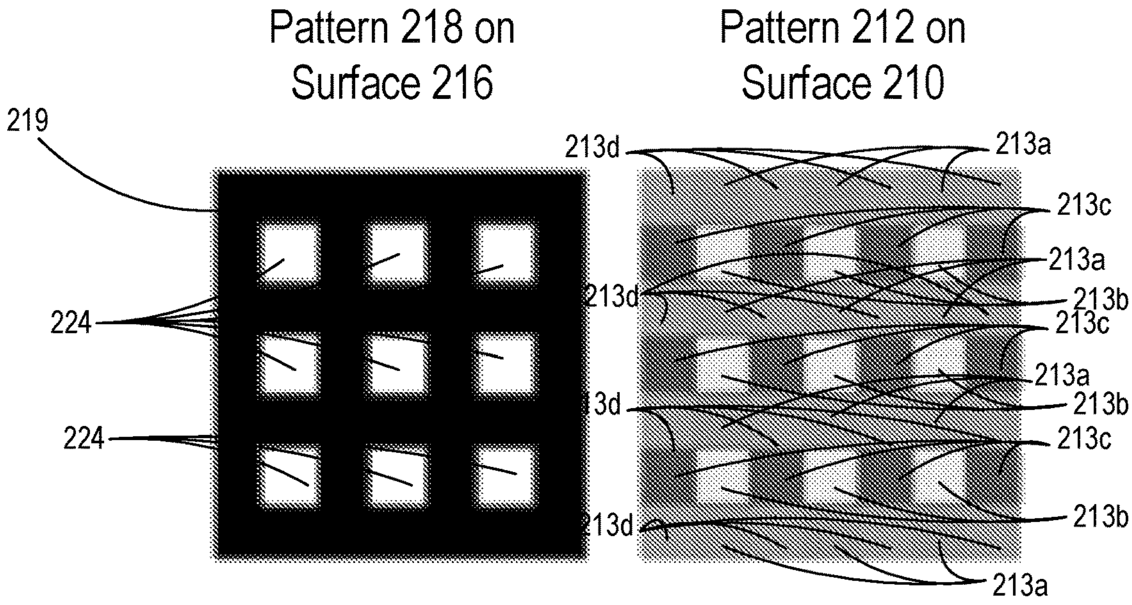
Figure 2C:
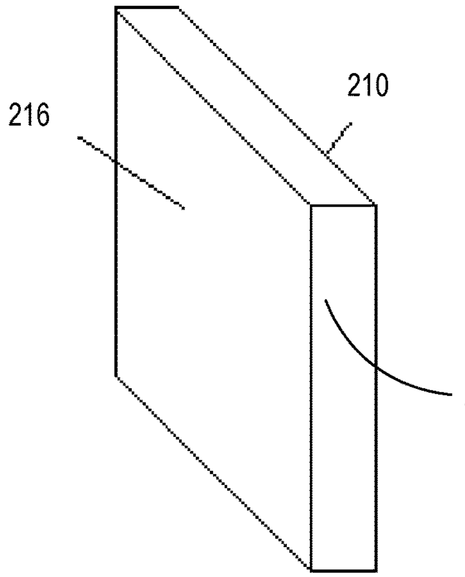

Various disclosed sensor examples can use sensing principles depicted in the example sensor 200 shown in FIGS. 2A-2D. The sensor 200 includes a light source 202 and an optical detector such as a photoresistor 204 in a fixed arrangement with respect to each other, e.g., coupled to a sensor housing 206. The sensor housing 206 is typically attached to a first shearing body. The sensor 200 can measure shear stress based on changes in optical coupling between the light source 202 (e.g., red, green, and blue light-emitting diode) and the photoresistor 204 and the variation in detected reflectance. A body 208 (e.g., a base plate or an adjacent second shearing body) is situated adjacent to the sensor housing 206 and includes a surface 210 having a colored grid 212 of red 213*a,* green 213*b,* blue 231*c,* and magenta 213*d* (blue+red) squares. For example, the pattern can include a square of a first color (e.g., green), squares of a second color (e.g., red) on opposite sides of the square of the first color along a first axis (e.g., vertical), squares of a third color (e.g., blue) on opposite sides of the square of the first color along a second axis (e.g., horizontal), and squares of a fourth color (e.g., magenta) at corner positions relative to the square of the first color. In some examples, such as shown in FIG. 2B, the color pattern can repeat.

The housing 206 and the body 208 can be separated by a transparent elastomer transducer layer 214. A surface 216 opposing the surface 210 can be defined by the sensor housing 206, layer 214, and/or window pattern 218 of a window 219, such as an aperture mask situated adjacent the photoresistor 204. In representative examples, a light beam 220 is emitted from the light source 202 and directed through the transparent elastomer transducer layer 214 to the surface 210. A reflected beam 222 is directed back through the layer 214 to be received through the window pattern 218 by the photoresistor 204. The aperture mask can include one or more aperture regions 224 that allow some of the reflected beam 222 to be received for detection by the photoresistor 204 or other optical detector. In further examples, one or both of the transmissions through the layer 214 can be through free-space or another material. In some examples, lens, mirrors, or other optical coupling components can be present to focus, direct, or couple the light beam 220 directed to the surface 210, e.g., adjacent to the light source 202, or to collect the reflected light 220 reflected by the colored grid 212, e.g., adjacent to the photoresistor 204 or window 219. Control circuitry is coupled to the light source 202 to repetitively cycle the color of the LED (red, green, and blue), while measuring the reflected light intensity as a resistance change at the photoresistor 204 during red ($R_r$), green ($R_g$) and blue ($R_b$) light illumination.

Figure 2D:
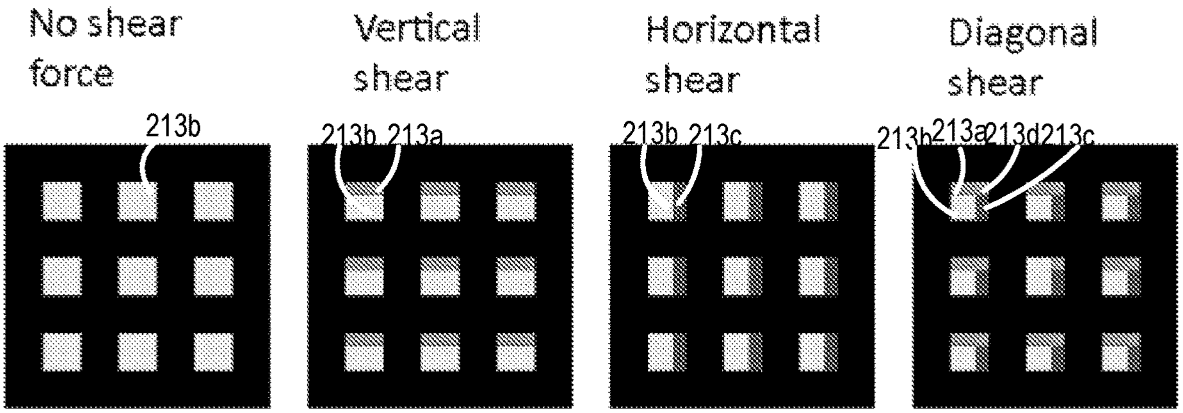

Referring to FIG. 2D, when there is no shear force between the first and second bodies, surfaces 210 and 216 are perfectly aligned with the green squares 213*b* and only green appears in the window. Thus, the sensor 200 will only measure a resistance change during green light, and no resistance change during blue or red light since there is no blue or red color to reflect the light ($R_g>0$, $R_r=R_b=0$). When a vertical shear force is present between the first and second bodies, surfaces 210 and 216 will be misaligned and the red squares 213*a* on the surface 210 pattern 212 will show through surface 216, leading to changes for $R_g$ and $R_r$. In representative examples, the values of $R_g$ and $R_r$ are inversely proportional and proportional to the vertical shear force, respectively. As a result, vertical shear force can be calculated as the ratio $R_r/R_g$, and horizontal shear force can be determined as $R_b/R_g$. In some examples, an amplified circuit and analog-to-digital converter are coupled to the photoresistor to convert an analog output signal in the form of a variable resistance into a digital signal for processing. However, resistances, ratios, and equalities/inequalities can vary in different examples. For example, an overlap in the blue and green wavelengths can cause resistances to satisfy $R_g>R_b>R_r$ resulting in a non-zero blue resistance where the surfaces 210, 216 are aligned with the green squares 213*b*.

Figure 3:
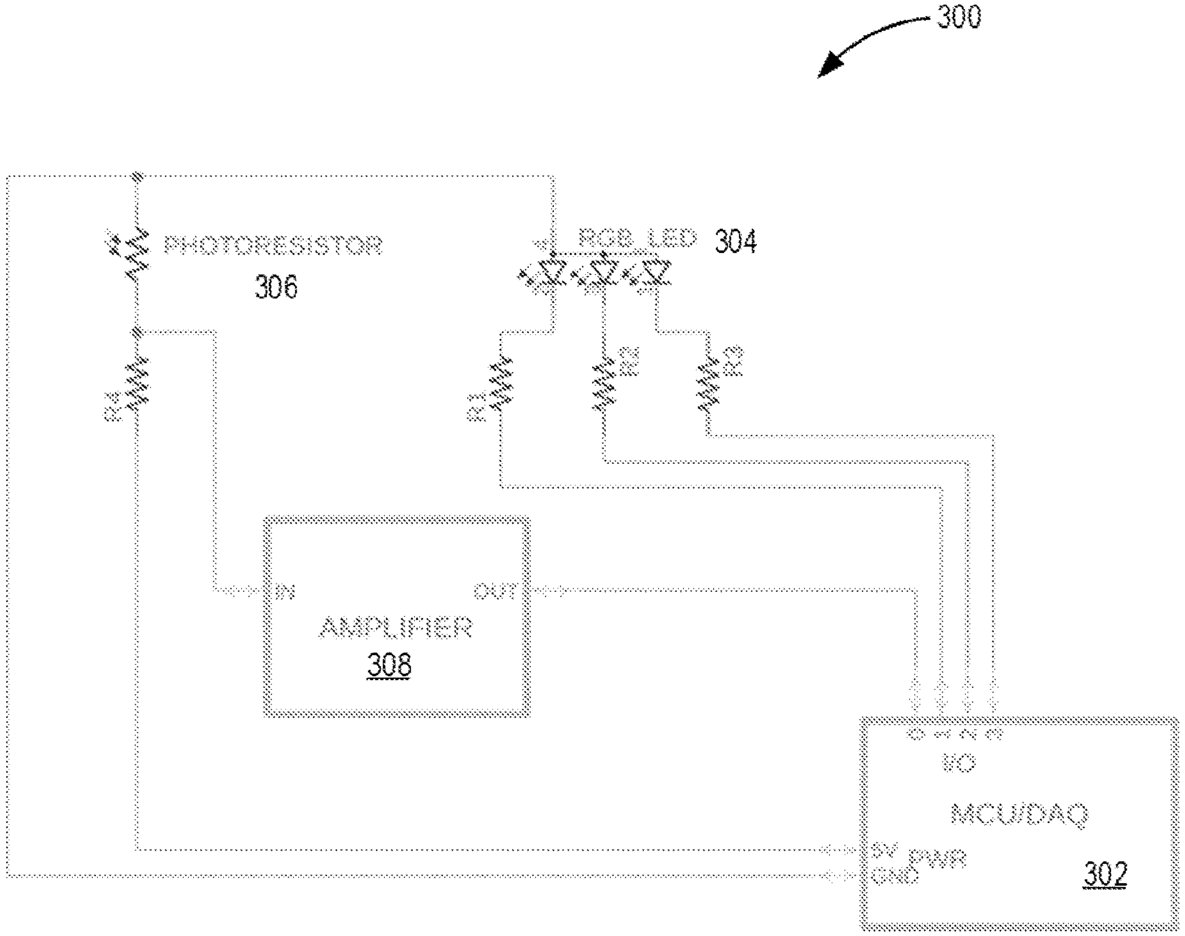
FIG. 3 is an example circuit diagram for controlling the operation of the optical sensors. MCU: Microcontroller Unit, DAQ: Data Acquisition system, PWR: Power, I/O: Input/Output.

FIG. 3 is example control circuitry 300 coupling different sensor components. It will be appreciated that numerous other sensor circuit configurations are possible and may enhance, optimize, or expand disclosed examples. The control circuitry 300 includes a microcontroller (MCU)/data acquisition (DAQ) unit 302, which can be configured to control the color and duty cycle of a common anode RGB LED 304 by controlling power to input/output pins. The MCU/DAQ 302 also can be coupled to a photoresistor 306 and measures resistance changes from the photoresistor 306, which can be translated into changes in magnitude and direction of shear stress. An example signal amplifier 308 can also be coupled to the photoresistor, which could be used to improve the ability to detect small changes in resistance. Other components can be included or removed in various examples to adjust measurement accuracy or tailor the circuit to the type of optical detector. For example, voltage dividers, wheatstone bridges, pull-down resistors, etc., can be used. In some examples, additional communication circuitry can be provided, such as wireless Bluetooth, WiFi, or other wireless modules, for communicating measurement data with a separate computing device, such as a computer, hand-held device, wearable computing device, etc.

Figure 4A:
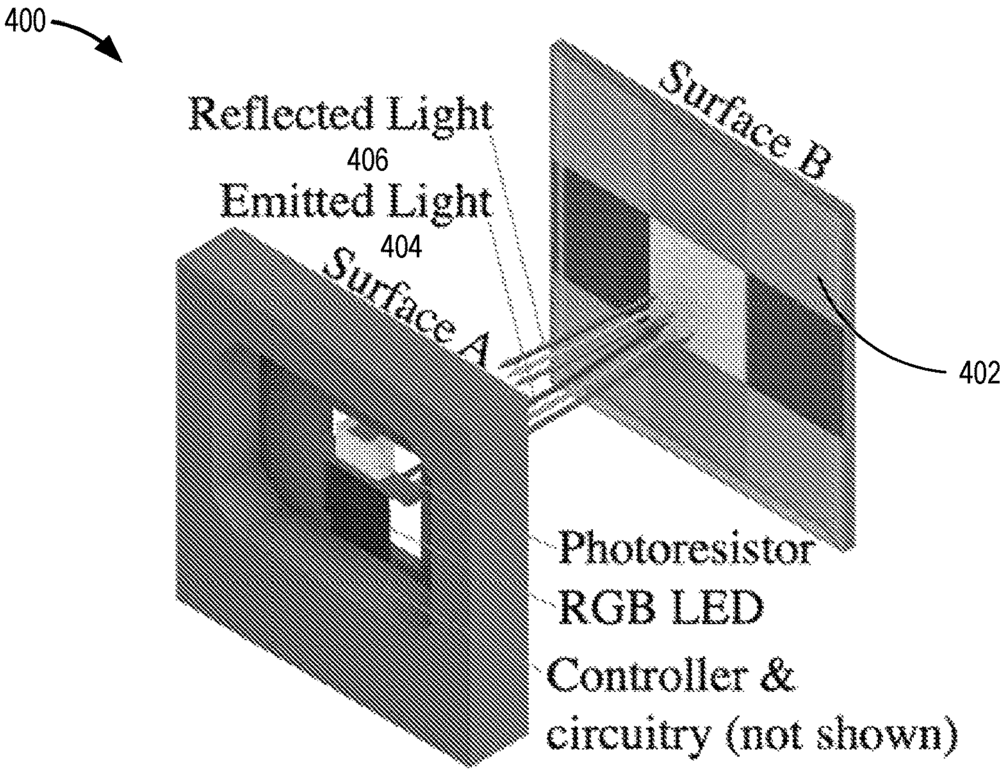
FIG. 4A is a perspective view of a contactless optoelectronic shear sensor.
Figure 4B:
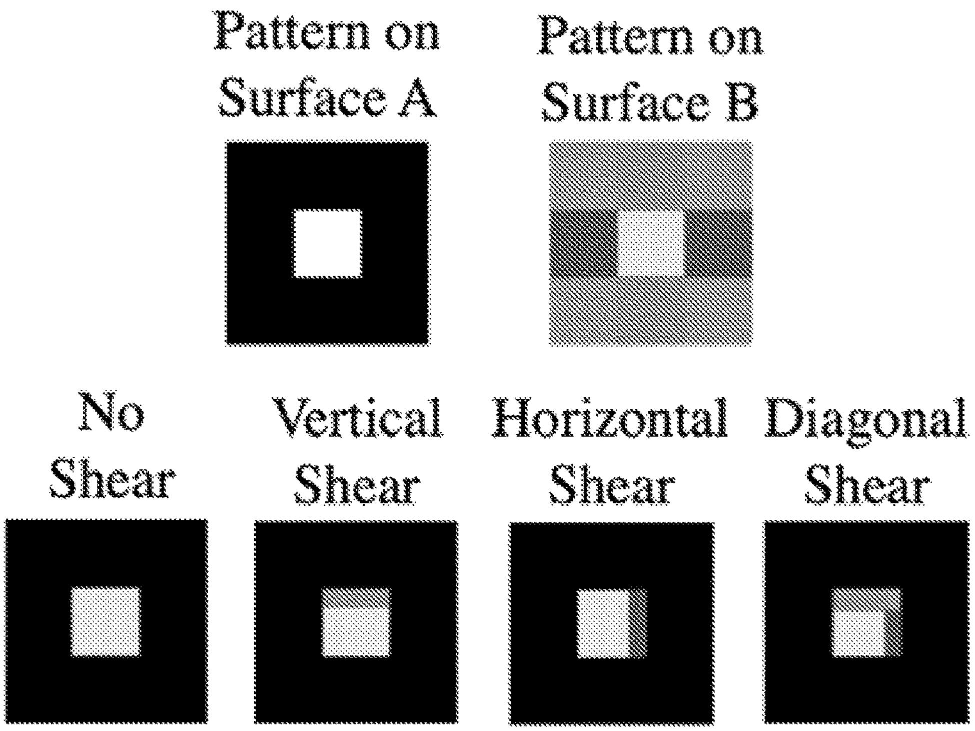
FIG. 4B are plan view schematics of shear sensing principles based on optical coupling between the RGB LED and photoresistor.

Another example sensor 400 is shown in operation in FIGS. 4A-4B. Example sensors can be configured with two-dimensional reflective pattern arrangements, such as colored grid pattern 402, so that multi-axial shear stress measurements can be performed. One-dimensional reflective pattern arrangements can be used in some examples as well, including gray-scale based or color-based. Reflectance variations are produced based on optical coupling between an optical detector, such as a photoresistor, and an optical light source, such as a red, green, and blue (RGB) light-emitting diode (LED). Other suitable optical detectors can include photodiodes, phototransistors, pixelated arrays, etc. However, photoresistors can be advantageous for their simplicity, low-cost, and small footprint. Suitable optical detectors can convert light intensity into an electrical signal, including resistance signals, voltage signals, current signals, etc. Contactless configurations can include all electronics and wiring at one side of the sensor, e.g., adjacent to the optical detector and/or optical source. The instrumented side of the sensor has a windowed pattern defined by a surface, e.g., Surface A, whereas an opposing side of the sensor displays the colored grid pattern 402 consisting of green, red, blue, and magenta (red +blue) squares on an opposing surface B. Other colors may be used in some examples. In some examples, the pattern on Surface B could be printed on a second sensor component or on an adjacent stationary surface or existing device (e.g., a shearing body on a robot). Controlling electronics cycle the LED color to produce emitted light 404 while measuring the intensity of reflected light 406 as a resistance change at the photoresistor during red ($R_r$), green ($R_g$), and blue ($R_b$) light illumination. The portion of the emitted light 404 that is reflected by the Surface B to become reflected light 406 can be determined by the color of the emitted light and the color of the surface that reflects the light. Because shear causes displacement of the colored grid pattern 402 relative to the windowed pattern, the amount of light that is reflected and received by the photoresistor varies according to the displacement and spatial reflectance characteristics of the colored grid pattern 402.

When there is no shear force applied to the sensor, Surfaces A and B are perfectly aligned, and thus only green appears in the window on Surface A (FIG. 4A). Under these conditions, the photodiode only measures a resistance change when the LED is emitting green light, since there is no blue or red color to reflect the light ($R_g>0$, $R_r=R_b=0$). A vertical shear force causes a relative displacement producing a misalignment of Surfaces A and B, e.g., through a shear deformation of an intermediate elastomer layer, and the red squares on Surface B are exposed through the window of Surface A, leading to resistance changes in $R_g$ and $R_r$. The values for $R_g$ and $R_r$ are inversely proportional and proportional to the magnitude of vertical shear force, respectively. Similarly, a horizonal shear force cause the blue on Surface B to be visible in the window on Surface A. As a result, vertical shear force can be calculated as the ratio $R_r/R_g$, and horizontal shear force can be determined as $R_b/R_g$.

However, perfect alignment at a nominal position and unloaded state such that reflectance from only a green square may be detected is not a requirement. For example, a misaligned position with two or more colors being detectable can be defined as a nominal position and displacements that produce variations in the detected resistances or other output signal values (e.g., voltage and/or current) can be used to determine uniaxial or multi-axial shear stresses. A calibration routine can be performed to assign detected resistance values under no shear load as a nominal or unloaded state. Over time the alignment of the pattern 402 relative to the optical detector can drift from a nominal state, e.g., due to slipping or wear. Such drift may be more likely in examples without rigid attachment between the color pattern 402 and a sensor housing or intermediate transparent layer. The calibration routine can be reperformed to reset the resistances detected that define an unloaded state. In some examples, the grid pattern 402 can be repeated (e.g., as shown in FIG. 2B) so that a displacement drift larger than the dimensions of the colored squares can be tolerated. For example, a the sensor can be electronically recalibrated without requiring replacement or the sensor or physical realignment of the sensor and grid pattern.

Figure 5A:
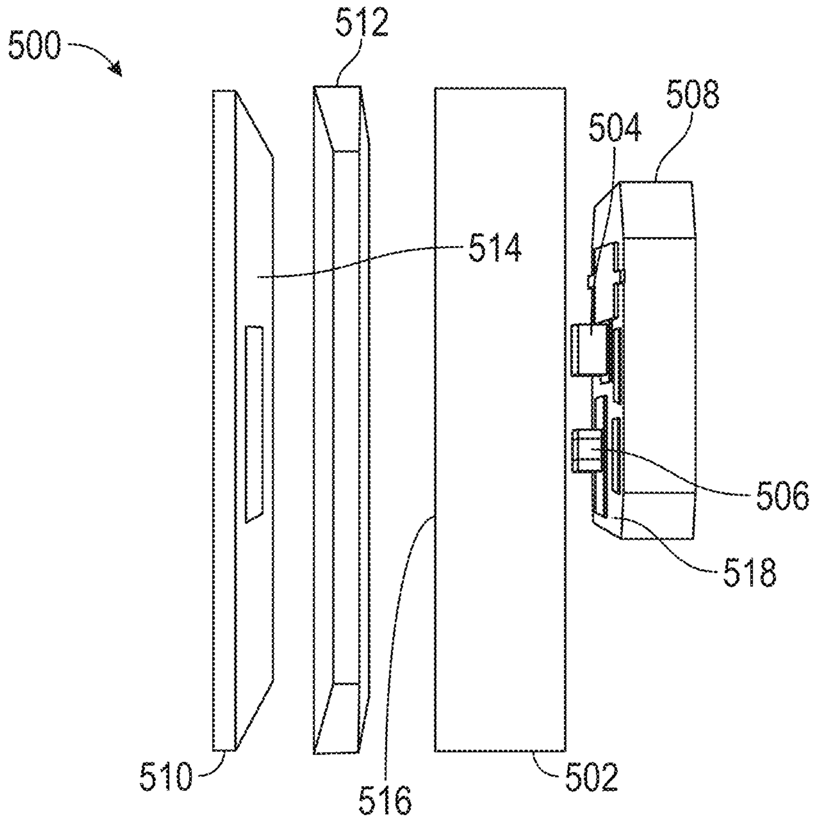
FIG. 5A is a side view of an example sensor architecture.
Figure 5B:
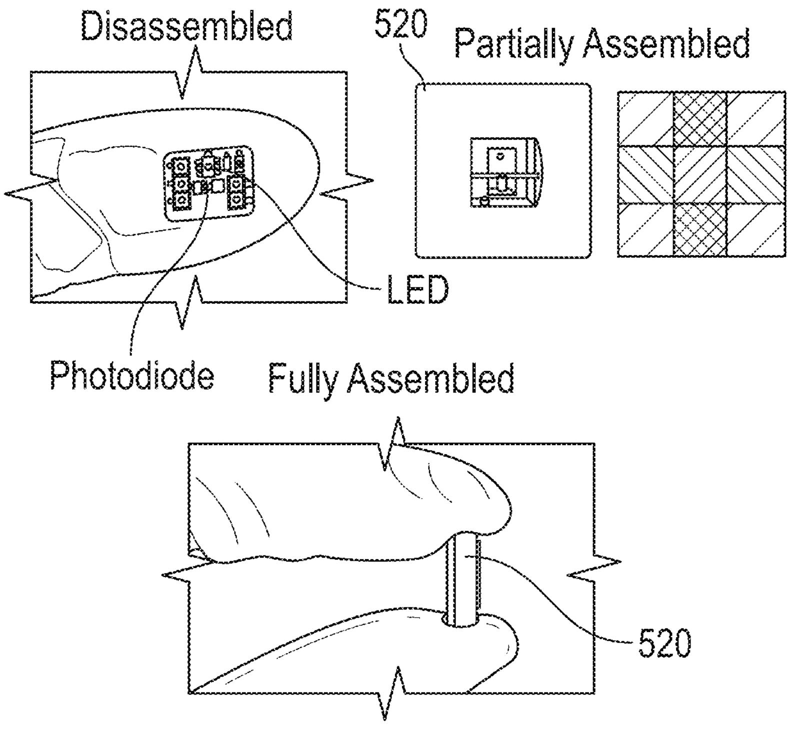
FIG. 5B are images of a disassembled sensor (left), sensor without elastomer layer (right), and fully-assembled sensor and circuitry (bottom).

FIGS. 5A-5B show another example sensor 500 that includes an instrumented housing 502, an LED 504 supported by the housing, a photodiode 506 to operate as an optical detector, control circuitry 508 to drive the LED 504 and process the output signal from the photodiode 506, a color pattern arranged on an opposing surface such as a plate 510, and an intermediate optically clear deformable polydimethylsiloxane (PDMS) elastomer layer 512 (e.g., Sylcap, MicroLubrol, Clifton, NJ) separating opposing surfaces 514, 516. In the particular embodiment shown, the packaging for the sensor 500, including circuitry, is 15×15×5 mm. A thickness of the sensor 500, e.g., perpendicular to the shear displacement, can depend upon the thickness of the PDMS elastomer layer 512. The range of shear stress magnitudes and sensitivity to changes in shear stress can be tuned based on PDMS layer thickness and curing conditions, which affects the material properties.

In a particular example, the LED (e.g., DotStar APA102-2020, Shenzhen LED Color Opto Electronic Co., Shenzhen, China) is 2×2×0.9 mm and emits red, green, and blue light at 620, 520, and 465 nm wavelengths, respectively. At 20 mA, the brightness for these colors is 300-330, 420-460, and 160-180 mcd. The photodiode 506 (e.g., Vishay Semiconductors, VEMD1060X01, Shelton, CT) is 1×2×0.9 mm with a 0.2 $mm^2$ active area. The photodiode 506 is sensitive to wavelengths ranging 350-1070 nm, which is inclusive of the red, green, and blue color spectra. The LED 504 and photodiode 506 are mounted to a printable circuit board (PCB) 518 (e.g., OshPark, Lake Oswego, OR) which can be housed in a 3D printed methylacrylate photopolymer resin 520. By employing rapid prototyping technology in the fabrication process, the cost-efficiency and versatility of the sensor 500 are improved. Within the housing 502, the LED 504 and photodiode 506 can be isolated such that photodiode 506 is only exposed to light reflected from surface 514 or exposure from other light is limited.

In an example fabrication method, a resin mold for the PDMS elastomer layer was 3D printed and adhered to a Teflon plate. The base agent and curing agent were poured into the mold and cured at room temperature for 24 hrs. After curing, the PDMS elastomer was removed from the mold trimmed to the dimensions of the sensor housing, and adhered to opposing surfaces 514, 516 of the sensor with an adhesive (e.g., Loctite 401). In a previous material characterization studies, the shear modulus of PDMS at room temperature was found to be 250-450 kPa. However, the material properties of PDMS are tunable by adjusting the geometry and curing parameters of the elastomer.

Figure 6A:
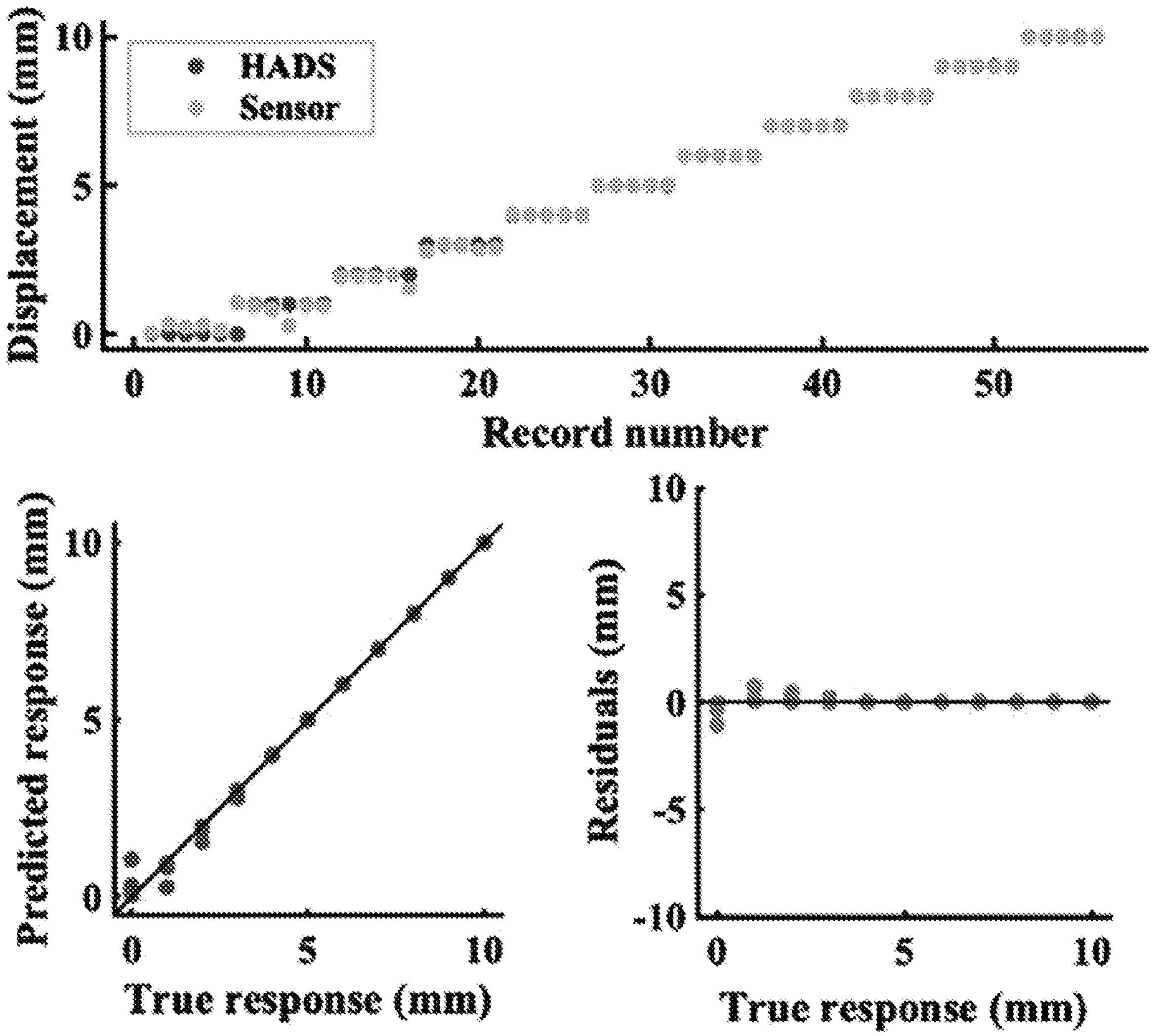
FIGS. 6A-6B are graphs of performance of a sensor example compared to High Accuracy Displacement Sensor (HADS), measuring horizonal (FIG. 6A) and vertical (FIG. 6B) displacements.
Figure 6B:
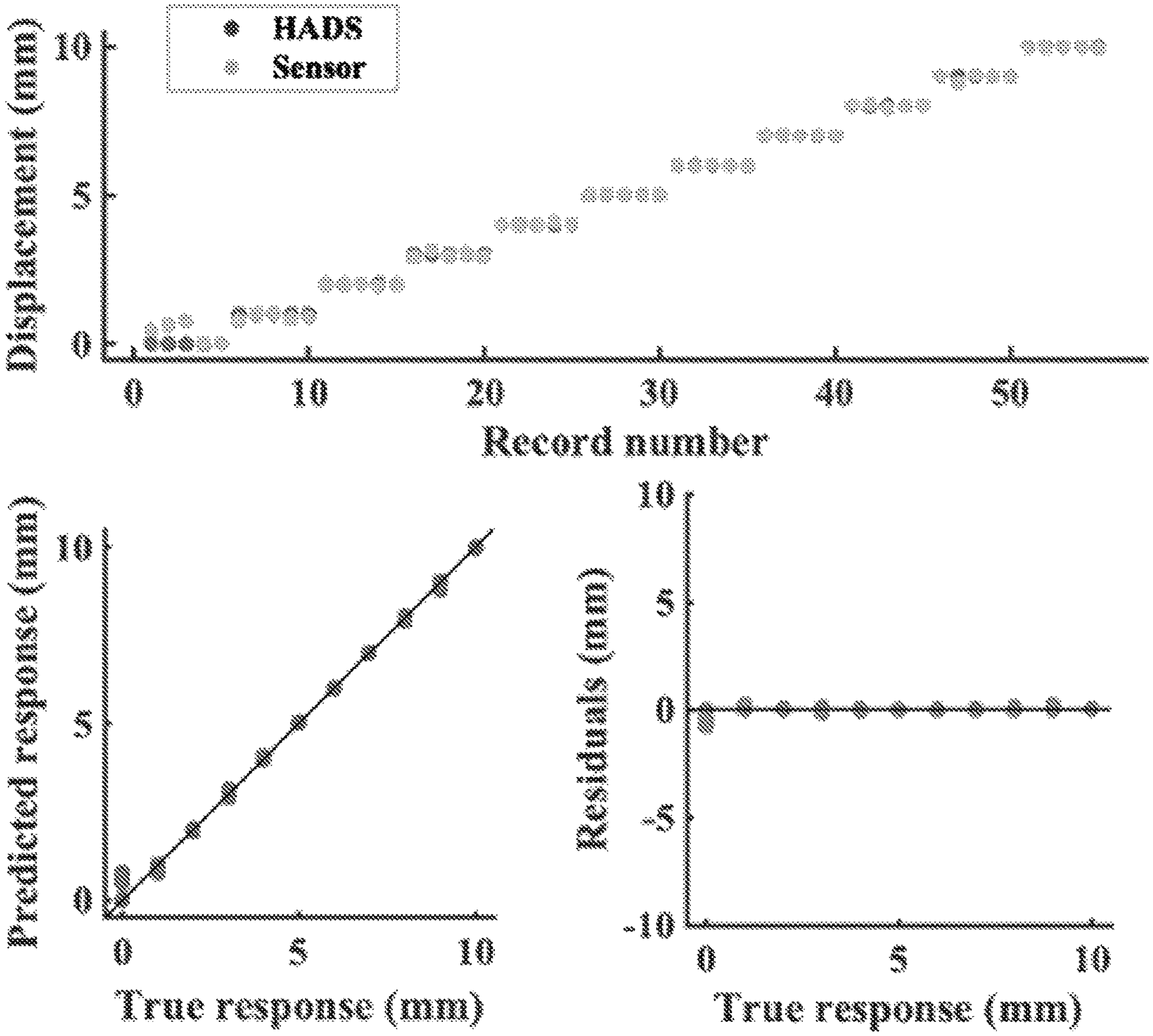

In an experimental characterization of the sensor 500, sensor response to both displacement and applied shear force were measured. Measuring the response to displacement can characterize the baseline performance of the sensor components. Measuring the response to shear stress can characterize the sensor's performance under conditions for shear measurement applications. To apply controlled displacement, a 3D-printed housing was fabricated to secure the sensor components in a materials testing system (EnduraTEC ELF, TA Instruments, New Castle, DE). For displacement tests, a 3 mm-thick spacer was placed between the two sides of sensor in place of the elastomer. The instrumented side of the sensor 500 (e.g., surface 516) was displaced with respect to the surface 514 in 1 mm increments up to 10 mm. At each 1 mm position, a static measurement of RGB color intensity was recorded by cycling each LED color 10 times at 50 Hz and recording the average of the 10 measurements for each color. To measure the repeatability of the sensor 500, 5 trials were completed and inter-trial variability was calculated. Measurement results are depicted in FIG. 6A. Measurements were then repeated in the horizontal direction and the results are depicted in FIG. 6B. Sensor-derived measurements of displacement were then compared to measurements from the materials testing system's integrated High Accuracy Displacement Sensor (HADS) (EnduraTEC ELF, TA Instruments, New Castle, DE), with such results also shown in FIGS. 6A-6B.

Figure 7A:
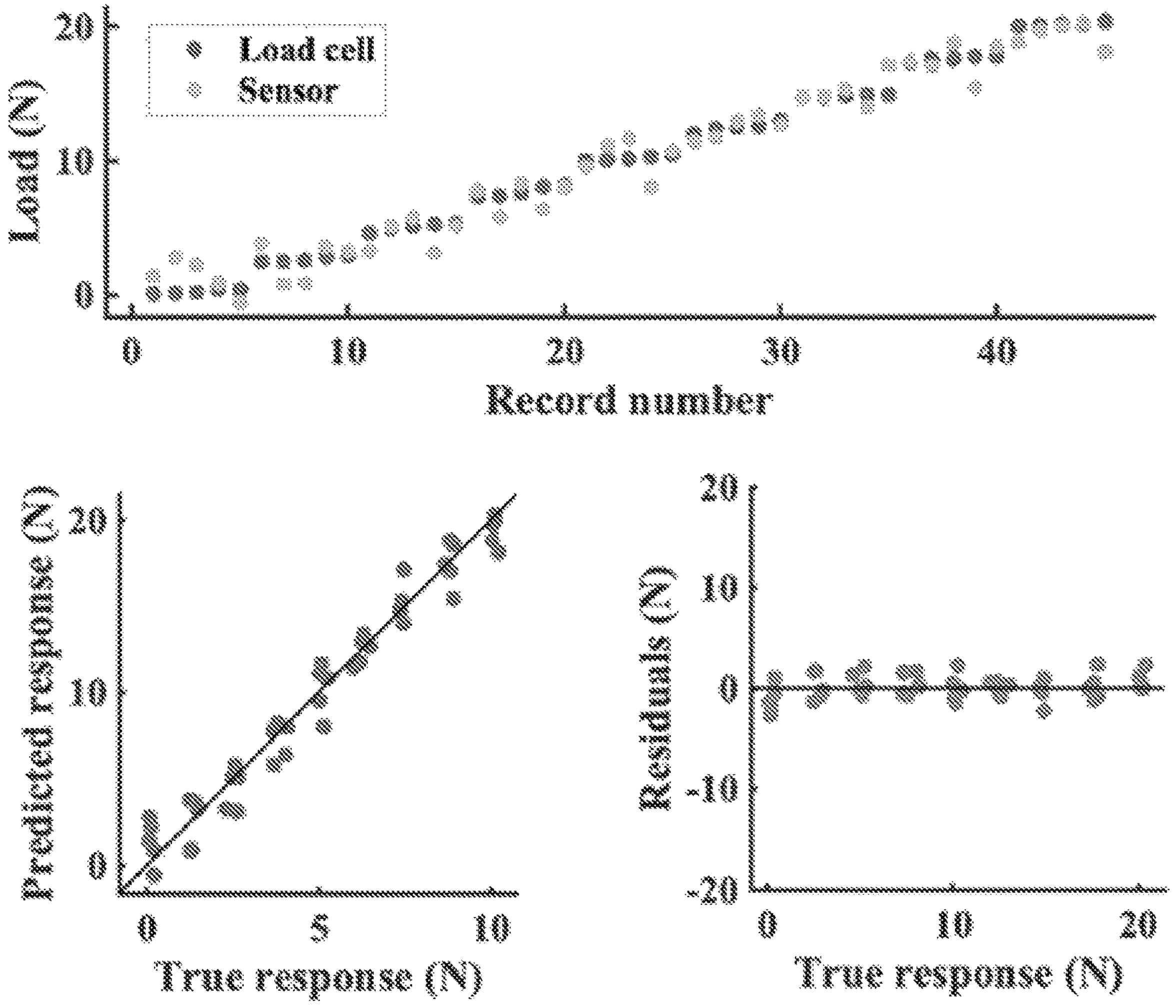
FIGS. 7A-7B are graphs of performance of a sensor example compared to the load cell, measuring horizonal (FIG. 7A) and vertical (FIG. 7B) shear stresses.
Figure 7B:
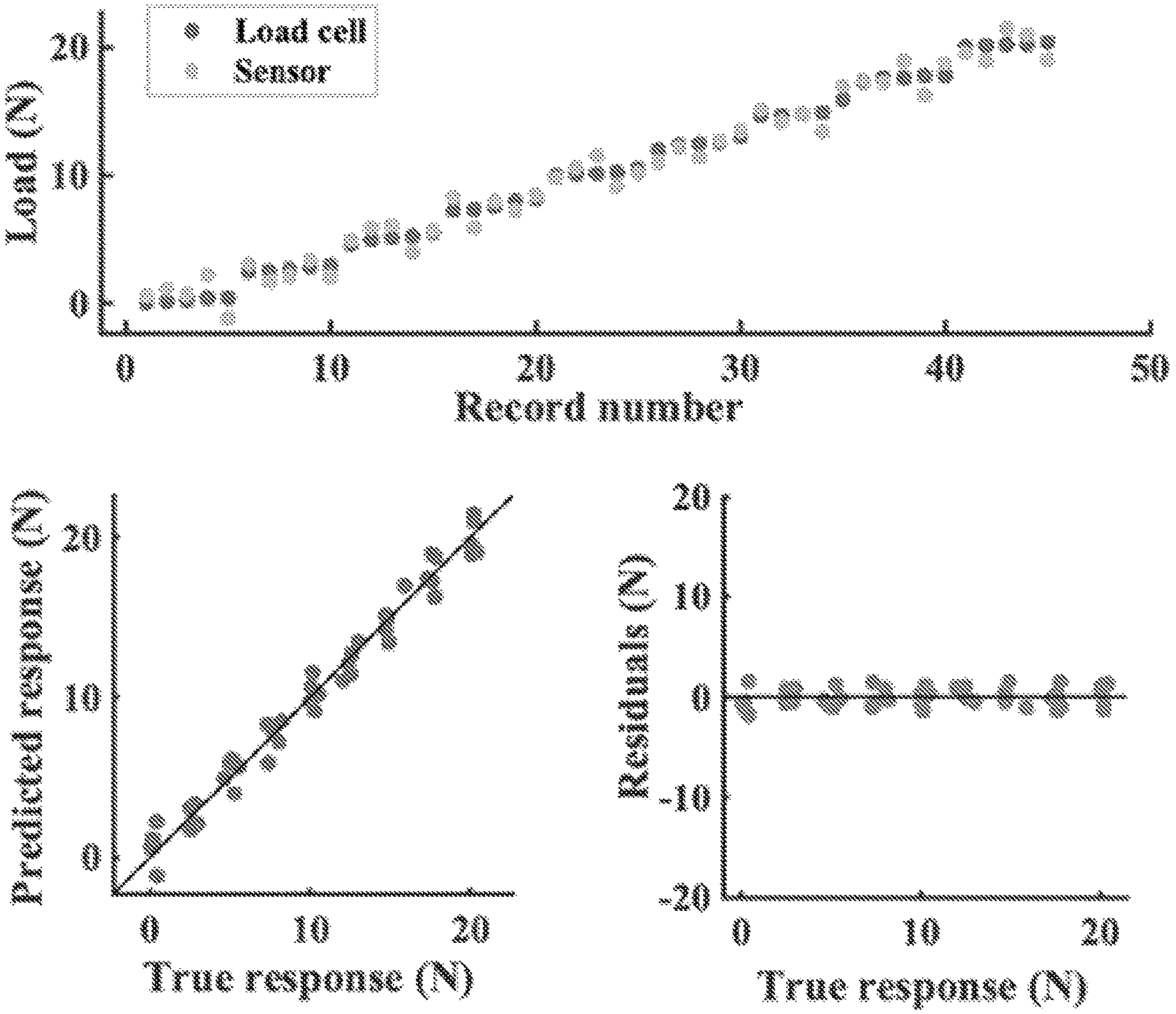

To characterize the sensor's performance for measuring shear stress, a 3 mm-thick optically-clear PDMS elastomer layer was adhered between surfaces 514, 516. The sensor was then placed in the materials testing system using the methods described above. The materials testing system was actuated for loads ranging 0-20 N in 2.5 N increments, measured via a load cell (1516FQG-100, TA Instruments, New Castle, DE) placed in series with the actuator, with related results disclosed in FIGS. 7A-7B. Red, green, and blue color intensity was measured as a resistance at the photodiode during each static load increment. Each LED color was cycled 10 times at 50 Hz and the average resistance was recorded for each color. To measure the repeatability of the sensor, 5 trials were completed and inter-trial variability was calculated. Sensor-derived measurements of shear stress were then compared to data from the load cell. Hysteresis of the sensor was also characterized. All data were collected in dark conditions to avoid interference from ambient light sources.

Displacement data measured from the HADS (accuracy: ±0.0001 mm) and load data from the in-series load cell (accuracy: ±0.0001 N) were used as reference standard comparator values to model and characterize the sensor's performance. The ratio $R_r/R_g$ was used to for sensing displacement/shear stress changes in the vertical direction, whereas $R_b/R_g$ was used for sensing horizonal changes. For both displacement and shear stress, a model fit was derived for the sensor's response (i.e., light intensity) compared to the reference standard value.

Gaussian Process (GP) regression was used to model the sensor response for both the displacement and shear stress conditions (e.g., Mathworks, Natick, MA). Compared to traditional regression models, GPs can be advantageous for characterizing sensor performance because they can directly capture model uncertainty in addition to predicted values. Further, a priori knowledge and specifications can be added about the shape and behavior of the model by selecting different kernel functions (e.g., linear vs exponential). Five rounds of cross-validation were performed using randomized data partitions. The validation results were averaged across the rounds to provide an overall characterization of the model's predictive performance. Sensor performance was characterized using coefficient of determination ($R^2$), mean absolute error (MAE), and root-mean-squared error (RMSE) values across the full range of conditions tested.

Sensor-derived measurements of horizontal displacement matched HADS values well ($R^2>0.99$, MAE=0.08 mm, RMSE=0.20 mm). The sensor showed similar performance for vertical displacement ($R^2>0.99$, MAE=0.07 mm, RMSE=0.16 mm) (FIG. 4). These data serve to demonstrate the baseline performance of the sensor's operating principle of measuring optical coupling between the RGB LED and photodiode based off light reflected from the patterned color surface. Inter-trial variability was <0.02%, indicating that the sensor is capable of making repeatable measurements. Higher residuals (~1 mm) for displacements of 1 mm in both the horizontal and vertical directions indicate that the sensor may not be sensitive to displacements <1 mm. This parameter may be tunable through sensor design modifications such as LED light intensity or use of an amplifier.

The sensor's performance for measuring shear stresses in the horizontal and vertical directions showed greater variability compared to displacement measurements. Nevertheless, sensor-derived measures of horizonal shear stress matched load cell data well ($R^2>0.96$, MAE=0.97 N, RMSE=1.2 N). Performance in the vertical directional was more accurate and exhibited decreased variability compared to the horizonal direction ($R^2>0.98$, MAE=0.91 N, RMSE=0.9 N).

Figure 8:
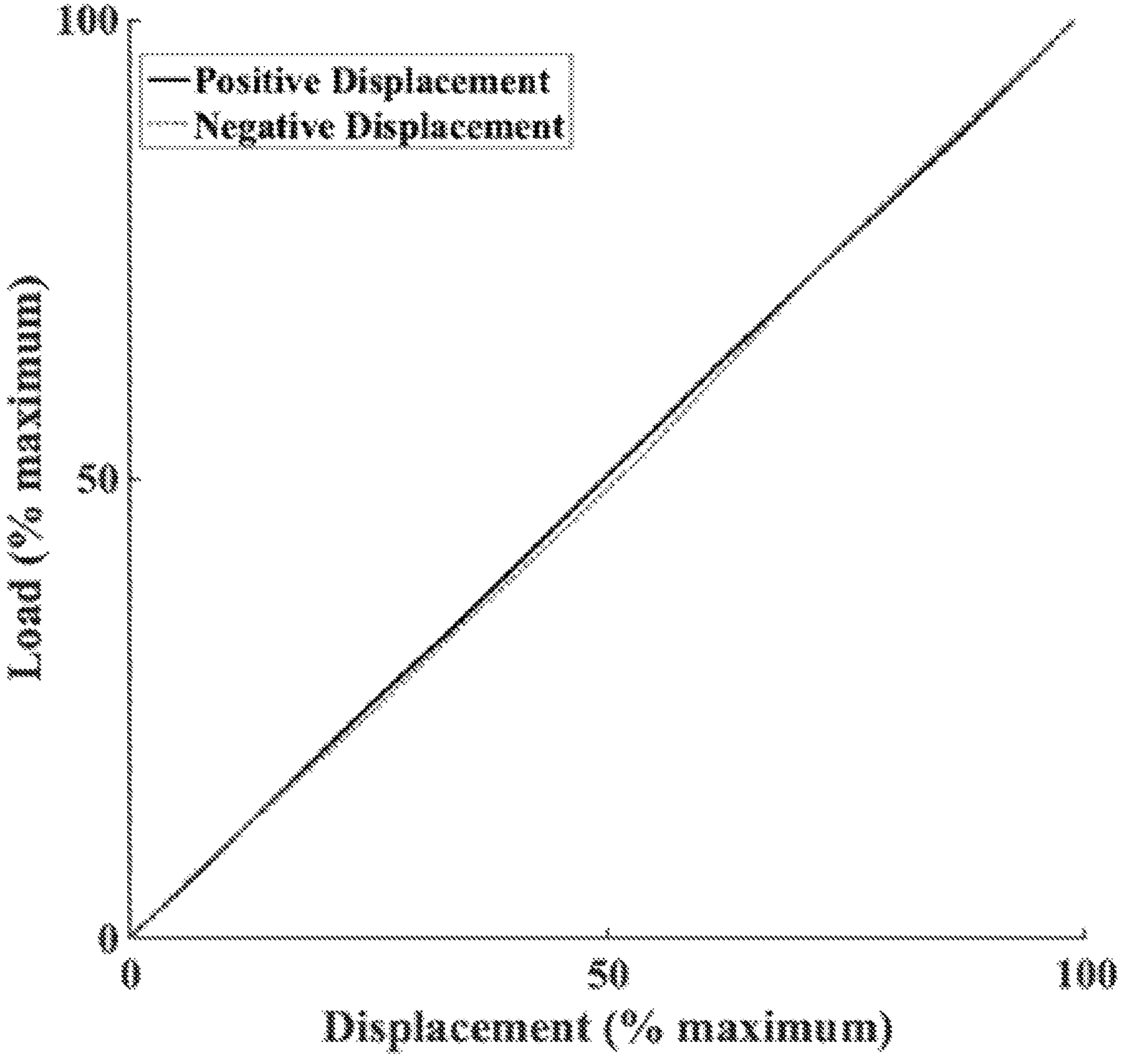
FIG. 8 is a graph of hysteresis response for an example sensor measured via HADS and load cell.

The physical sensor package (i.e., resin housing and PDMS elastomer) showed a linear relationship between load and displacement ($R^2>0.99$) as measured via the load cell and HADS. Hysteresis response, as shown in FIG. 8, was less than 0.1% across the full range of loads and displacements. The relationship between force (F) and displacement (x) was 13.4 N/mm and the PDMS layer has a surface area (A) of 50 $mm^2$. As such, the shear modulus (G) of the sensor's PDMS can be calculated as function of force, displacement, and PDMS area (eq. 1), assuming rigidity of the resin housing:

$$G = \frac{F/x}{A} = \frac{13.4 \text{ N/mm}}{50 \text{ mm}^2} = 268 \text{ kPa} \quad \text{Eq (1)}$$

The calculated modulus of 268 kPa is similar to values reported in previous characterizations of the material properties of PDMS. The modulus of PDMS can also be tuned based on different curing parameters, which allows disclosed sensor examples to be scalable to meet different loading requirements. Values between 0.93 mPa and 450 kPa have been reported.

The linearity, scalability, and resolution in shear stress measurements derived from this sensor support its use for in robotics, medical, and orthopedic applications. High linearity is advantageous, as it can potentially allow for simplified sensor calibration and minimal signal conditioning requirements for signal processing. The scalability is also advantageous, as many previous shear sensor designs were limited in their applications due to low sensing range. High sensor resolution is important for a variety of uses. For example, sensor feedback could be used to allow a grasping robot to handle a fragile object by providing the necessary grip force to manipulate the object without breaking it. In medicine, pressure of <8 kPa can cause tissue ischemia, thus necessitating high resolution for sensors tasked with identifying these conditions. Shear stress has been shown to be at least equivalent to pressure as an external factor leading to tissue breakdown, and thus, high resolution for shear measurements from this sensor show promise for providing early indication of tissue breakdown.

Data show differentiation between horizonal and vertical shear stresses and show that the sensor performs equally well in both dimensions. This quality is especially advantageous compared to previous work in optical-based shear sensors which were only capable of sensing resultant shear stress. The ability to measure multi-axial shear stresses has typically been limited to use of strain gauges. Compared to this sensor, strain gauges are often larger (e.g., 47 mm), heavier (e.g., 375 g), require greater power, and necessitate being tethered by cables.

Figure 9A:
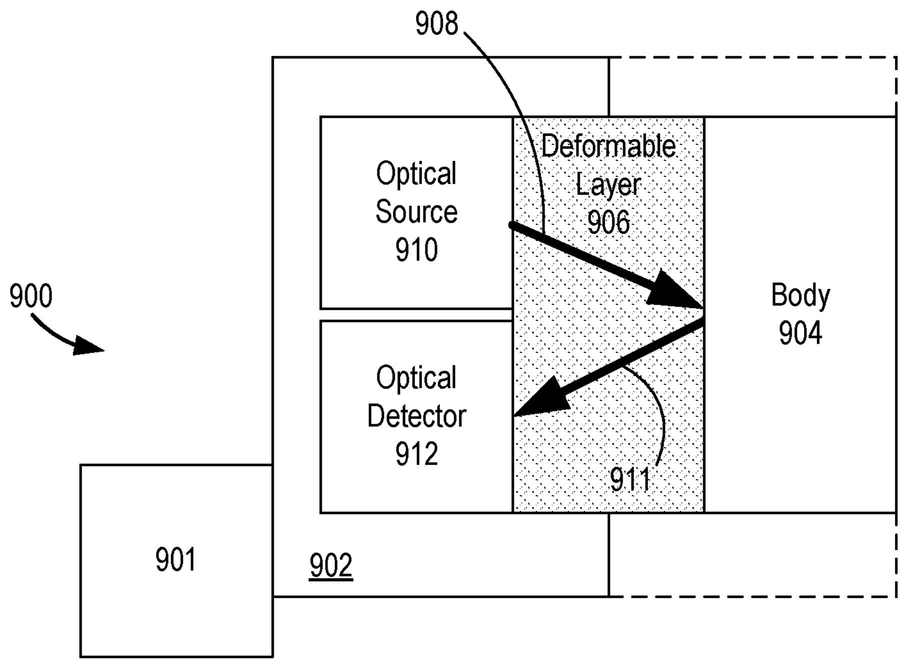
FIGS. 9A-9B shows a schematic series of a sensor under no load and a deformable load.
Figure 9B:
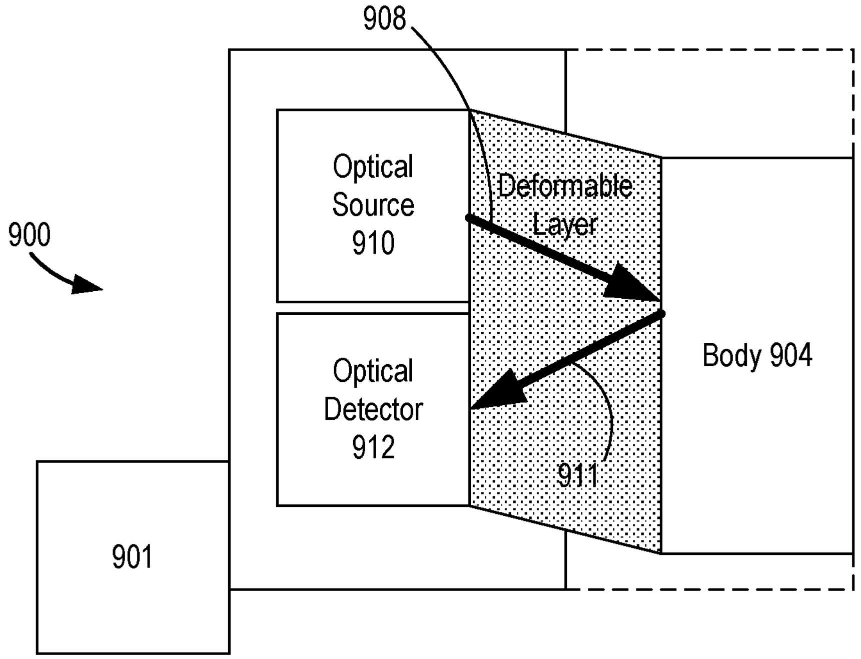

FIGS. 9A-9B depicts shearing in an example shear sensor 900 attached to a primary shearing body 901. The sensor 900 shears between a sensor housing 902 and a body 904 having a spatially variable reflectance pattern affixed thereon, using the deformability of an intermediate deformable layer 906. The deformation of the layer 906 provides a relative displacement between the sensor housing 902 and body 904. An optical probe beam 908 emitted from an optical source 910 supported by the housing 902 can be directed to the body 904 and reflected back 911 to an optical detector 912 also supported by the housing 902. As the body 904 is displaced, the pattern on the body 904 displaces as the probe beam 908 continues to be directed in the same direction. The resulting light 911 detected by the optical detector varies according to the spatially variable reflectance pattern on the body 904.

Figure 10:
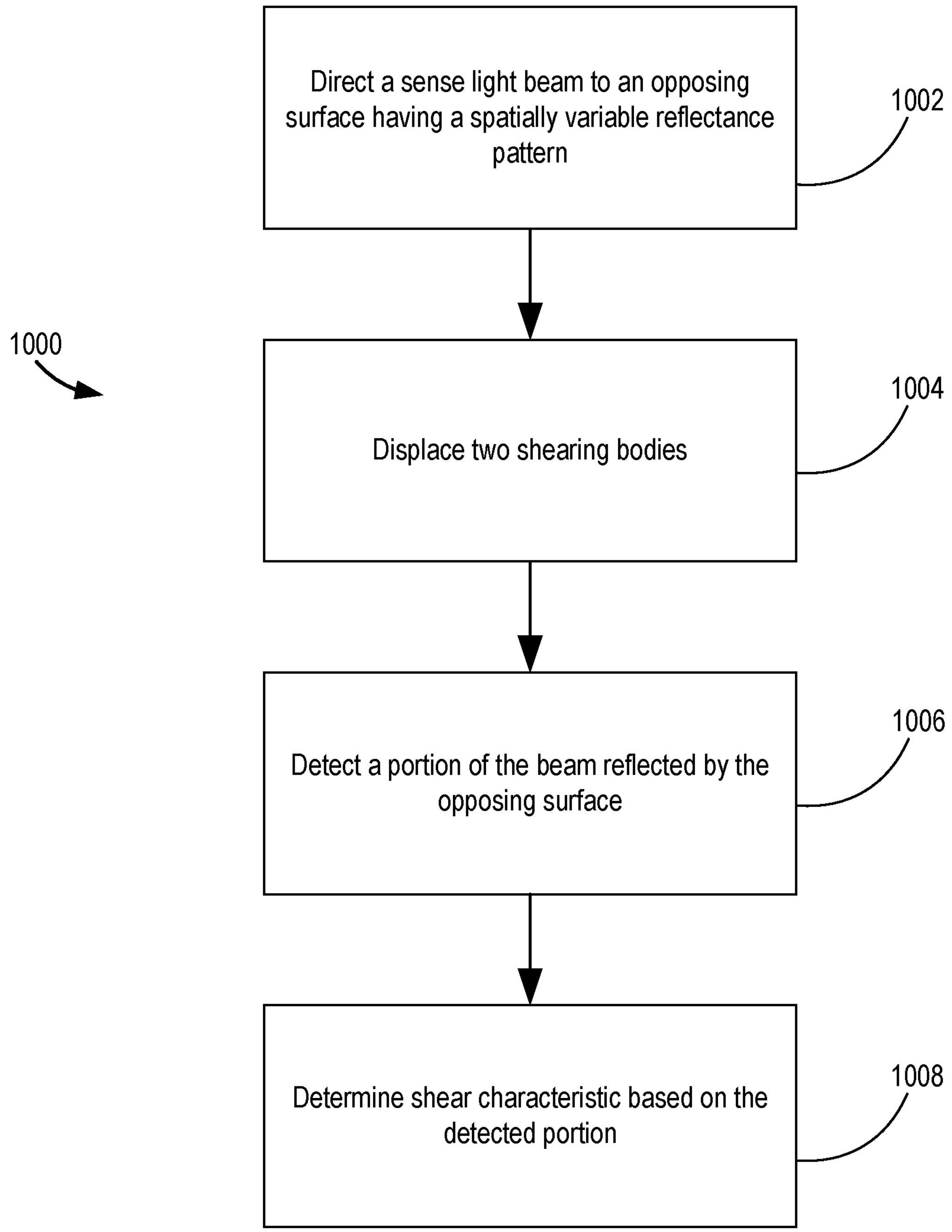
FIG. 10 is a flowchart of an example method of measuring shear characteristics of two shearing bodies.

FIG. 10 shows an example method 1000 of determining a shear characteristic between two shearing bodies. At 1002 a light beam is directed to an opposing surface having a spatially variable reflectance pattern. At 1004, the two shearing bodies are displaced with a shearing force. At 1006, a portion of the beam reflected by the opposing surface is detected, producing an output signal that has changed due to the displacement. At 1008, a shear characteristic, such as a shear stress, strain, or displacement, is determined based on the detected portion of reflected light.

Figure 11A:
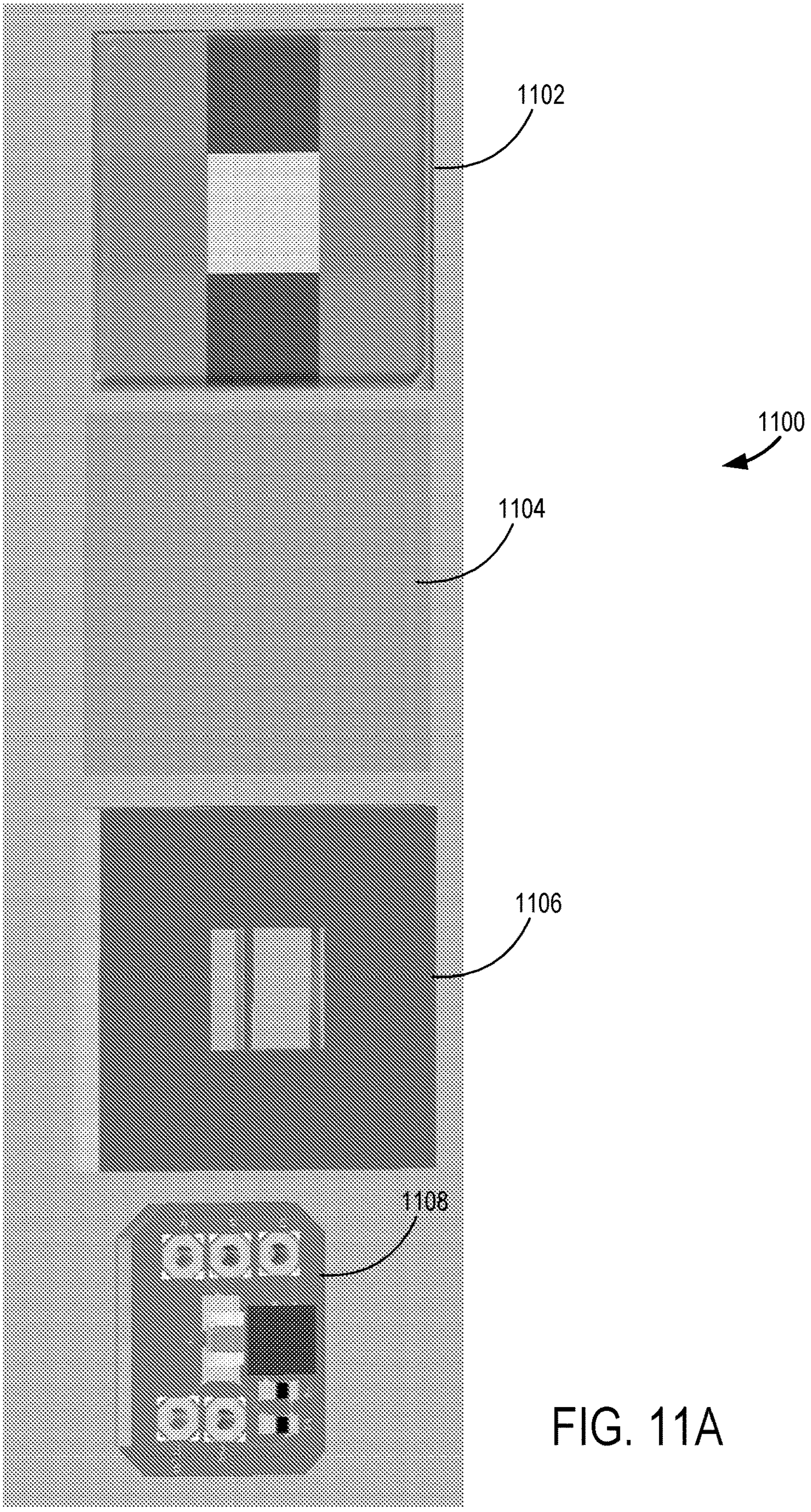
FIGS. 11A-11B are perspective views of an example shear stress sensor.
Figure 11B:
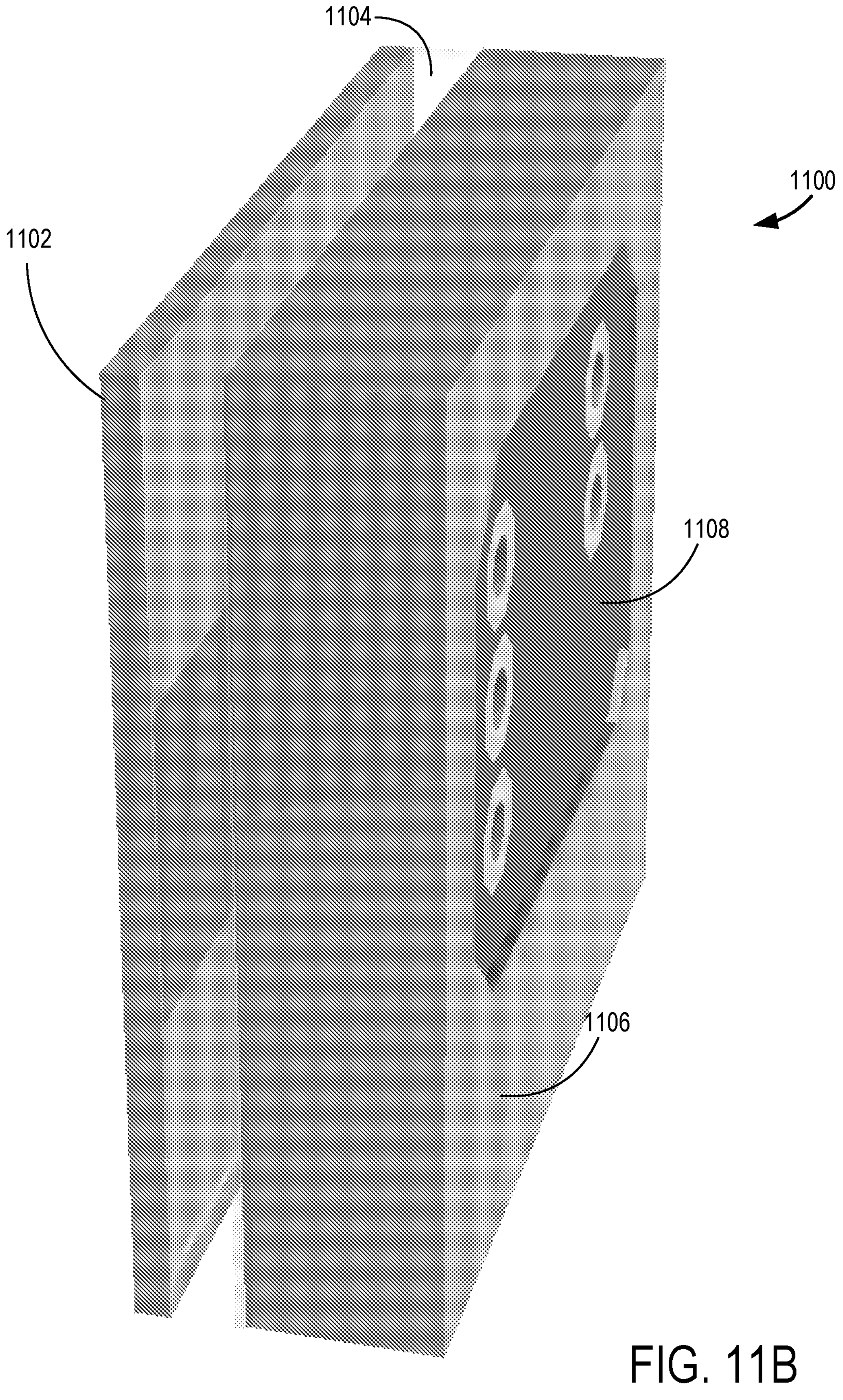
Figure 12A:
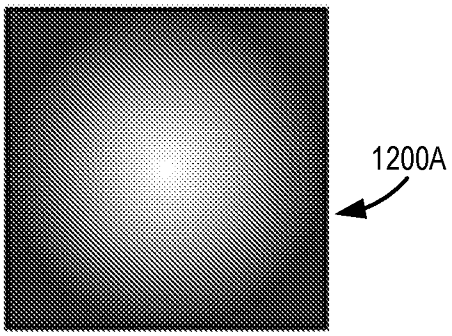
FIGS. 12A-12E are gradient-based gray-scale spatially variable reflectance patterns.
Figure 12B:
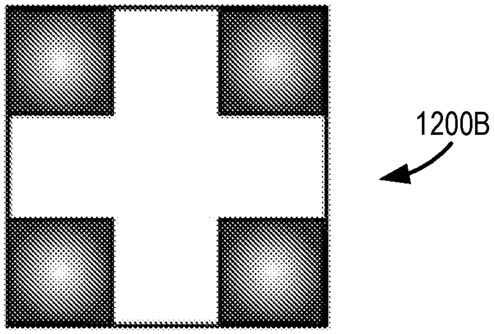
Figure 12C:
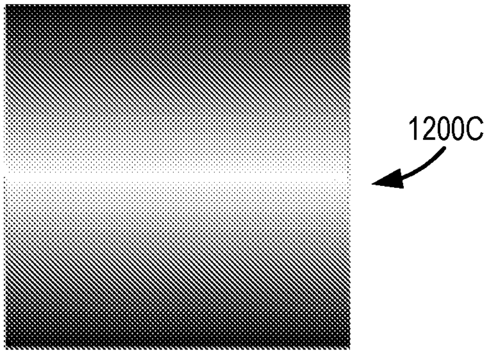
Figure 12D:
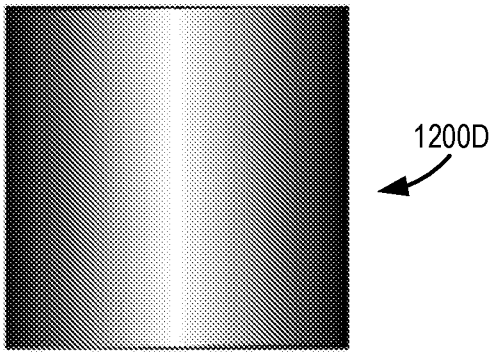
Figure 12E:
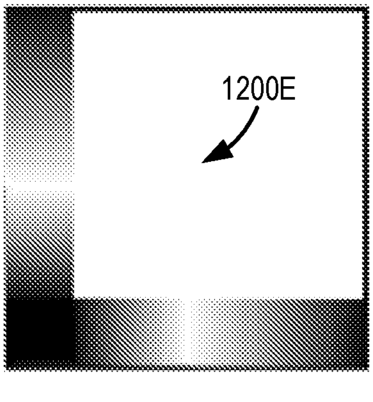
Figure 13A:
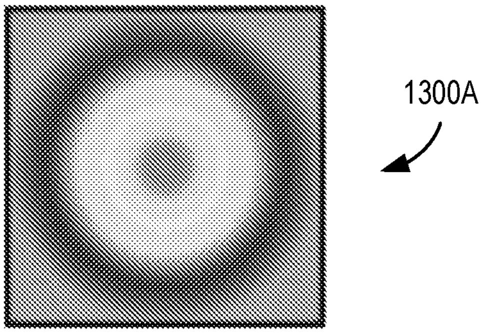
FIGS. 13A-13E are gradient-based color spatially variable reflectance patterns.
Figure 13B:
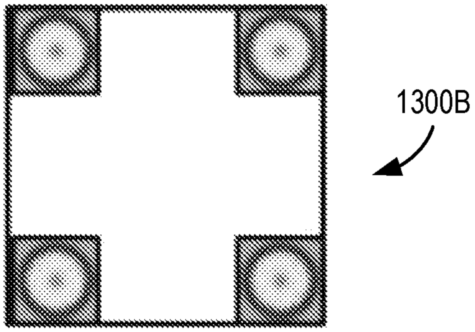
Figure 13C:
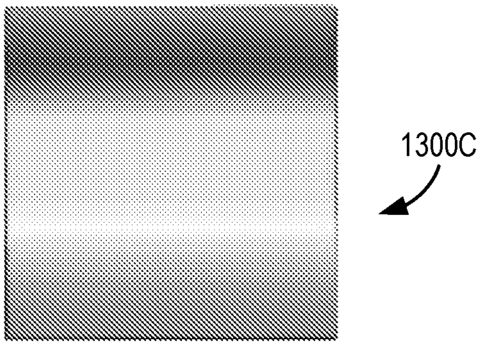
Figure 13D:
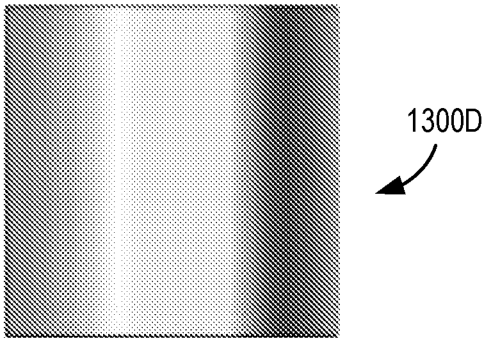
Figure 13E:
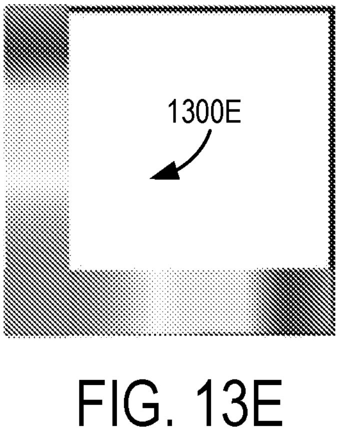

FIGS. 11A-11B shows an example of a compact shear sensor 1100. The parts of the sensor 1100 include a base plate 1102 having a colored pattern, a transparent PDMS layer 1104, a sensor housing 1106 having a window, and a printed circuit board 1108 having a light source, light detector, and various arranged electrical components.

FIGS. 12A-12E shows five different gradient-based gray-scale patterns 1200A-1200E that can provide spatially varying reflectances. The pattern 1200A includes a radially symmetric gray-scale variation that can be used in some shear sensors. A white LED can be used with a photodiode to measure reflectance changes associated with shear displacement and stress/strain. The pattern 1200B includes a plurality of sub-patterns that can also each include radially symmetric gray-scale variations. In some examples, a plurality of photodiodes can be coupled each to a respective sub-pattern and a torsional measurement can be obtained based on the different detected variations in reflectance associated with a torsional displacement and stress. The patterns 1200C, 1200D show gradients in vertical and horizontal directions, respectively. In some examples, separate photodiodes can be coupled to respective vertical and horizontal patterns to produce linear displacement measurements based on detected reflectance variations. Pattern 1200E includes two perpendicular gradient variations that can be used to measure shear stress along perpendicular axes.

FIGS. 13A-13E shows five different gradient-based color patterns 1300A-1300E that can provide spatially varying reflectances. The color patterns 1300A-1300E include spectrally-based spatial variations, e.g., with a red center in pattern 1300A or in sub-patterns in pattern 1300B that vary to shorter wavelengths with increasing radial distance from the centers. Patterns 1300C, 1300D show similar spectral-spatial variations, from bottom to top (or vice versa) in pattern 1300C and from left to right (or vice versa) in pattern 1300D. Pattern 1300E includes two perpendicular gradient spectral-spatial variations, with red in a bottom left corner and decreasing in color wavelength with increasing vertical and increasing horizontal positions.

Figure 14:
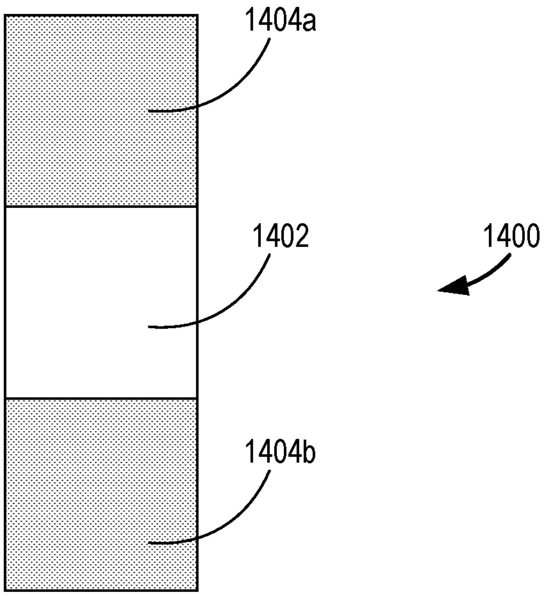
FIG. 14 is an example linear gray-scale pattern.
Figure 15:
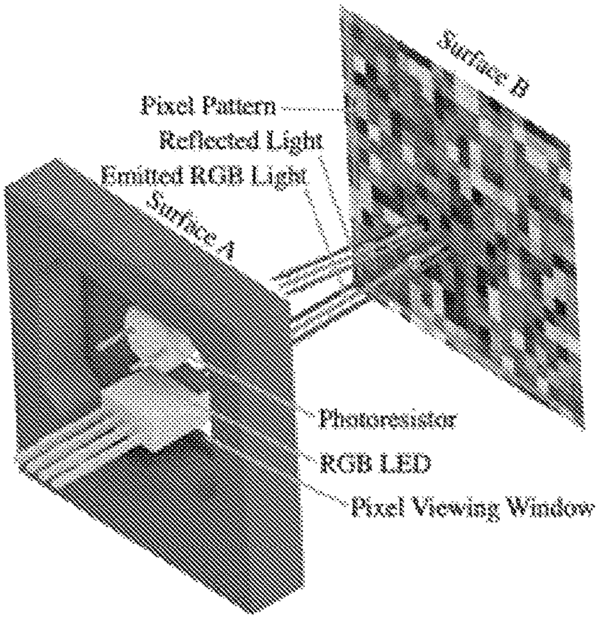
FIG. 15 is a perspective view of a sensor having a reflective surface with a randomized pixel pattern.

FIG. 14 is an example gray-scale pattern 1400 including a central square 1402 and opposite squares 1404*a*, 1404*b*. The central square 1402 is a selected gray-scale color, such as white, black, or an intermediate shade of gray. The opposite squares 1404*a*, 1404*b* are typically a common gray-scale color different from the gray-scale color of the central square 1402. The pattern 1400 can also be repeated in the linear direction shown or can be extended two-dimensionally, e.g., in both vertical and horizontal directions. In some examples, a separate optical detectors are coupled to different linear pattern arrangements and optically isolated from each other. In further examples, a common optical detector can be used, e.g., with an optical source arranged to illuminate the different linear patterns at different times and the linear pattern arrangements aligned with separate aperture windows.

Examples Using Data Classification

As discussed above, disclosed sensor examples can measure bi-axial shear strain based on optical coupling between a red, green, and blue (RGB) light-emitting diode (LED) and a Cadmium Sulfide (CdS) photoresistor. Examples can cycle red, green, and blue light, which is reflected off an adjacent surface with a specific color or gradient pattern (e.g., a 3×3 grid of red, green, blue, and magenta color squares). Shear displacement of the adjacent surface provides a different combination of color pixels to absorb and/or reflect RGB lights, allowing the photoresistor to measure displacement, and thereby shear strain, as relative changes in RGB light intensities are detected. For example, shear strain can be detected by measuring the relative content of red, green, and blue color displayed in a window.

Examples advantageously can measure shear dynamics, e.g., in devices having a small (15 mm×15 mm), lightweight (~1 g), and relatively low power requirements (~10 mA). Example sensors demonstrate good linearity and resolution, which can be particularly applicable to sensing in biomedical and robotics applications. Examples can allow differentiation of shearing along two axes, in contrast with existing other sensors that only measure resultant shear (i.e., sum of all shear strain). Disclosed sensor examples can be highly scalable with rapid fabrication techniques (3D printing and printable circuit boards (PCBs)).

Disclosed examples can further include non-symmetrical pixel patterns, which can allow discrimination between positive vs. negative shearing along a particular axis. In some examples, asymmetric randomized pixel patterns can provide improved or comparable signal resolution while allowing discrimination of shear strains in positive vs. negative directions. Various reflective color patterns can be used and can have different efficacies in measuring shear strain. Various data classification algorithms (e.g., model fitting vs. nearest neighbor classification) can be used to model the sensor output. Randomized color pixel patterns can produce highly accurate shear measurements. While various classification techniques may be used, selected examples using K-nearest-neighbor (KNN) algorithms were found to provide highly accurate classification of sensor data using a randomized pattern.

Figure 16A:
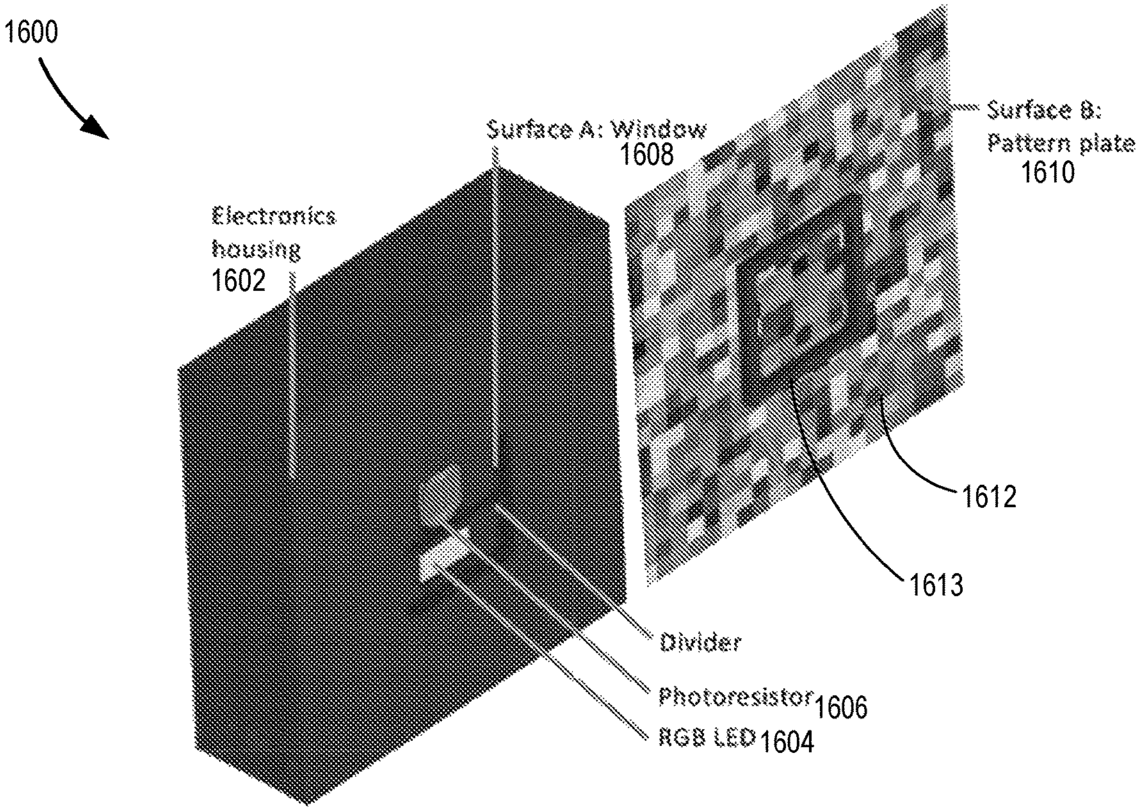
FIG. 16A is a perspective view of a disassembled sensor where opposing surfaces are rotated away from each other to show design features
Figure 16B:
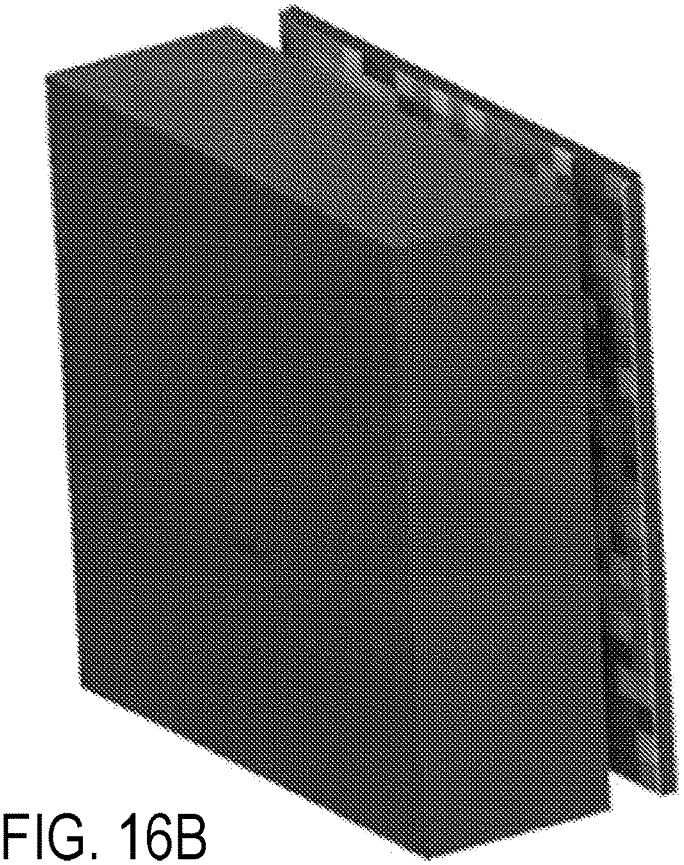
FIG. 16B is a perspective view of the sensor where the opposing surfaces are rotated back to an operational configuration.
Figure 16C:
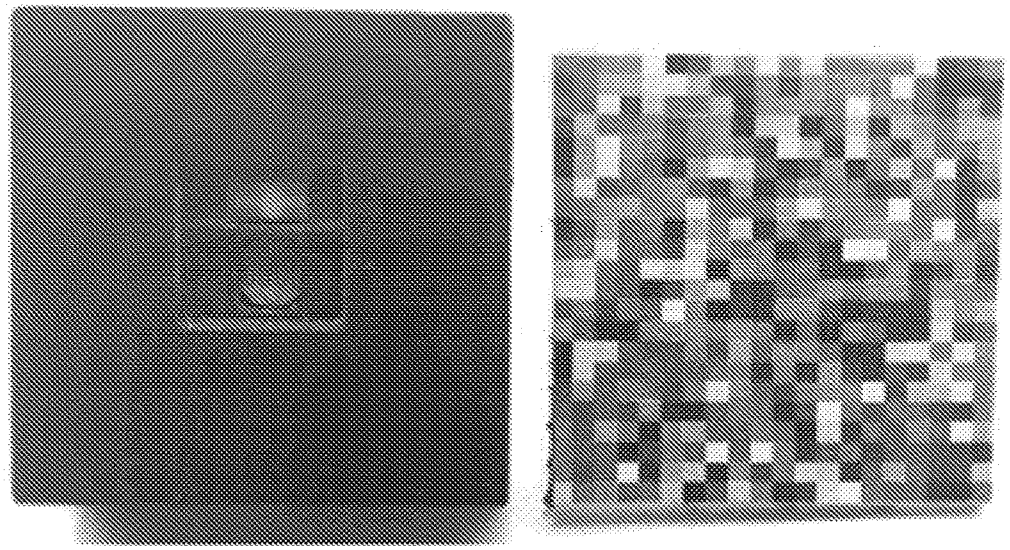
FIG. 16C is a perspective end view of the disassembled sensor similar to the disassembly shown in FIG. 16A.-16C are a disassembled sensor with salient design features labeled.
Figure 17A:
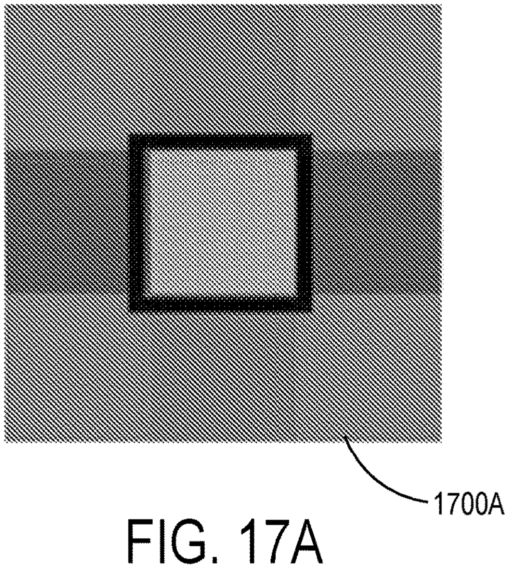
FIGS. 17A-17G are seven color patterns used for a Surface B, each including a projection of a black window associated with an optically coupled adjacent Surface A.
Figure 17B:
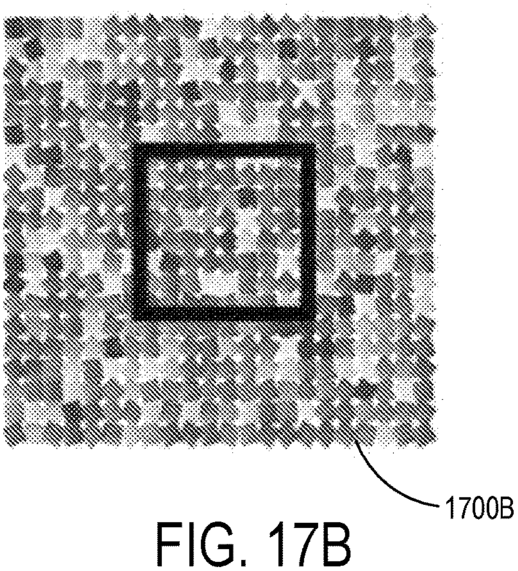
Figure 17C:
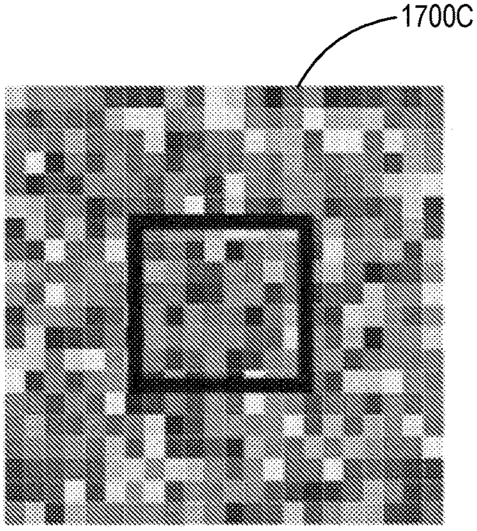
Figure 17D:
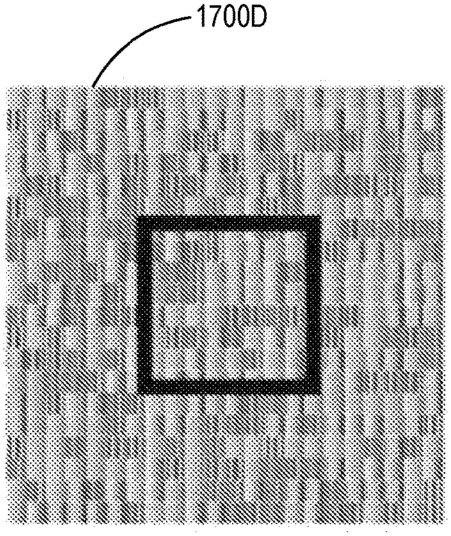
Figure 17E:
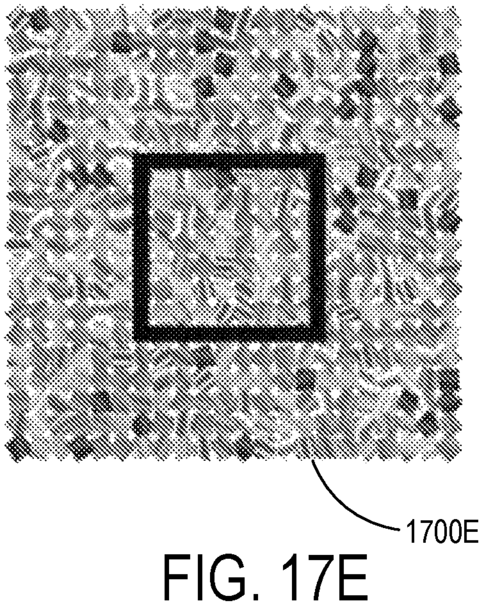
Figure 17F:
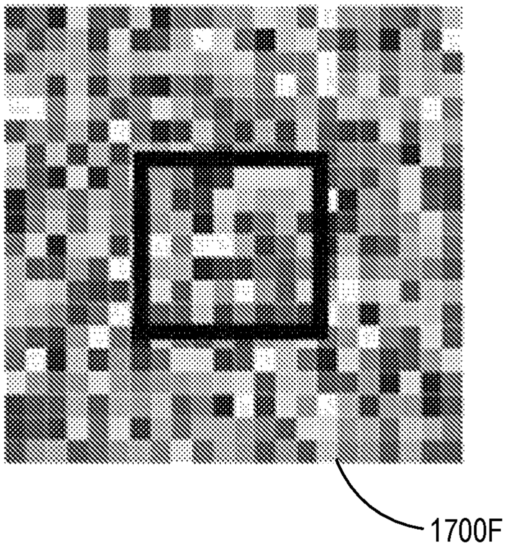
Figure 17G:
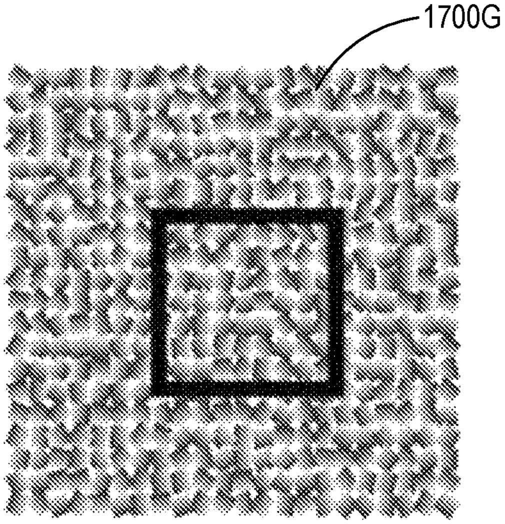

As illustrated in FIGS. 16A-16C, an example sensor 1600 includes an instrumented housing 1602 configured to house an LED 1604 and photoresistor 1606, a black trim window 1608 (FIG. 16A) defining a Surface A, and an adjacent plate 1610 displaying a color pattern 1612 (FIG. 16B) and defining a Surface B. A projection 1613 of the window 1608 is shown on the adjacent plate 1610 illustrating a subset of pixels of the color pattern 1612 viewable by the photoresistor 1606. Various sensor examples can include different separation of parts, e.g., with Surface A and Surface B in a common sensor unit, or with Surface A and Surface B separated from each other, such as with the Surface B as a separate component that is not attached to Surface A.

In a particular example, the sensor packaging is 30 mm×30 mm×5 mm (thickness). The LED 1604 (Adafruit 2739, Adafruit Industries, New York, NY) emits red, green, and blue light at 632, 520, and 468 nm, respectively. At 20 mA, the brightness for these colors is 350, 800, and 250 millicandela (mcd). The photoresistor 1606 (Adafruit 161) is sensitive to wavelengths ranging 400-800 nm, inclusive of the red, green, and blue color spectra. The LED 1604 and photoresistor 1606 are housed in a 3D printed methylacrylate photopolymer resin (Formlabs, Somerville, MA) forming the housing 1602. Within the housing 1602, the LED 1604 and photoresistor 1606 are isolated such that the photoresistor 1606 is only exposed to light reflected from the Surface B, e.g., by blocking light directly emitted from the LED 1604 and/or through calibration to remove signal amounts associated with stray light. Surface B is arranged on the plate 1610 (3D printed) and displaying color pattern 1612.

During operation, the alignment of the window 1608 on Surface A with the pattern on Surface B produces a variable amount of reflected light depending on the reflectance (absorbance) characteristics of the pattern. For example, the window 1608 on Surface A (10 mm×10 mm) presents a limited set of pixels of Surface B that reflect light to the photoresistor 1606. Also, red, green, and blue light are reflected or absorbed differently depending on the color pixels present. Therefore, the set of viewable pixels may be classified by their unique properties for reflecting or absorbing RGB light, as measured by the photoresistor. Under resting (or zero-strain) conditions a certain set of color pixels is present. Shearing of Surface A with respect to Surface B presents a view of a different set of pixels (e.g., the projection 1613 shifts to cover a different area) that can have unique reflectance/absorbance properties for RGB light.

In the particular example discussed above, the LED 1604 and photoresistor 1606 were controlled using an Arduino 2560 analog-to-digital converter (ADC) and microcontroller. The emitted color of the LED 1604 was controlled using a custom MATLAB script (Mathworks Inc., Natick, MA), which controls individual power between the red, green, and blue cathode leads and a common anode. The photo-resistor 1606 acts as a variable resistor in response to light intensity. To measure resistance of the photoresistor 1606, a 100 kOhm resistor was connected in series. This allows variation in the photoresistor's resistance to be measured as changes in voltage across the photoresistor. However, it will be appreciated that various approaches may be used to measure reflected light. Photoresistor data were sampled via the microcontroller's analog input pins and recorded using the MATLAB script.

FIGS. 17A-17G shows seven example color (including gray-scale) patterns 1700A-1700G that can be used with disclosed sensor examples. The patterns include different pattern characteristics including pixel color, gray scale, randomization, and gradients that can affect shear strain measurements using disclosed sensor examples. Relative performance of the patterns 1700A-1700G was compared by having pattern examples with a common area matching the dimensions of the sensor (30 mm×30 mm). Each of patterns 1700B-1700G contains a respective 20×20 array of 1.5 mm×1.5 mm randomly distributed color pixels. Pattern 1700A contains a 3×3 array of 10 mm×10 mm red, green, blue, and magenta (red and blue) pixels, which is similar to the colored grid pattern 402 discussed hereinabove. The patterns 1700A-1700E included color pixels, whereas patterns 1700F, 1700G are gray-scale. The pixels in patterns 1700A, 1700C, 1700D, 1700F are aligned with vertical and horizontal axes, whereas those in patterns 1700B, 1700E, 1700G have a randomly assigned rotation between 0 and 179°. The patterns 1700B, 1700D, 1700E, 1700G contain pixels with gradients of color, whereas patterns 1700A, 1700C, 1700F include pixels of solid colors. The variations among the patterns 1700A-1700G allowed comparisons between different pattern characteristics (e.g., color vs. gray scale, solid vs. gradient, randomized vs. patterned). Pixel distributions, and rotations where applicable, were randomly assigned for each pixel using a custom JavaScript. The color patterns were printed on an adhesive-backed vinyl with a matte finish (Strathmore Inc., 59-635). It will be appreciated that patterns 1700A-1700G are merely illustrative and do not represent an exhaustive list of possible pixel patterns that may be used in disclosed sensor examples.

Figure 18:
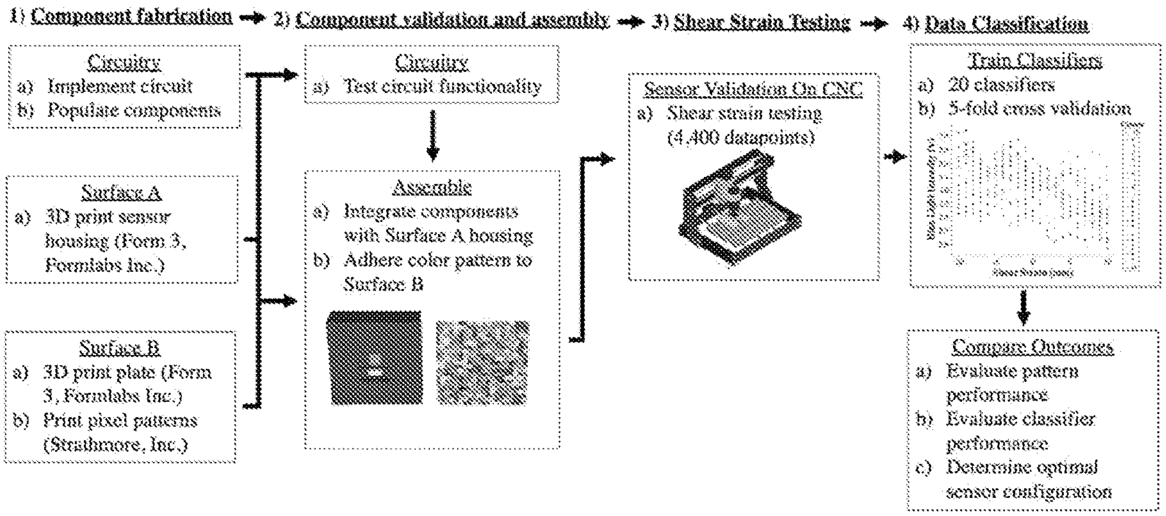
FIG. 18 is a flow diagram of sensor fabrication and data classification processes.

In an experimental trial, sensor response to shear strain of each color pattern 1700A-1700G was measured based on reflected RGB light as discussed in various examples herein. An overview of the experimental methods used to fabricate, test, and compare each pattern configuration is shown in FIG. 18. As depicted with the test arrangement 1900 in FIG. 19, to apply controlled test displacements and thereby shear strains, a 3D printed housing 1902 secured the test sensor in a modified computed numeric control (CNC) router. A second 3D printed housing 1904 displaying a tested color pattern was affixed in a CNC spindle bracket to allow controlled strain between sensor Surfaces A and B. The CNC's stepper motors allow for controlled strains with an accuracy of ±0.01 mm.

Figure 19:
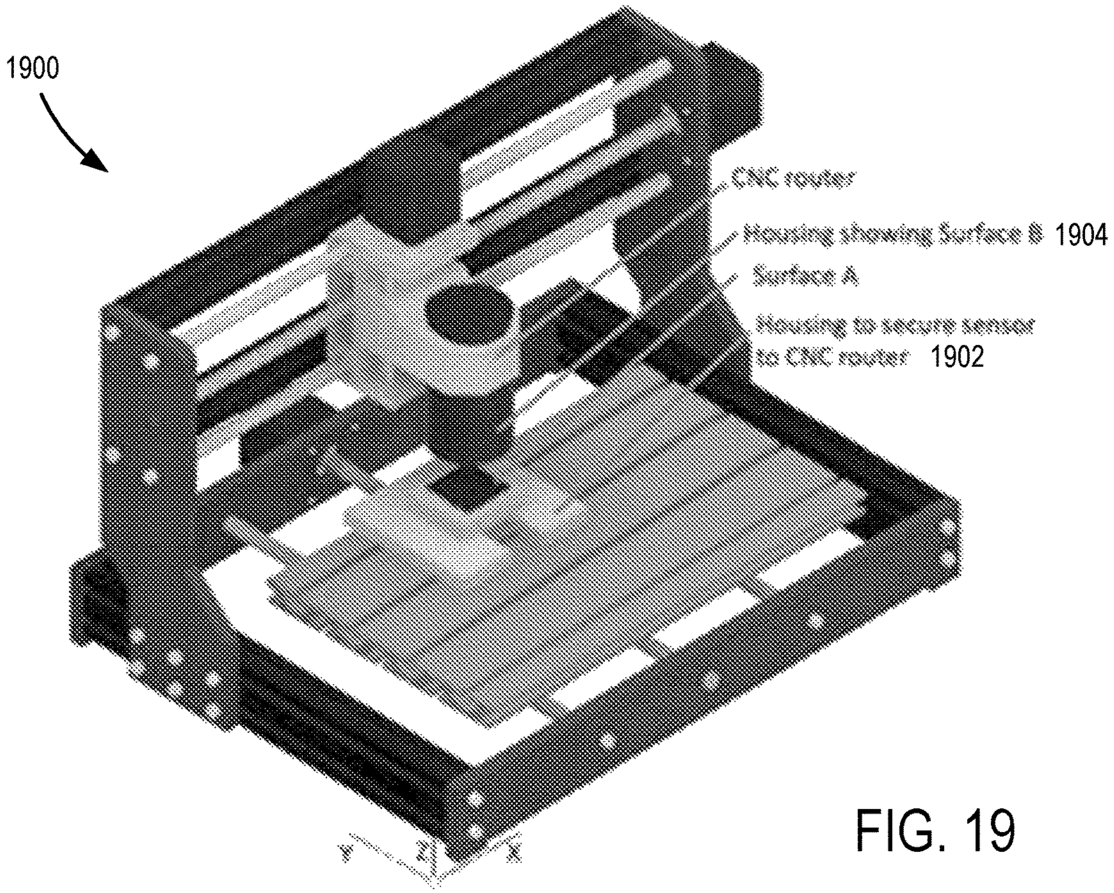
FIG. 19 is an illustration of testing apparatus including a CNC router, opposing Surfaces A and B, and a gap therebetween.

For each characterization trial, one of the color patterns 1700A-1700G was adhered to the housing 1904 attached the spindle (FIG. 19). A photoresistor of the test sensor is sensitive to light in the 400-800 nm spectrum, which includes environmental light and many indoor lighting sources. To minimize confounding effects from ambient light, the spindle was lowered until Surface A made contact with Surface B. In this configuration, the distance between the LED and photoresistor and the color pattern is 1.5 mm. Surface B was then displaced with respect to the instrumented side of the sensor (Surface A) in 1 mm increments for a range of ±10 mm in the X and Y planes (parallel to the surface plane of the sensor), as illustrated in FIG. 18. At each 1 mm position, a static measurement of RGB color intensity was recorded by cycling each LED color at 50 Hz and recording voltage at the photoresistor during red, green, and blue color illumination. To characterize the repeatability of these measurements, this process was repeated 10 times at each position. In total, the surface of each color pattern 1700A-1700G was mapped at 440 locations (4400 data points). These methods were repeated for each color pattern, and the order of color pattern was randomized.

Highly accurate displacement data from the CNC router (accuracy: ±0.01 mm) were used as gold standard comparator values to model and characterize the test sensor's performance. Displacement data were stratified into 1 mm classes, totaling f21 output classes in the X and Y directions (40 total classes). The twenty-two independent data classification models were trained for each pattern. The model type (also referred to as a classifier) and associated results are shown in Table 1. For each model, three variables were used as inputs: raw photoresistor data (volts) during red, green, and blue illumination. The ability of these inputs to classify shear strain was evaluated. All models were trained with a gradient-based penalty for misclassification whereby an accurate classification is associated with a penalty of zero and the model receives an incremental penalty of 1 for each millimeter of error (e.g., misclassification by three millimeters receives of penalty of three).

The 22 classification models generally can be organized into six main categories: Decision tree, Discriminant analysis, Naïve Bayes, Support vector machine (SVM), Nearest neighbor, and Ensemble. The strengths of decision tree classification algorithms are their relative simplicity and thus high computational speed and low memory usage. However, they can have low accuracy for complex datasets. Discriminant analysis-based classifiers assume that different classes generate data based on varying Gaussian distributions. They typically offer good computational speed and high accuracy for widely-varying datasets. Naïve Bayes classifiers are useful in multi-class classification scenarios. The algorithm leverages Bayes theorem and makes the assumption that predictors are independent based on class. Support vector machines construct a hyperplane, or a set of hyperplanes that best separate data into two or more classes. They offer good computational speed and accuracy for binary datasets but may lose speed and accuracy when more classes are present. Nearest neighbor algorithms use a variety of functions (e.g., weighting, cosine, etc.) to discriminate between classes. They are typically associated with low computational speed and high accuracy for low-dimensional data, but accuracy may deteriorate with higher-dimension data. Ensemble classifiers combine results from many weak algorithms into a higher quality ensemble model.

TABLE 1

Accuracy and misclassification cost of individual color pattern and classification model conditions. The highest accuracy and lowest misclassification cost conditions are highlighted for each pattern.

| Model | Pattern 1 | | Pattern 2 | | Pattern 3 | | Pattern 4 | |
|---|---|---|---|---|---|---|---|---|
| | Accuracy (%, X/Y) | MC (mm, X/Y) | Accuracy (%, X, Y) | MC (mm, X/Y) | Accuracy (%, X/Y) | MC (mm, X/Y) | Accuracy (%, X/Y) | MC (mm, X/Y) |
| Fine Tree | 59.7/60.9 | 0.35/0.45 | 28.0/50.4 | 3.28/0.49 | 41.2/54.1 | 2.83/1.59 | 41.0/33.9 | 1.92/2.63 |
| Medium Tree | 48.0/42.4 | 0.50/0.86 | 12.2/27.1 | 4.20/2.96 | 20.4/29.2 | 3.79/2.42 | 19.0/16.7 | 2.64/3.60 |
| Coarse Tree | 32.3/16.3 | 0.81/1.48 | 7.51/16.4 | 4.39/3.85 | 11.8/16.2 | 4.35/3.08 | 12.1/8.10 | 2.91/4.33 |
| Linear Discriminant | 21.9/14.3 | 1.15/1.37 | 8.22/22.2 | 4.50/2.73 | 13.1/21.3 | 4.09/2.57 | 15.8/9.42 | 2.52/4.03 |
| Quadratic Discriminant | 35.7/24.5 | 0.95/1.51 | 10.8/33.1 | 4.51/2.55 | 16.5/32.3 | 3.78/2.17 | 24.7/13.6 | 2.29/3.62 |
| Gaussian Naïve Bayes | 24.6/20.3 | 1.47/1.46 | 9.74/26.0 | 4.65/2.86 | 14.2/27.3 | 3.86/2.67 | 19.9/8.40 | 2.50/4.12 |
| Kemal Naïve Bayes | 43.0/32.6 | 0.57/1.10 | 11.7/35.9 | 4.36/2.61 | 26.0/35.8 | 3.79/2.39 | 24.7/11.2 | 2.24/3.76 |
| Linear SVM | 36.5/32.1 | 1.42/1.58 | 14.6/30.2 | 4.95/2.89 | 15.6/28.3 | 4.67/2.81 | 24.4/16.6 | 2.74/4.80 |
| Fine Gaussian SVM | 64.2/60.5 | 0.24/0.33 | 86.4/91.9 | 0.84/0.39 | 90.7/95.3 | 3.82/1.62 | 84.6/82.2 | 0.67/0.98 |
| Medium Gaussian SVM | 52.0/48.2 | 0.46/0.93 | 32.5/2.12 | 4.05/2.12 | 41.5/61.2 | 3.27/1.37 | 49.6/39.7 | 0.91/3.00 |
| Coarse Gaussian | 39.9/34.9 | 0.76/1.64 | 14.9/32.2 | 5.01/2.89 | 16.7/32.0 | 4.37/2.55 | 25.8/17.8 | 2.57/4.10 |
| Fine KNN | 91.6/90.5 | 0.09/0.18 | 93.8/95.4 | 0.40/0.24 | 97.2/87.8 | 0.11/0.08 | 86.5/85.4 | 0.63/0.83 |
| Medium KNN | 85.3/90.7 | 0.13/0.20 | 79.6/92.8 | 0.65/0.35 | 93.2/94.4 | 0.32/0.22 | 78.4/73.1 | 0.73/0.96 |
| Coarse KNN | 42.0/44.4 | 0.59/0.71 | 14.4/40.0 | 3.78/2.41 | 24.6/40.9 | 3.22/2.08 | 25.9/17.6 | 2.13/2.94 |
| Cosine KNN | 79.2/63.1 | 0.22/0.45 | 59.9/73.8 | 1.91/1.34 | 79.4/81.5 | 1.04/0.72 | 49.5/44.0 | 1.66/2.36 |
| Cubic KNN | 84.9/77.5 | 0.13/0.21 | 78.8/92.3 | 0.68/0.37 | 93.2/94.4 | 0.32/0.22 | 78.0/71.9 | 0.74/1.00 |
| Weighted KNN | 91.5/84.0 | 0.07/0.15 | 90.5/95.9 | 0.29/0.20 | 97.5/98.0 | 0.11/0.07 | 86.5/83.7 | 0.54/0.71 |
| Boosted Trees | 52.2/49.2 | 0.63/1.35 | 17.1/30.6 | 5.61/3.61 | 23.6/36.5 | 4.19/2.80 | 28.6/23.5 | 3.28/5.12 |
| Bagged Trees | 93.8/88.6 | 0.06/0.15 | 93.8/94.5 | 0.35/0.27 | 96.4/96.5 | 0.20/0.13 | 86.5/85.5 | 0.62/0.83 |
| Subspace Discriminant | 18.2/87.7 | 2.48/1.99 | 8.84/21.5 | 7.05/21.5 | 13.6/20.9 | 6.68/3.61 | 15.4/13.4 | 4.17/6.40 |

TABLE 1-continued

Accuracy and misclassification cost of individual color pattern and classification model conditions. The highest accuracy and lowest misclassification cost conditions are highlighted for each pattern.

| | | | | | | | | |
|---|---|---|---|---|---|---|---|---|
| Subspace KNN | 87.7/80.3 | 0.17/0.31 | 76.1/78.6 | 1.67/1.12 | 86.5/88.2 | 0.72/0.55 | 59.1/59.1 | 2.00/2.47 |
| RUSBoosted Trees | 53.7/52.4 | 0.68/1.16 | 20.6/30.7 | 5.08/3.56 | 25.2/34.2 | 3.94/2.32 | 25.7/21.0 | 2.68/4.93 |

| | Pattern 5 | | Pattern 6 | | Pattern 7 | |
|---|---|---|---|---|---|---|
| Model | Accuracy (%, X/Y) | MC (mm, X/Y) | Accuracy (%, X/Y) | MC (mm, X/Y) | Accuracy (%, X/Y) | MC (mm, X/Y) |
| Fine Tree | 41.7/35.5 | 1.42/2.89 | 24.9/40.4 | 3.35/3.04 | 29.4/35.6 | 3.31/2.47 |
| Medium Tree | 23.9/17.2 | 2.00/4.07 | 10.7/23.6 | 4.00/3.69 | 18.0/17.2 | 3.97/3.38 |
| Coarse Tree | 14.7/8.20 | 2.29/4.95 | 7.43/14.1 | 4.24/3.96 | 11.1/8.60 | 4.24/3.90 |
| Linear Discriminant | 16.5/10.7 | 1.97/3.93 | 5.74/15.5 | 4.66/3.76 | 11.3/15.2 | 4.27/3.277 |
| Quadratic Discriminant | 22.1/17.3 | 1.85/3.35 | 6.62/25.0 | 3.94/3.52 | 14.1/24.2 | 4.18/2.89 |
| Gaussian Naïve Bayes | 18.2/12.7 | 1.99/3.90 | 7.72/13.1 | 4.92/4.55 | 11.9/12.0 | 4.49/4.01 |
| Kernal Naïve Bayes | 26.7/18.3 | 1.80/3.83 | 9.30/18.7 | 4.75/4.28 | 16.0/17.6 | 4.41/3.65 |
| Linear SVM | 27.9/16.7 | 2.01/4.68 | 12.1/20.5 | 5.78/4.08 | 13.5/25.2 | 4.98/3.59 |
| Fine Gaussian SVM | 84.3/82.2 | 0.43/1.05 | 59.3/68.2 | 2.19/1.93 | 57.2/63.9 | 2.61/1.95 |
| Medium Gaussian SVM | 46.1/46.7 | 1.57/2.76 | 19.6/31.1 | 4.67/3.86 | 21.5/40.1 | 4.67/3.05 |
| Coarse Gaussian | 28.1/16.6 | 2.01/5.00 | 9.44/16.7 | 5.84/4.63 | 13.0/26.3 | 4.78/3.45 |
| Fine KNN | 87.6/88.1 | 0.36/0.69 | 87.2/89.2 | 0.63/0.66 | 61.8/66.9 | 2.43/1.81 |
| Medium KNN | 77.8/74.0 | 0.44/0.96 | 75.4/86.5 | 0.76/0.83 | 61.0/55.1 | 2.17/1.62 |
| Coarse KNN | 27.2/23.7 | 1.60/2.87 | 12.6/28.4 | 3.64/3.46 | 23.7/19.9 | 3.59/2.88 |
| Cosine KNN | 53.4/48.7 | 1.15/2.08 | 36.3/51.8 | 3.04/2.58 | 33.7/12.2 | 3.55/2.76 |
| Cubic KNN | 77.7/75.0 | 0.45/0.94 | 75.0/86.3 | 0.77/0.85 | 60.9/55.0 | 2.18/1.62 |
| Weighted KNN | 87.5/86.3 | 0.28/0.61 | 85.6/90.3 | 0.53/0.58 | 65.0/64.7 | 2.08/1.52 |
| Boosted Trees | 30.4/23.4 | 2.06/5.42 | 18.6/26.2 | 5.26/4.49 | 19.4/30.5 | 4.81/4.60 |
| Bagged Trees | 87.8/88.8 | 0.35/0.65 | 86.0/87.9 | 0.75/0.72 | 64.5/69.4 | 2.22/1.66 |
| Subspace Discriminant | 19.0/9.70 | 2.56/7.11 | 7.31/16.6 | 8.13/5.05 | 10.5/22.3 | 7.36/4.54 |
| Subspace KNN | 64.2/64.4 | 1.27/2.37 | 68.8/71.4 | 1.81/1.79 | 36.5/42.4 | 3.82/3.16 |
| RUSBoosted Trees | 29.1/19.5 | 2.08/5.12 | 18.6/26.2 | 5.20/4.27 | 20.4/28.4 | 4.75/4.40 |

Five rounds of cross-validation were performed using randomized data partitions. The validation results were averaged across the rounds to give an overall characterization of the model's predictive performance. Pattern performance was characterized using metrics of accuracy, misclassification cost, and training time. Accuracy is calculated as the percentage of data points that were accurately classified. A misclassification cost can be defined (Eq. 1) as the sum average of each data point multiplied by its misclassification penalty (distance from the gold standard). Misclassification cost can be an important characteristic to consider in sensor validation because it is both a function of the Boolean variable accuracy and the magnitude of inaccuracy when a datapoint is misclassified. Prediction speed is the speed of the model to classify data (observations). Data classifications were performed using MATLAB 2021*a* on a 2.5 GHz quad-core processor.

$$\text{Misclassifiaction cost} = \frac{\sum x_i^* p_i}{N} \quad (1)$$

x: number of misclassified data points at coordinate i p: penalty for misclassification at coordinate i N: Total number of data points collected.

From the experiments, accuracy of shear strain sensing was observed to be dependent upon both color pattern and classification algorithm (Table 1). As shown in Table 1 and FIG. 20, on average, KNN classifiers yielded the most accurate strain classification, whereas the pattern 1700C was the most accurate pattern. Predictive speed of the classifiers varied broadly and is summarized in Table 2, with Decision Tree and KNN classifiers having fastest data throughput, and Naïve Bayes and SVM classifiers having the slowest. Thus, reflective pattern and classification algorithm can be selected in relation to each other to improve accuracy of sensor-derived shear strain measurements.

In the experiment, the accuracy of the pixel patterns varied between 65% (pattern 1700G) to 98% (pattern 1700C), as characterized by the most accurate classifier for each pattern. Misclassification cost varied between 0.06 mm (pattern 1700A) and 2.08 mm (pattern 1700G) (Table 1). Overall, color-based patterns outperformed gray scale patterns (92±4.2% vs 78±11% accuracy; 0.30±0.21 mm vs 1.2±0.62 mm misclassification cost), and solid patterns out-performed gradient-based patterns (89±3.8% vs 84±10% accuracy; 0.43±0.22 mm vs 0.78±0.60 mm misclassification cost).

Superior classification outcomes for color-based patterns over gray scale patterns may be due to the broader variety of discrete light wavelengths encompassed in the color pattern, resulting in more distinguishable and unique combinations of RGB light intensities based on shear strain. While color-based patterns encompass approximately the full spectrum of visible light (~400-760 nm), gray scale color patterns may contain less distinguishable combinations of RGB light intensity due to the presence of white (sum of all possible colors), black (absence of color), and gray (approximately equal concentrations of RGB). The addition of color gradients (e.g., patterns 1700B, 1700D, 1700E, 1700G) did not appear to improve accuracy or misclassification costs, nor did the implementation of randomized pixel rotations (patterns 1700B, 1700E, 1700G). However, such pattern design variations may be below a detection capability of the photoresistor or detection system of the sensor. Further, the example patterns with the gradients or rotations also included more white space than the solid patterns, which could impair the ability of the sensor and classification algorithm to determine shear strain based on RGB light intensity.

Figure 20A:
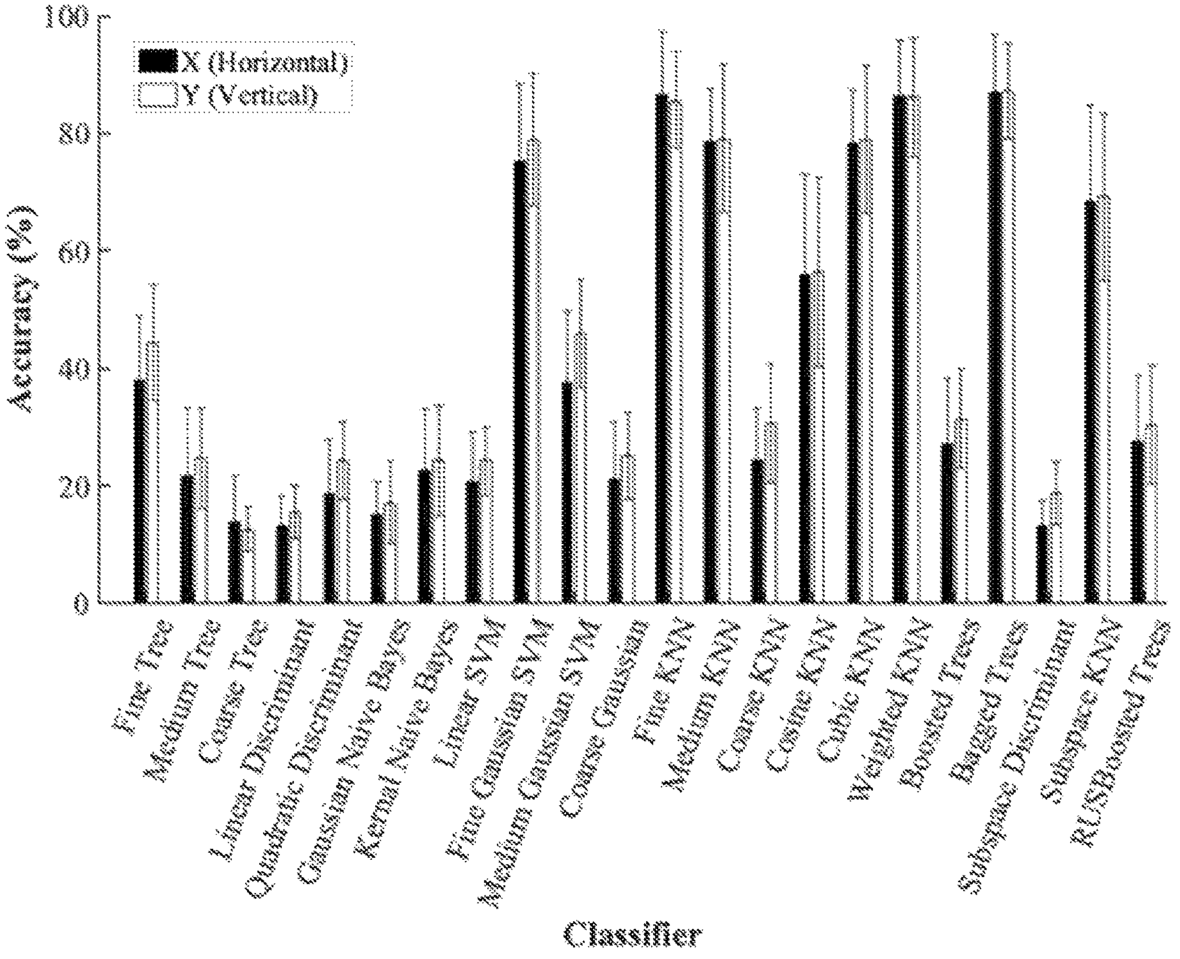
Figure 20B:
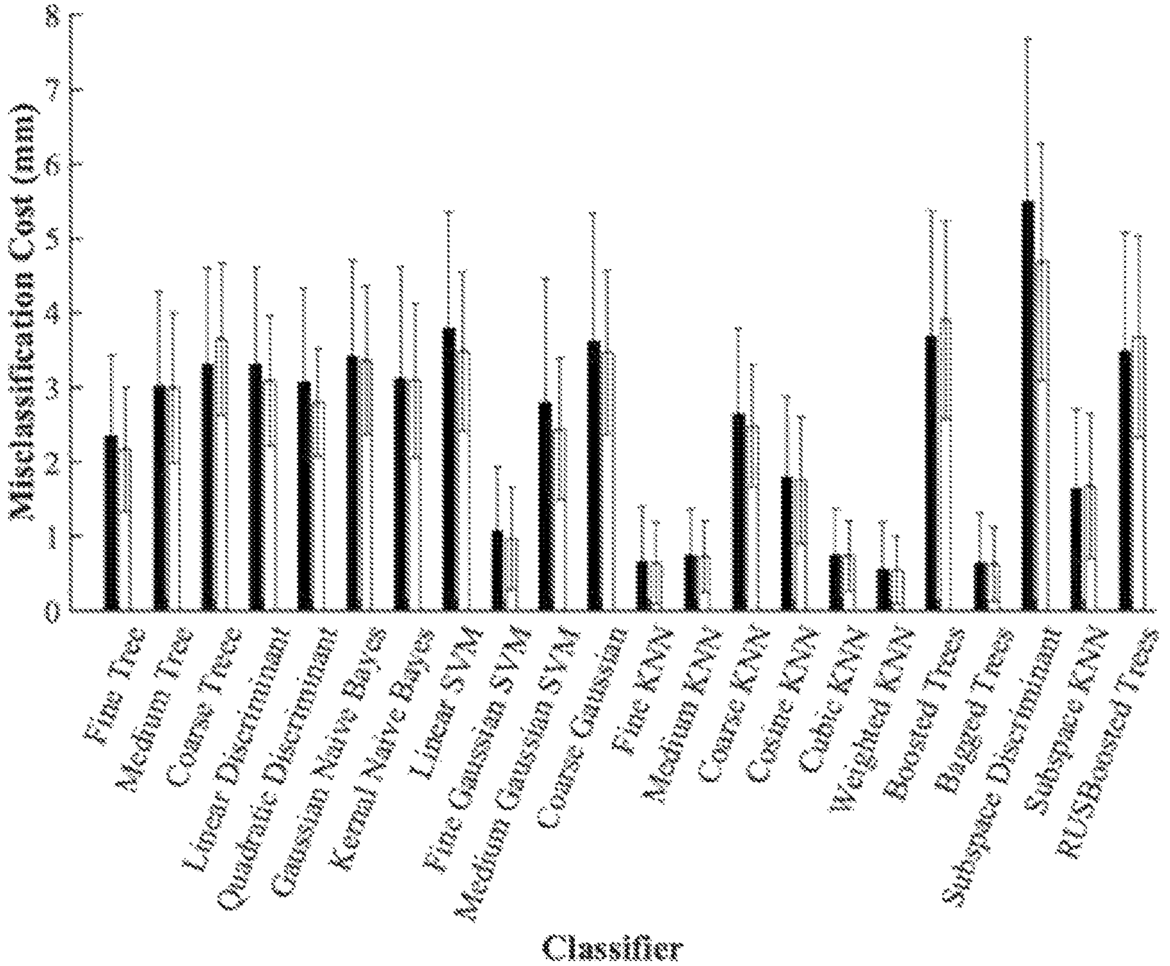

As shown in FIGS. 20A-20B, classifier accuracy and misclassification cost varied broadly as a function of pattern condition. On average, the Weighted KNN and Bagged Trees classifiers yielded the most accurate classifications, whereas Bagged Trees resulted in the lowest misclassification costs. Model fit-based classification algorithms such as discriminant analyses or support vector machines were the poorest performing algorithms for the randomized patterns. This outcome is likely due to the designs of these algorithms, which rely on fitting mathematical functions to the data to stratify and discriminate between outcome classes.

Y: 98.0%) (Tables 1 and 2). Misclassification costs for this configuration were 0.11 and 0.07 mm. Pattern 1700A with the Bagged Trees classifier was less accurate (X: 93.8% and Y: 88.6%), but yielded smaller penalties thus resulting in comparable misclassification costs (X: 0.06 mm and Y: 0.15 mm). The Bagged Trees classifier was also an order of magnitude slower than the Weighted KNN classifier (Table 2), which could make it difficult to deploy on a microcontroller with minimal processing power.

Figure 21A:
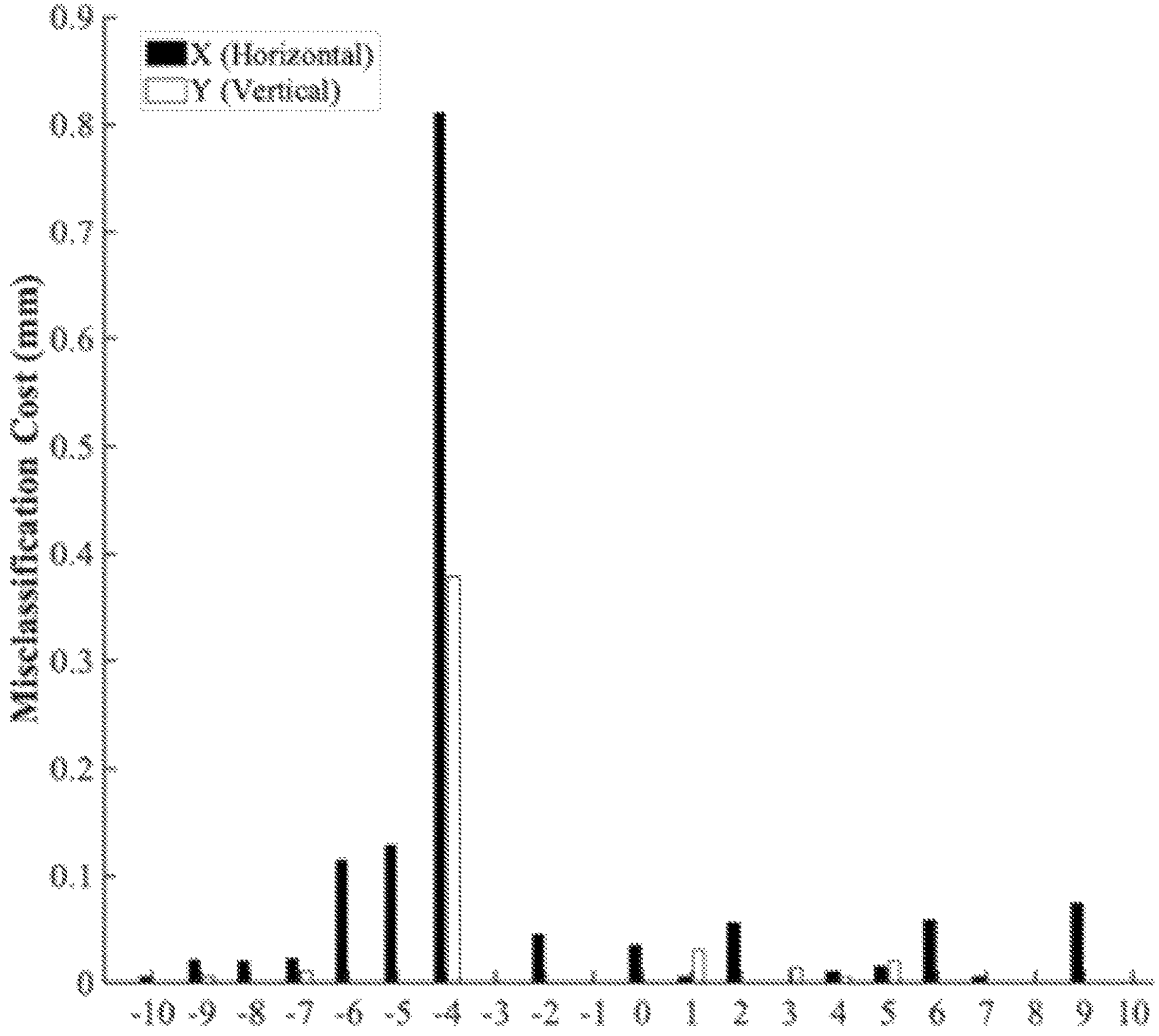
FIGS. 21A-21B are graphs of misclassification cost and accuracy for Pattern 3 data with the Weighted KNN classifier. Missing classification cost bars illustrate an error of zero (100% accuracy).
Figure 21B:
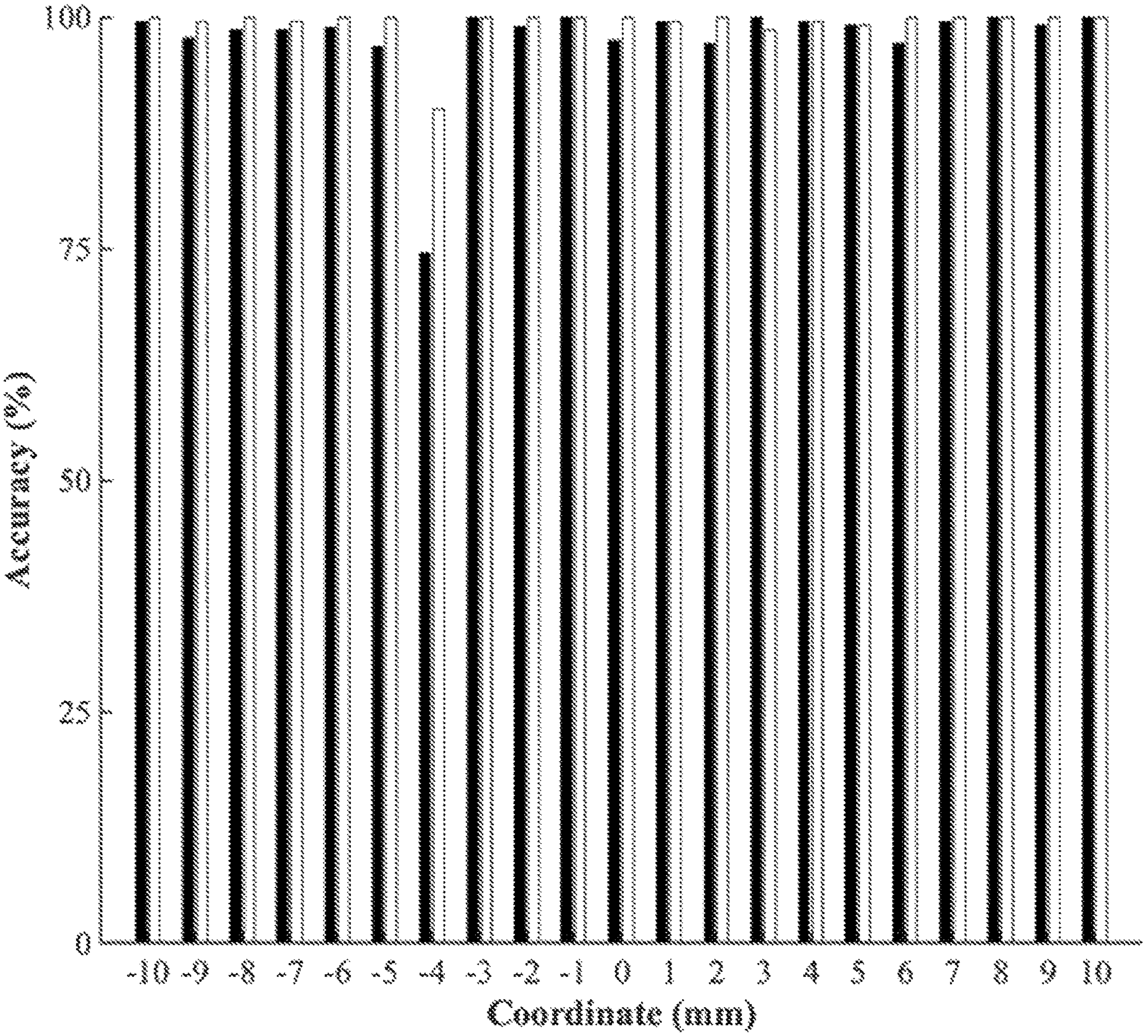

FIGS. 21A-21B depict misclassification and accuracy across each X and Y shear strain data point for an example sensor using the pattern 1700C Weighted KNN condition. For this configuration, sensor accuracy was >97% and misclassification cost was <0.12 mm for all coordinates except −4 mm in the X and Y directions, where error was substantially higher (X: 76% accuracy, 0.81 mm misclassification cost; Y: 90% accuracy, 0.38 mm misclassification cost).

TABLE 2

Predictive speed of classification models. Values are $\times 10^3$. The fastest algorithm is highlighted for each pattern.

| | Predictive speed (observations/s) | | | | | | |
|---|---|---|---|---|---|---|---|
| Model | Pattern 1 | Pattern 2 | Pattern 3 | Pattern 4 | Pattern 5 | Pattern 6 | Pattern 7 |
| Fine Tree | 440 | 390 | 300 | 200 | 100 | 260 | 91.0 |
| Medium Tree | 440 | 320 | 350 | 350 | 360 | 340 | 260 |
| Coarse Tree | 420 | 410 | 350 | 420 | 390 | 320 | 280 |
| Linear Discriminant | 310 | 250 | 240 | 170 | 160 | 230 | 160 |
| Quadratic Discriminant | 160 | 130 | 110 | 130 | 120 | 130 | 100 |
| Gaussian Naïve Bayes | 260 | 180 | 170 | 150 | 140 | 200 | 140 |
| Kernal Naïve Bayes | 2.90 | 1.80 | 1.90 | 2.30 | 2.40 | 2.10 | 1.70 |
| Linear SVM | 31.0 | 8.50 | 8.30 | 7.90 | 7.10 | 7.50 | 7.40 |
| Fine Gaussian SVM | 13.0 | 3.50 | 4.20 | 3.40 | 3.90 | 2.60 | 3.60 |
| Medium Gaussian SVM | 11.0 | 3.10 | 3.90 | 4.00 | 4.20 | 3.10 | 2.80 |
| Coarse Gaussian | 7.50 | 2.50 | 2.80 | 3.40 | 3.90 | 2.60 | 2.80 |
| Fine KNN | 220 | 240 | 250 | 250 | 160 | 240 | 150 |
| Medium KNN | 160 | 160 | 150 | 160 | 150 | 180 | 120 |
| Coarse KNN | 53.0 | 78.0 | 63.0 | 79.0 | 72.0 | 79.0 | 71.0 |
| Cosine KNN | 42.0 | 66.0 | 68.0 | 61.0 | 53.0 | 80.0 | 57.0 |
| Cubic KNN | 120 | 120 | 110 | 92.0 | 88.0 | 110 | 91.0 |
| Weighted KNN | 180 | 170 | 180 | 150 | 150 | 150 | 130 |
| Boosted Trees | 29.0 | 30.0 | 26.0 | 22.0 | 26.0 | 29.0 | 23.0 |
| Bagged Trees | 20.0 | 17.0 | 17.0 | 16.0 | 18.0 | 16.0 | 15.0 |
| Subspace Discriminant | 17.0 | 13.0 | 13.0 | 11.0 | 14.0 | 11.0 | 12.0 |
| Subspace KNN | 14.0 | 13.0 | 14.0 | 11.0 | 14.0 | 12.0 | 12.0 |
| RUSBoosted Trees | 28.0 | 24.0 | 28.0 | 26.0 | 28.0 | 21.0 | 26.0 |

The pixel arrangements in patterns 1700B-1700G are randomized and are therefore arduous or impossible to represent through data fitting. In contrast, decision-based algorithms, such as Nearest Neighbor algorithms tended to provide more accurate shear strain classification, possibly due to independence from data fitting.

The various classifiers also exhibited a broad range of classification speeds (Table 2). Decision Tree models were the fastest with speeds ranging 240,000-400,000 observations/s, whereas Naïve Bayes and Support Vector Machine models were the slowest with speeds<10,000 observations/s. There was a tradeoff between speed and accuracy, whereby Decision Tree models were the fastest but not the most accurate (Tables 1 and 2). However, this tradeoff was inconsistent, as some of the slowest models, Naïve Bayes models for example, were also some of the least accurate. Tested classifications were derived through offline processing on a computer with a quad-core 2.5 GHz processor.

Pattern 1700C paired with the Weighted KNN classifier was found to be the most accurate configuration (X: 97.5%, There were 50 misclassified datapoints (24% error) at −4 mm of shear strain in the X direction. Of these misclassifications, 63% were incorrectly classified as −4 mm when true strain was −6 mm and 35% were incorrectly classified as −4 mm when true strain was −9 mm. In the Y direction, there were 20 misclassified datapoints (9.5% error) at −4 mm shear strain. Of these misclassifications, 45% were incorrectly classified as −4 mm when true strain was −6 mm and 55% were incorrectly classified as −4 mm when true strain was −9 mm. These data indicate that there may be commonalities in the RGB intensities among the pixels in the window on Surface A at −4 mm, −6 mm, and −9 mm of X shear strain and −4, −6, and −9 mm of Y shear strain. This may be due to inadequate randomization of color pixel location. Alternatively, randomization may have been adequate, but different combinations of color pixels could result in similar RGB intensities. In further examples, other varieties of colors could be incorporated into randomization characteristics of pixel patterns to reduce the likelihood of common RGB intensities. Pixel distributions could also be mathematically optimized and pseudo-randomized such that clusters of pixels with similar color distributions are subjected to repeated randomization. For example, applying such strategies could achieve sensor performance similar to the mean accuracy and misclassification costs of the remaining datapoints, resulting in an overall sensor accuracy of 98.9% and 99.7% in the X and Y directions. Misclassification costs would be 0.03 mm and 0.02 mm in the X and Y directions.

Sensors can be susceptible to noise induced by ambient light. Such noise can be addressed in various ways, such as a more thorough blocking or sealing of the photoresistor from ambient light. Alternatively, the LED and photoresistor could be paired by wavelength such that the photoresistor is only sensitive to the specific wavelength produced by the LED. Additional examples are discussed further hereinbelow.

As with examples described herein, sensors can be configured to communicate wirelessly, e.g., through Bluetooth (e.g., Bluegiga BLE113) or another wireless protocol, so that data and shear sensing can occur in real-time, including application of Weighted KNN classifier or other classifiers deployed on a microprocessor. It will be appreciated that randomized patterns and classification based approaches can be applicable to any of the disclosed examples described herein, including those in which an elastomer layer is arranged between Surfaces A and B (e.g., in a continuous layer or a layer of elastomer portions spaced apart from each other). In some examples, flexible PCBs may be used for sensor components. Currently, the use of rapid fabrication techniques (e.g., 3D printing and use of PCBs) in the construction of this sensor can be advantageous for quickly designing, implementing, and testing modifications. However, other manufacturing processes can be used including those that rely on traditional mass fabrication methods such as injection molding and automated circuit population to improve sensor-to-sensor repeatability and manufacturing speed.

Disclosed examples using data classification techniques can allow determination of directionality of shear measurements. Example sensors have demonstrated robust and accurate measurements of multi-axial shear strains. These properties, along with its small, low-cost, and scalable design support the use of this sensor and sensing paradigm for a variety of applications in robotics and orthopedics.

Additional Examples Using Broadband Sources and/or Filters

FIG. 22 is another example of a sensor 2200 that can measure multi-axial shear force and displacement based on optical coupling between opposing surfaces. In the sensor 2200, white light 2201 from an LED 2202 is reflected off a color pattern 2204 and a four-channel photodiode 2206 with red, green, blue, and white (full visible spectrum) sensing elements is arranged to detect the reflected light 2203. The sensor 2200 can be similar in some ways to the sensor 400. The color pattern 2204 is arranged on a Surface A and the light is emitted towards the Surface A from a viewing window 2208 defining a Surface B. Example patterns for Surface A and Surface B are depicted in FIGS. 23A-23B and windowed transmission for different shear displacements is shown 23C-23F. The viewing window 2208 can be situated on an instrumented side of the sensor 2200, e.g., as an aperture in a sensor housing 2210. The photodiode 2206 and LED 2202 can be situated at or close to the plane of the viewing window 2208. The color pattern 2204 on an opposing side of the sensor 2200 (FIGS. 22 and 23B, Surface B) can be a colored grid consisting of green, red, blue, and magenta (red+blue) panels. In various examples, any of the other disclosed patterns and pattern variations may also be used as described herein.

The sensor 2200 can include an intermediate layer 2212 of polyurethane elastomer (PUE) blocks separating Surfaces A and B (FIG. 22). The thickness of the sensor 2200 can be largely dependent upon the thickness of the elastomer layer 2212. The blocks can be non-transparent. The maximum range and sensitivity towards shear stress can be tuned by changing the elastomer material and thickness, which affects the stress-strain properties of the material. For example, the PUE used in this example sensor configuration has an elastic modulus of 4.0 MPa. In further examples, a polydimethylsiloxane (PDMS) elastomer with a lower elastic modulus (250-450 kPa) could be used for higher resolution, lower range sensor configuration.

In a selected example, the LED 2202 (e.g., Everlight Electronics, 45-21/LK2C-B38452C4CB2/2T) is 3.0×2.0×1.4 mm (thickness) and emits light in a 400-800 nm spectrum. At 20 mA, the LED 2202 has a brightness of ~2,000 milicandella (mcd). The photodiode 2206 (e.g., Texas Advanced Optoelectronic Solutions, TCS34725) is 2.0×2.4×1.6 mm. The photodiode 2206 can have individual red, green, blue, and clear light sensing elements with an infrared blocking filter. For example, the individual light sensing elements can include respective bandpass filters to attenuate wavelengths away from the sensing wavelength or wavelength range. Four integrated analog-to-digital converters (ADCs) convert photodiode currents to 16-bit digital values. Peak responsivity of the sensing elements occurs at 620 nm (red), 550 nm (green), and 475 nm (blue). The device utilizes an I2C fast communication protocol for data rates of up to 400 kbit/s. It consumes 2.5 μA in standby mode and 65 μA when operating.

The LED 2202 and photodiode 2206 are soldered to a printed circuit board 2214 (e.g., OshPark Inc., 2 oz Copper, 0.8 mm thickness) housed in the housing 2210, which can be a 3D printed methylacrylate photopolymer resin (e.g., FormLabs Inc., Rigid 10k). This resin has a tensile modulus of 10 GPa and a flexural modulus of 9 GPa. By employing rapid prototyping technology in the fabrication process, the sensor's cost-efficiency and versatility can be improved. The color pattern 2204 was printed on an adhesive-backed vinyl with matte finish (e.g., Strathmore Inc., 59-635).

The flexible PUE layer 2212 incorporated between Surfaces A and B can provide mechanical elasticity to the sensor 2200. The PUE layer 2212 (e.g., durometer: 80a, thickness: 3.5 mm) was laser cut into 4 cuboids (e.g., 8.0×8.0×3.5 (thickness) mm) adhered between the surfaces at each corner of the surface interface (e.g., Loctite 401, Düsseldorf, Germany) (FIG. 22). The glue was allowed to cure for 24 h at room temperature. The PUE has a reported elastic modulus ranging 4.7-7.4 MPa.

FIGS. 24A-24D is a prototype sensor 2400 similar to the sensor 2200 and that was integrated into footwear for human gait monitoring. The sensor 2400 includes a wireless communication module 2402, such as a Bluetooth Low-Energy (BLE) transceiver (Silicon Labs Inc., BLE113) with an integrated microcontroller unit (MCU). The transceiver with MCU was incorporated to control the electronics and wirelessly stream data to a computer or smartphone. A CR2016 lithium manganese dioxide coin cell battery (3V, 90 mAh) was also included in a slot 2404 to provide wireless power to the sensor 2400. A battery of this capacity can power the sensor 2400 during active data collection for an estimated 3 h. A higher capacity battery could be incorporated to lengthen collection time. In this prototype configuration, the sensor packaging is 34×27×9 mm (thickness) and weighs 1.16 g including the battery.

As stated above, the BLE113 module 2402 contains an MCU for controlling the sensor 2400. The module 2402 further includes local memory for hosting data and end user applications and a BLE radio for bi-directional communication with a computer or smartphone. The MCU can set the sensor 2400 in two operation modes: standby/sleep mode and active sensing mode. In standby mode, the sensor 2400 receives no power and the BLE113 consumes only 0.4 µA. In active sensing mode where an LED and photodiode are active and data are being streamed to an external Bluetooth-enabled device, the BLE113 consumes 18 mA.

Figure 25:
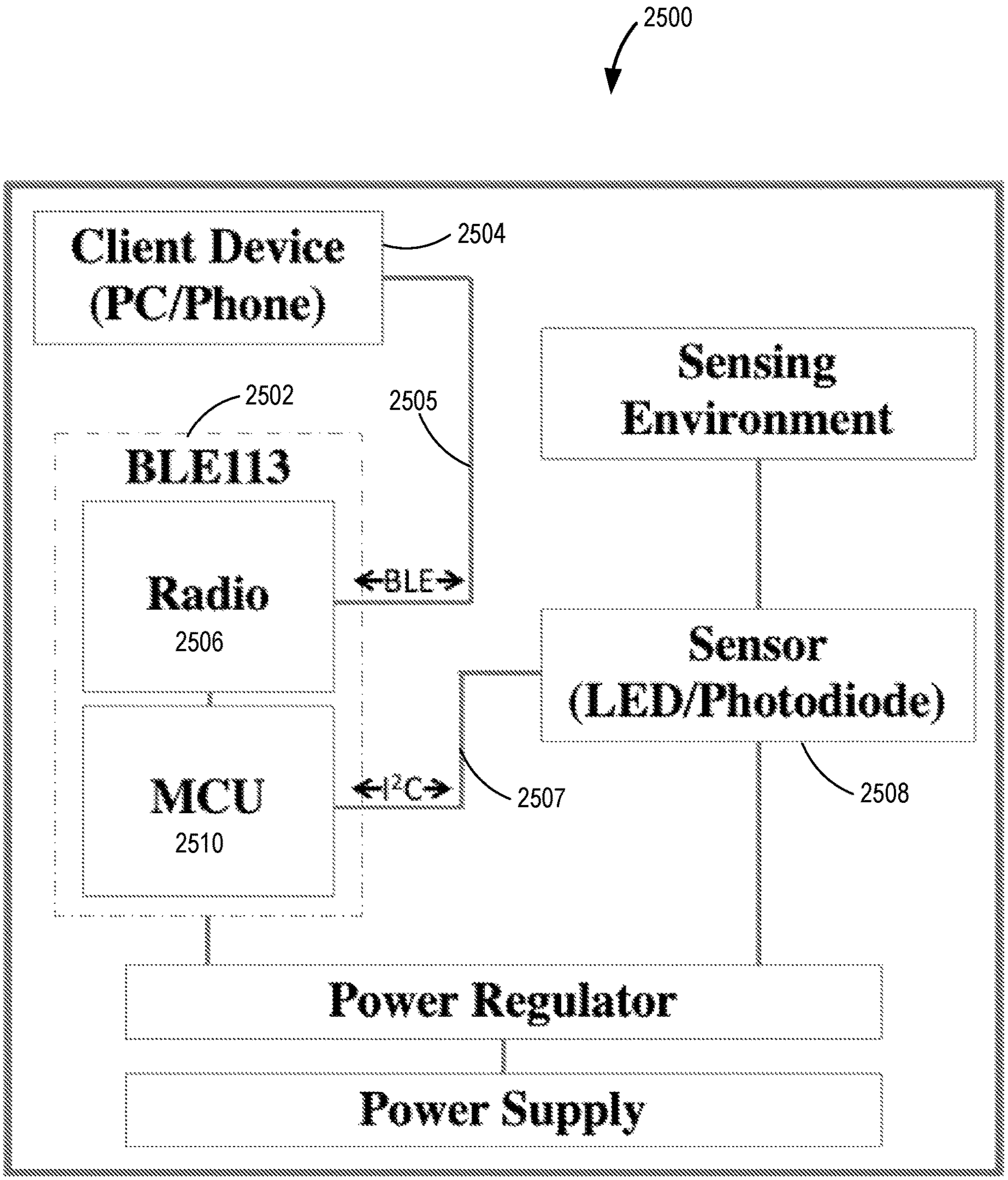
FIG. 25 is a block diagram of the telemetry platform.

A block diagram of a telemetry platform 2500 that can be used for the sensor 2400 as well as other sensors described herein is depicted in FIG. 25. A BLE113 module 2502 acts as the host device and sets the sensing mode based on client inputs from a client device 2504 in wireless communication 2505 with a radio transceiver portion 2506 the module 2502. In active mode, an LED of the optical sensing components 2508 is turned on and a photodiode sampling from a photodiode of the optical sensing components 2508 is prompted via an $I^2C$-fast communication protocol 2507. A program onboard an MCU 2510 stores photodiode measurements and creates a 20-byte data packet. These packets can be transmitted to the client device 2504 (e.g., a computer) at a rate of 30 Hz, giving the sensor an effective sampling rate of 180 Hz and providing near real-time data streaming to the end user.

Figure 24A:
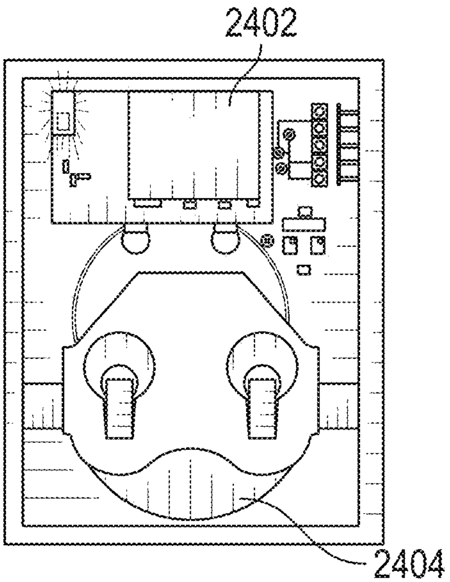
FIGS. 24A-24D are photos of wireless sensor implementation.
Figure 24B:
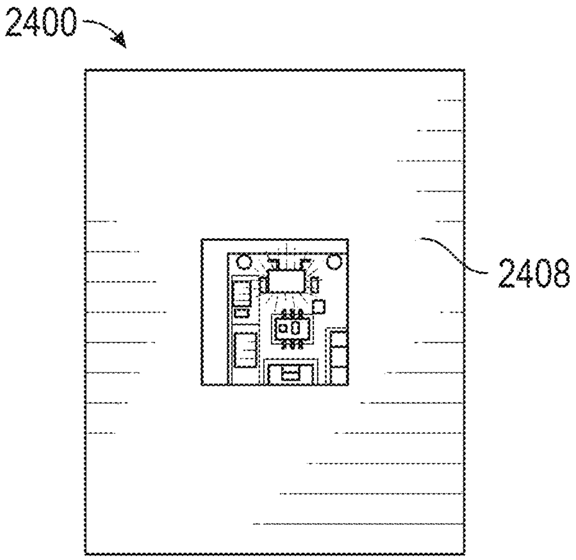
Figure 24C:
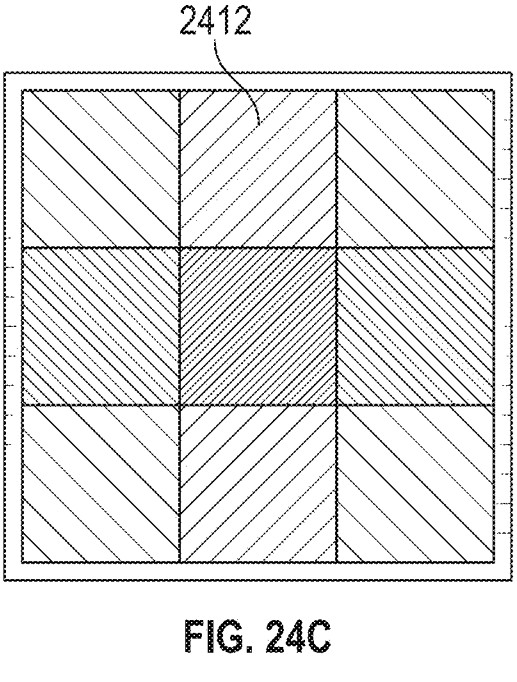
Figure 24D:
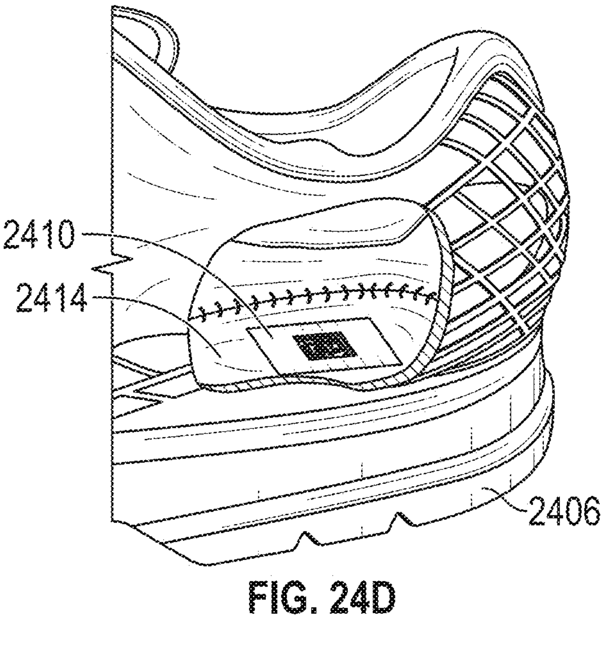

As shown in FIG. 24D, the sensor 2400 was embedded in a shoe 2406. A Surface A 2408 of the sensor 2400 was embedded into a midsole 2410 of the shoe 2406. A Surface B 2412 having a color pattern was adhered to the underside of an insole 2414 of the shoe 2406. To integrate the sensor 2400 into the shoe 2406, a rectangular hole (L×W×H) matching the dimensions of Surface A 2408 was excised from the midsole. The instrumented side of the sensor 2400 was then secured in the midsole 2410 (e.g., Loctite 401, Düsseldorf, Germany). The color pattern (Surface B 2412) was adhered to the corresponding location on the underside of the shoe's insole 2414. A PUE elastomer layer was then adhered between the two Surfaces A and B using methods described above. Other configurations are possible, including flipping the arrangement of the Surfaces A and B, separating the Surfaces A and B such that they are facially coupled but not adhered to each other, positioning the sensor in other locations of the shoe including farther up the sole towards the toes, along a heel or tongue, contacting the ground, etc.

Figure 26B:
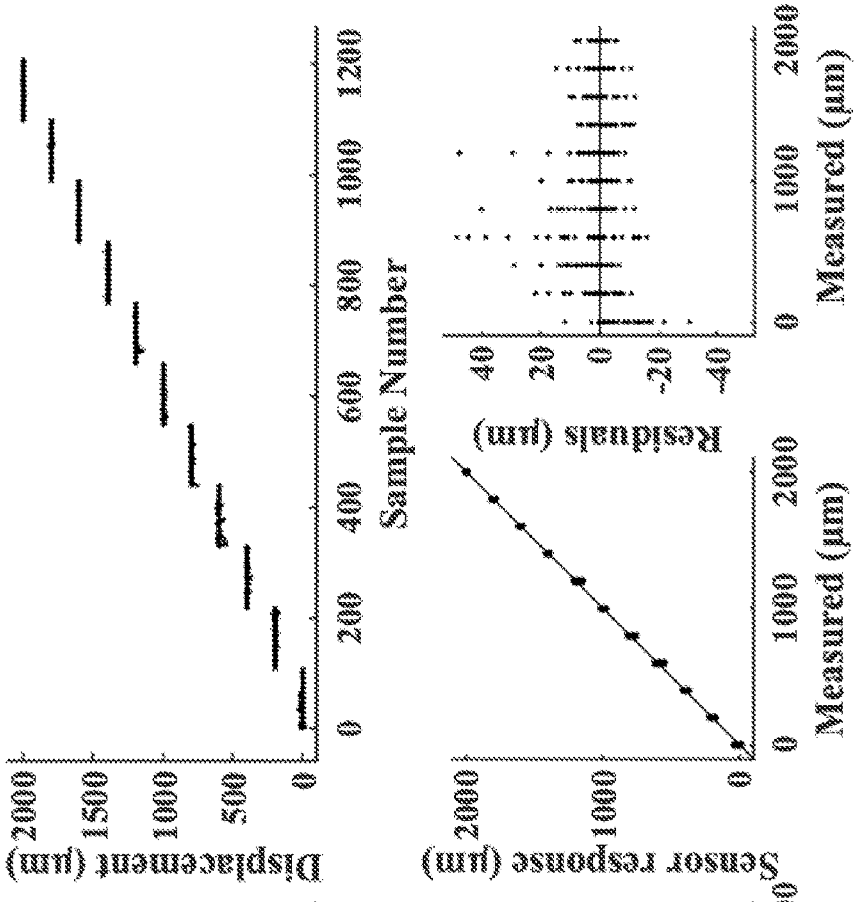
FIG. 26A-26B are graphs of sensor performance compared to gold standard displacement measurements in vertical (FIG. 26A) and horizontal (FIG. 26B) directions. The number of samples was n=1201.
Figure 26A:
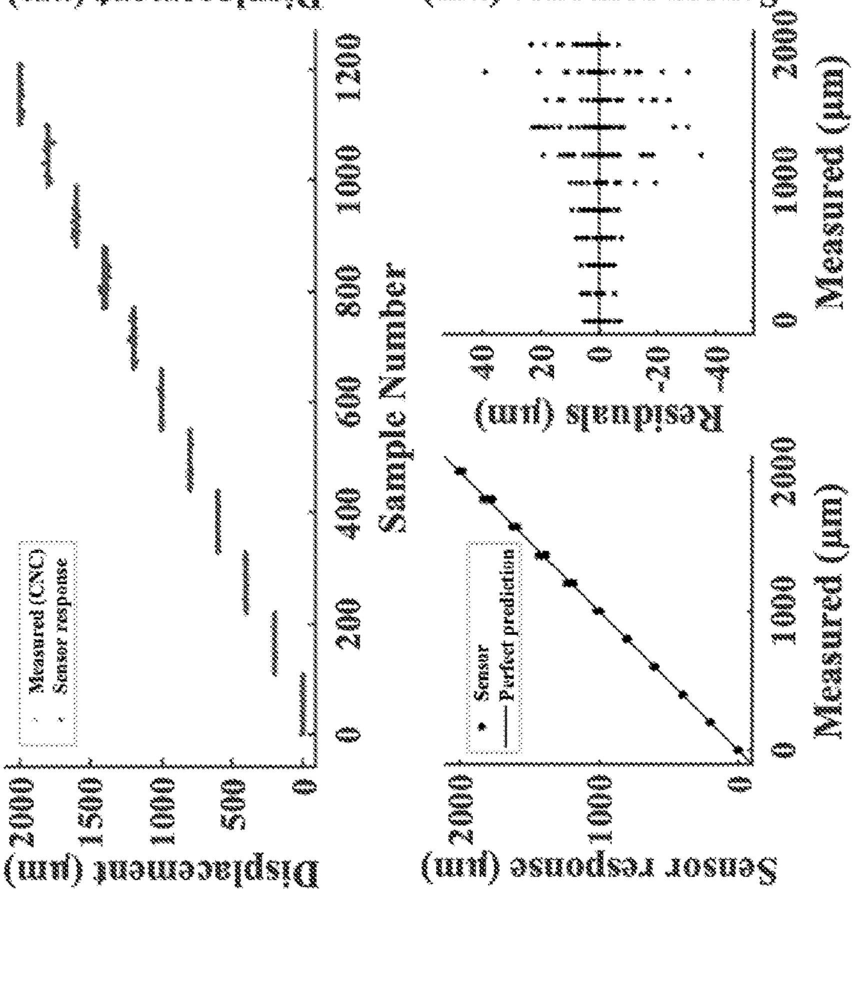

Sensor-derived measurements of displacement for the sensor 2400 using a test apparatus demonstrated a high level of agreement with gold standard data. As shown in Table 3 and FIG. 26A, in the vertical direction, the modeled sensor data exhibited an $R^2>0.99$ with an RMSE of 4.5 µm. The largest residuals occurred for displacements greater than 1 mm, with the highest error value (40 µm) occurring at 1.8 mm displacement. Similar performance was observed in the horizontal direction ($R^2>0.99$, RMSE: 5.0 µm) as shown in FIG. 26B. In this direction, the residuals were relatively consistent across the full range of tested displacements, with the highest residual (50 µm) occurring at 0.6 mm displacement.

TABLE 3

Summary of sensor performance.

| | Displacement (µm) | | Force (N) | |
|---|---|---|---|---|
| | Vertical | Horizontal | Vertical | Horizontal |
| $R^2$ | >0.99 | >0.99 | >0.99 | >0.99 |
| RMSE | 4.5 | 5.0 | 0.94 | 0.84 |
| MAE | 1.7 | 1.8 | 0.31 | 0.54 |

Figure 27B:
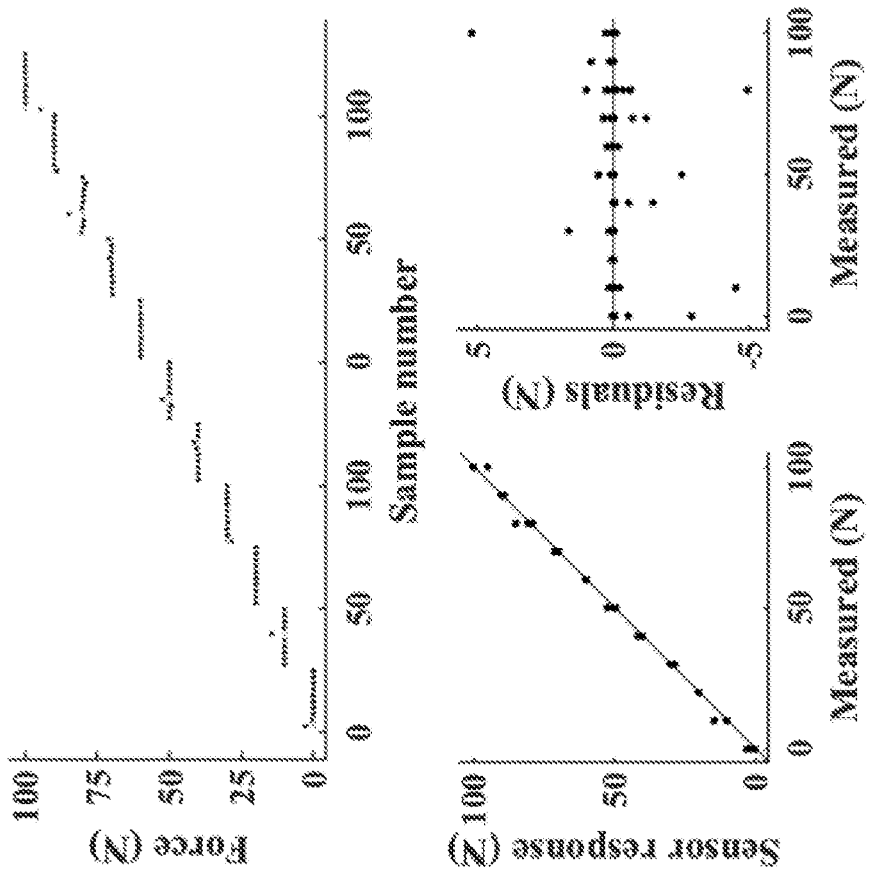
FIG. 27A-27B are graphs of sensor performance compared to gold standard displacement measurements in vertical (FIG. 27A) and horizontal (FIG. 27B) directions. The number of samples was n=121.
Figure 27A:
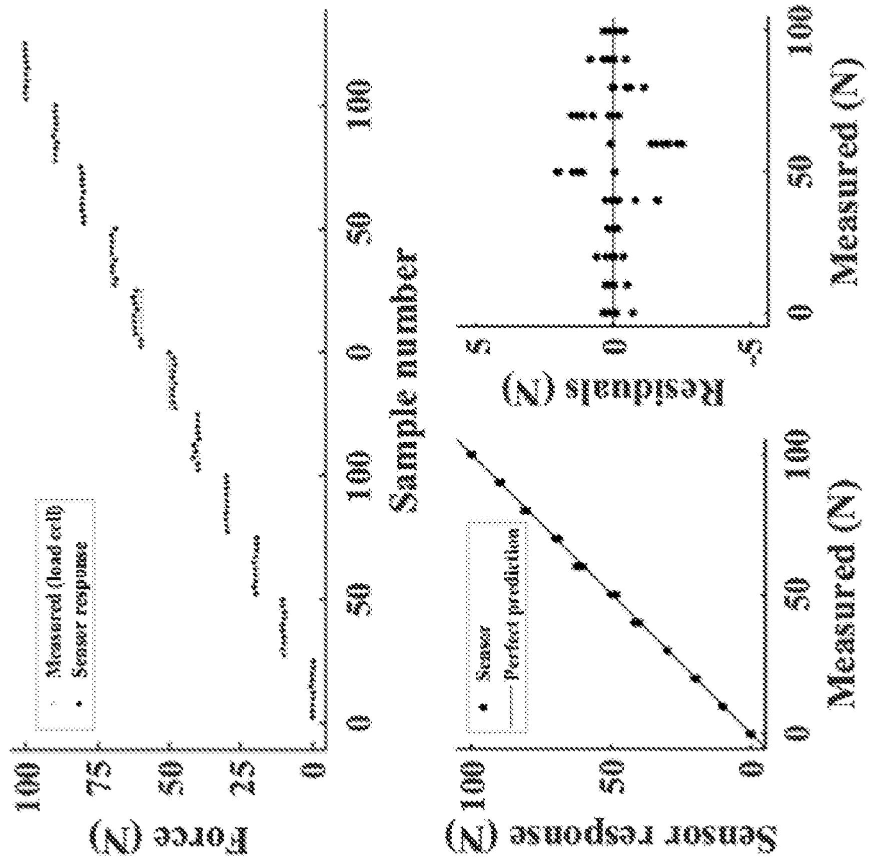
Figure 28:
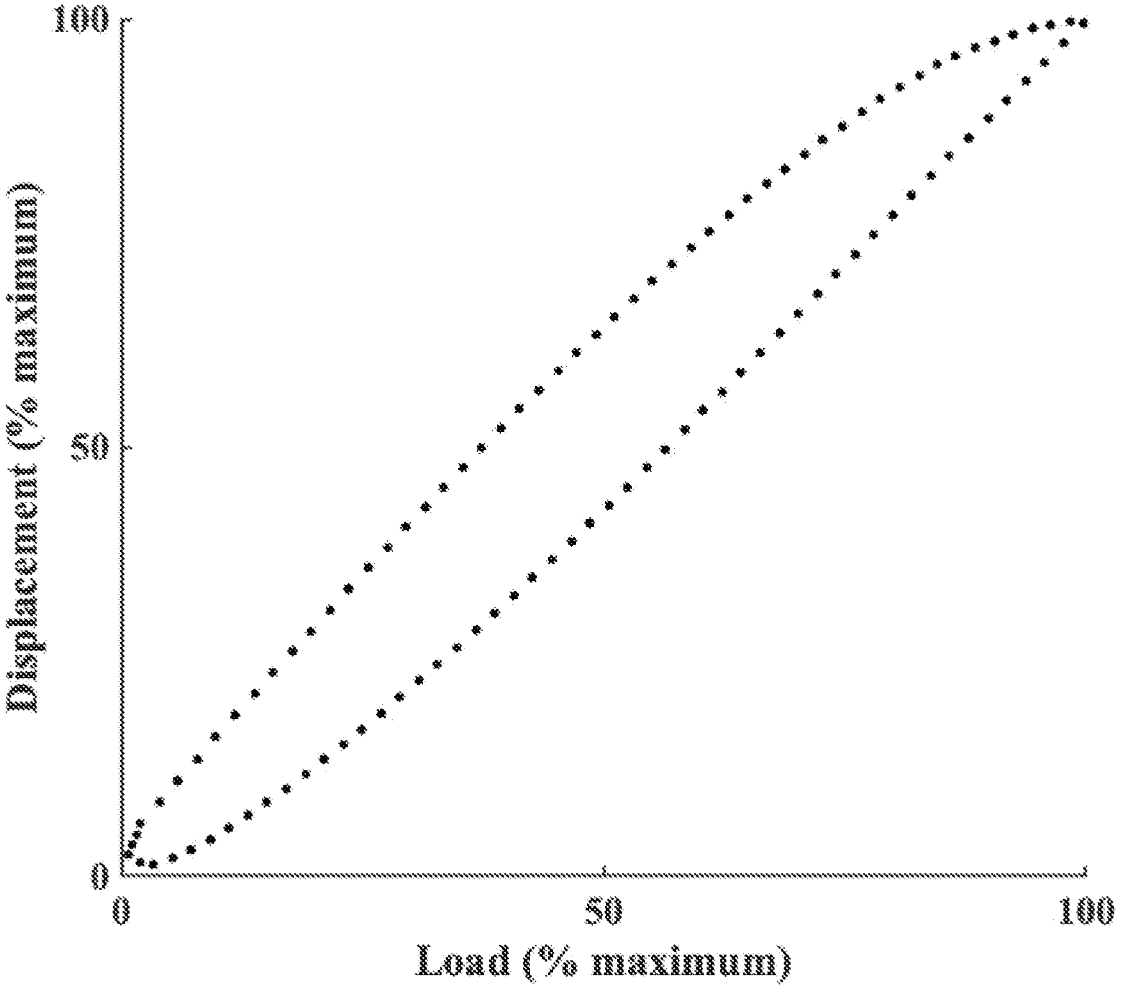
FIG. 28 is a graph of hysteresis response for a sensor measured via MTS and load cell.

Sensor-derived measurements of shear force also exhibited good agreement with gold standard load cell data (Table 3, FIGS. 27A-27B). In the vertical direction, the modeled sensor data were strongly correlated with the load cell ($R^2>0.99$, RMSE: 0.94 N, MAE: 0.31 N) across the 0-100 N loading range. Similar performance was evident in the horizonal direction ($R^2>0.99$, RMSE: 0.84 N, MAE: 0.54 N). The highest residuals (i.e., error) occurred in the 40-70 N loading range for vertical forces and were relatively evenly distributed across the full loading range of horizonal forces.

Figure 29:
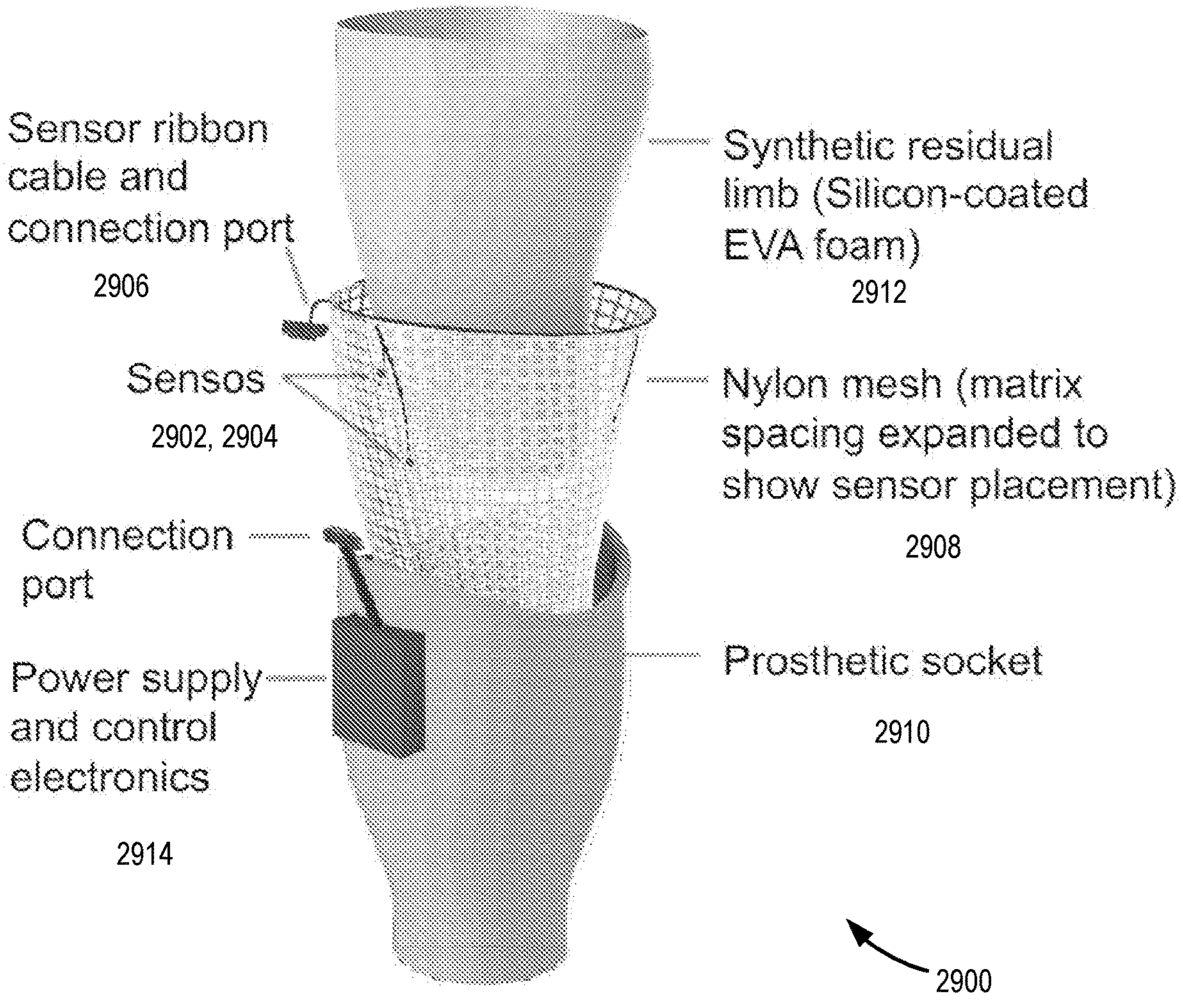
FIG. 29 is a perspective view of a sensor and an instrumented prosthetic socket liner.

To investigate the elastic behavior of the physical sensor package of the sensor 2400 (e.g., PUE, assuming the resin housing is rigid) the stiffness and hysteresis of the packaged sensor were evaluated. The sensor 2400 exhibited a linear relationship between load and displacement ($R^2>0.98$) as measured via the test apparatus comprising a load cell and MTS displacement sensor. Average hysteresis was 7.8 N across the full range of loads and displacements (FIG. 29). The relationship between force (F) and displacement (x) was 101.0 N/mm. Assuming rigidity of the sensor housing, the shear modulus of the PUE with surface area "A" was calculated to be 3.95 MPa (eq. 1).

As shown above, the prototype sensor 2400 detected two-axis applied shear displacement with a high degree of accuracy using a color sensing approach based on optical coupling between a white light LED and an RGB photodiode and force. The sensor 2400 demonstrated a robust ability to detect shear displacement within a 2 mm dynamic range and applied shear force within a 100 N dynamic range. The performance of the sensor 2400, combined with its small form and scalable design support its use for a variety of biomedical and sport applications, including in one example being wirelessly integrated into the sole of a shoe. In selected applications, the sensor embedded in a shoe can be used to monitor human gait biomechanics.

The sensor 2400 demonstrated a high level of accuracy and resolution for measuring two-axis shear displacement and applied forces under benchtop testing conditions. Average inter-measurement variability was <0.1% for all conditions, indicating that the sensor is repeatably accurate. The sensor exhibited linearity of >0.99 for displacement and >0.98 for forces, as calculated by the slope of the relationship between the sensor output and gold standard values. High linearity is beneficial for wearable wireless sensors, because it potentially allows for simplified signal conditioning and data processing, thereby reducing the computational requirements for an MCU.

The highest displacement error was 50 µm (2.5%), whereas the highest error for applied force was 5.2 N (5.2%). The relatively higher error for force sensing may be attributed to minor imperfections in the sensor fabrication process. For example, the PUE layers and their interfaces with Surfaces A and B may not have been completely homogenous, resulting in small inconsistencies in stiffness across the loading range. Similarly, error could occur due to slippage of the glue adhering the PUE between Surfaces A and B. Future designs could improve the adhesion process or utilize techniques such as injection molding to directly incorporate the PUE layer into the sensor structure.

The sensor exhibited an average stiffness of 101 N/mm and hysteresis of 7.8 N across a 0-100 N loading range. The sensor stiffness derived from mechanical testing was slightly lower than previously reported material properties for PUE. This discrepancy may indicate that the sensor housing is not completely rigid under the testing loads or that small amounts of slippage of the glue occurred during testing. The hysteresis could be a limitation for sensing shear forces in biomechanical applications such as human gait, where loading and unloading characteristics are both important considerations. Sensor hysteresis could be improved by incorporating other elastomers such as PDMS, which was previously shown to have less hysteresis in similarly configured sensors. Other elastic structures such as coil and/or leaf springs could also be used.

Anterior-posterior and medial-lateral shear forces occurring during level ground human gait range 0-1.5 N/kg of body weight. For a 70 kg individual, this equates to 0-105 N, indicating that the example sensor 2400 is well-suited for monitoring shear forces under these conditions. In some selected application, the prototype in-shoe sensor 2400 can be used to measure foot-shoe interface dynamics during walking. Excessive shear forces are a leading factor in tissue damage on the plantar surface of the foot. Such example sensors could serve as a monitoring system for tissue health and lead to improved prevention and healthcare strategies for plantar tissue ulcers. Shear forces may increase as high as 4 N/kg in other walking conditions (e.g., stair ascent/descent and ramp ascent/descent) and higher in athletics scenarios, and disclosed examples can be extended to measure forces in this range. Further examples can include sensors scaled for use in different sensing applications with different range and accuracy requirements. Additional examples can use different elastomers with different elastic moduli to custom tune the sensor for specific applications. For example, a PDMS elastomer layer with a lower elastic modulus (250-450 kPa) could be used for a higher resolution, lower range sensor configuration.

The data demonstrate good differentiation between horizontal and vertical shearing and indicate that the sensor performs equally well in both directions (Table 3, FIGS. 26A-27B). Historically, the ability to measure multi-axial shear displacement and force has been primarily limited to use of strain gauges. Compared to this sensor, other wearable force sensors have been heavier (e.g., 375 g or more), require more power (e.g., ~700 mA), and/or need wired power sources. The prototype sensor 2400 has a current draw of ~21 mA without the BLE module and ~30 mA with the BLE module, allowing wireless operation and minimal battery requirements.

Additional Sensor Applications

In some examples, disclosed sensors can be implemented in robotics applications. For example, sensors can situated to provide feedback for a grasping robot to handle a fragile object by providing the necessary grip force to manipulate the object without breaking it. In clinical circumstances, pressures of <8 kPa can cause tissue ischemia, which necessitate high resolution for sensors tasked with preventing ischemia and skin breakdown. Shear stress has been shown to be at least equivalent to pressure as an external factor leading to tissue breakdown. Although some of the disclosed sensor examples were configured to sense shearing of up to 20 N, examples can be scaled to match a variety of sensing ranges and resolutions. For applications with different shear forces, the sensor can be reconfigured with elastomers of different properties to customize sensing capacity.

Another potential future use case for disclosed sensor examples is integration within a prosthetic socket to provide precise measurements of shear stress. Such measurements can provide shear information that can be used to reduce or prevent residual limb tissue breakdown. FIG. 29 shows an example implementation in a prosthesis 2900. One or more shear sensors 2902, 2904 arranged along a sensor ribbon cable 2906. The sensor ribbon 2906 is integrated within a nylon mesh prosthetic socket liner 2908 at six anatomical locations known to be at risk of elevated localized shear stresses. The nylon mesh liner 2908 that can be disposed between a prosthetic socket 2910 and a synthetic residual limb 2912. The sensors 2902, 2904 are ported via the ribbon cable 2906 to a power source and control box 2914 worn outside the socket 2910.

Figure 32:
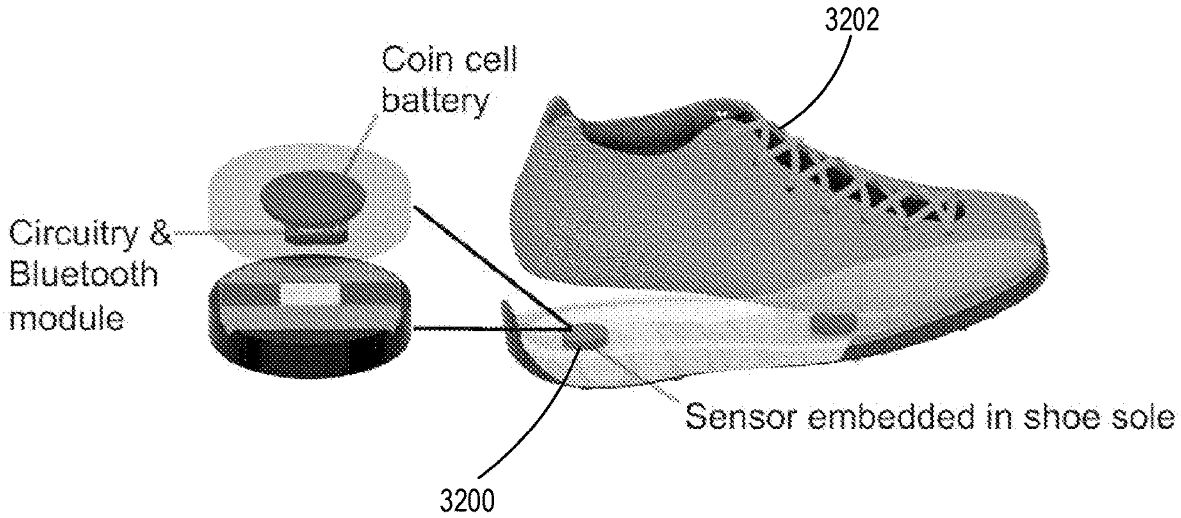
FIG. 32 is a perspective view of an instrumented shoe insole.

A further implementation is shown in FIG. 32 which shows another example of a wireless sensor 3200 with an integrated Bluetooth module for sensor control and data streaming. The sensor 3200 is well-suited to be integrated within the insole of a shoe 3202 for measuring shearing between the foot and shoe in athletics settings or for patients with diabetic peripheral neuropathy.

Additional implementations can include integration of various disclosed sensor and sensor elements into existing systems. For example, the light source and detector could be embedded into a particular part of an existing robot or wearable device and the pattern could be adhered to another shearing body of interest such as another robotic member or an opposing surface of a wearable device (such as the skin or clothing).

Sensors With Mechanical Attenuators

Figure 30A:
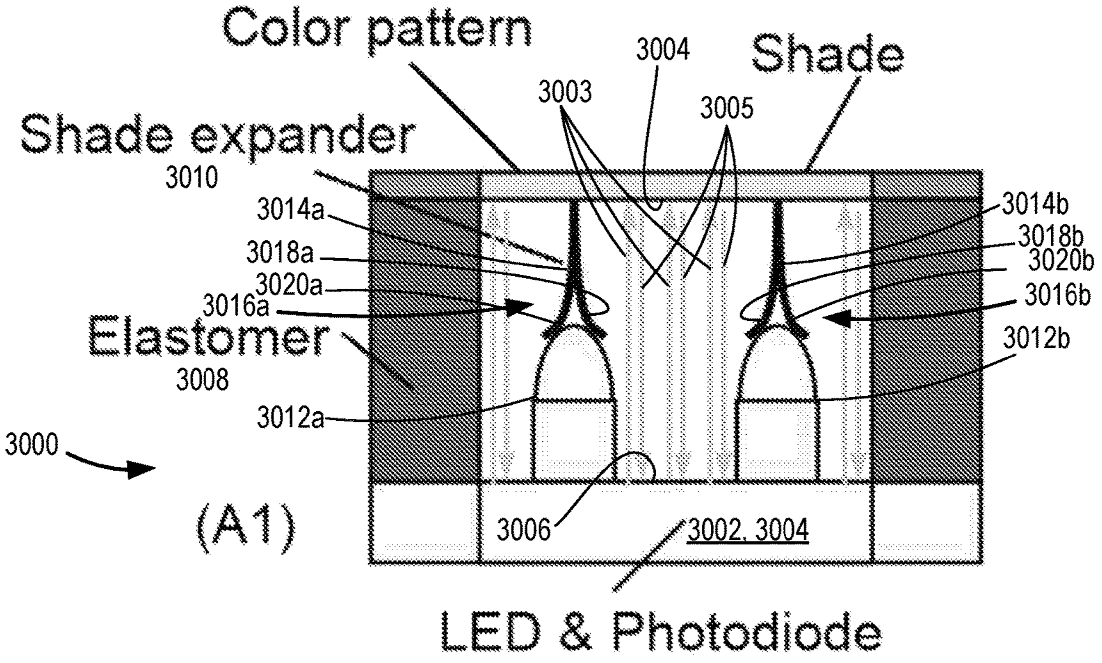
FIG. 30A is a side view schematic of an example sensor that includes a shade expanded for measuring or calibrating out compression displacement or force.
Figure 30B:
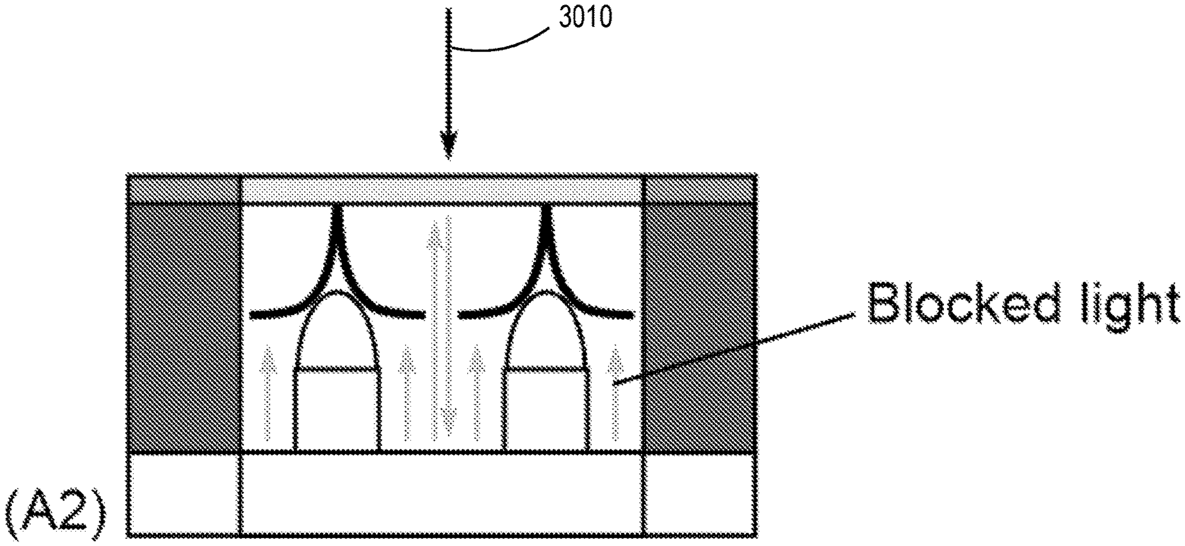
FIG. 30B is a side view schematic of the sensor in FIG. 30A under compressive loading.

FIGS. 30A-30B shows another example shear sensor with an additional compression sensing configuration 3000 operable to provide a shear displacement output signal under compressive loading. Similar to various disclosed examples described above, the sensor 3000 includes an optical source 3002, such as an LED, situated to emit a beam 3003 to an opposing surface 3004 displaying a color pattern. An optical detector 3004, such as a photodiode, is coupled to a base 3006 and arranged to detect a reflected beam 3005. For example, the base 3006 can be part of a sensor housing. As the color pattern translates relative to the optical source 3002 and optical detector 3004, e.g., due to shear flexure of an intervening elastomer layer 3008, reflectance characteristics of the reflected beam 3005 change, such as total reflected optical power, reflected wavelength-specific optical power, etc.

The sensor 3000 further includes a shade expander 3010 having a mechanical structure configured to block the beam 3003 emitted by the optical source and/or the reflected beam 3005, in response to a compressive force applied to the sensor 3000 along a compressive force direction 3010 (typically perpendicular to the translation direction associated with the detected shear forces). In some examples, the shade expander 3008 can include one or more extension members 3012*a*, 3012*b* extending from the base 3006 or opposing surface 3004. One or more opposing extension members 3014*a*, 3014*b* extend from other of the base 3006 or opposing surface 3004. The opposing extension members 3014*a*, 3014*b* (or also the extension member 3012*a*, 3012*b*) have ends 3016*a*, 3016*b* that are situated to contact the other respective extension members 3012*a*, 3012*b* under compressive load. For example, as the opposing surface 3004 and base 3006 experience compressive pressure, the extension members 3012*a*, 3014*a* can translate toward each other and extension members 3012*b*, 3014*b* can translate toward each other. The extension members 3012*a*, 3012*b* can be rigid in some examples. In further examples, extension members 3012*a*, 3012*b* can be shallow, flush with the base 3006, or extend inversely to form trenches.

As shown in FIG. 30B, as one or both of the extension member pairs 3012*a*, 3014*a* and 3012*b*, 3014*b* contact in the compressive force direction 3010. In some examples, the ends 3016*a*, 3016*b* can be elastic such that the ends 3016*a*, 3016*b* deform producing an extension in the shear direction with increasing force to form an increasing shade. In further examples, the ends 3016*a*, 3016 can be rigid, e.g., allowing the ends 3016*a*, 3016*b* out to produce shade such as through deformation or deflection away from the ends 3016*a*, 3016*b*. In further examples, an opposing end of the extension members 3014*a*, 3104*b* (e.g., at an attach point) or a middle portion can produce an extension in the shear direction. The increasing shade decreases an aperture size that blocks at least some of the emitted beam 3003 and/or reflected beam 3005. The resulting blockage of light changes the characteristics of the light that is detected with the photodiode 3004. The changed characteristics of a photodiode output signal, such as an attenuation of the total optical power or optical power at specific wavelengths, can be correlated to the compressive force applied to the sensor 3000. In some examples, the ends 3016*a*, 3016*b* can include respective sets of split ends 3018*a*, 3020*a* and 3018*b*, 3020*b* that extend in opposite directions in the shear direction under compressive load. In various examples, the ends 3016*a*, 3016*b* can compress to extend and produce shading in various ways in the shear direction, e.g., radially, biaxially, uniaxially, along only side uniaxially, symmetrically, asymmetrically, etc.

Figure 31A:
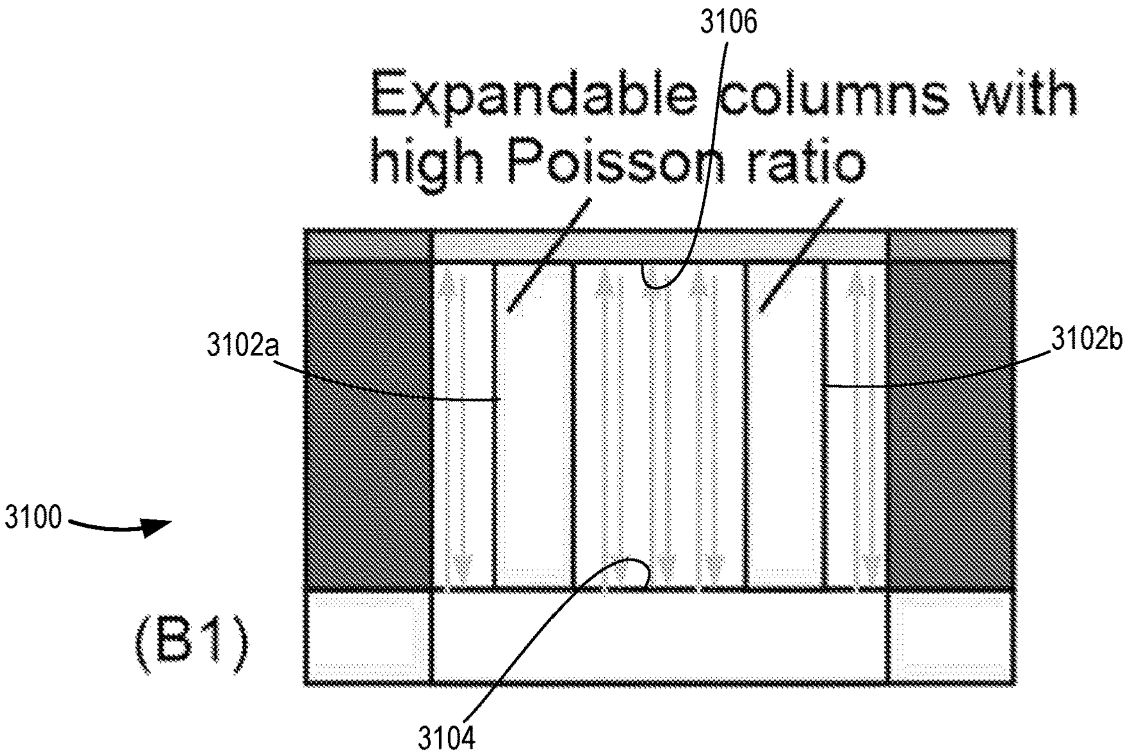
FIG. 31A is a side view schematic of an alternative sensor configured to measure compressive displacement or force with compressible columns that expand in a shear direction to produce shade
Figure 31B:
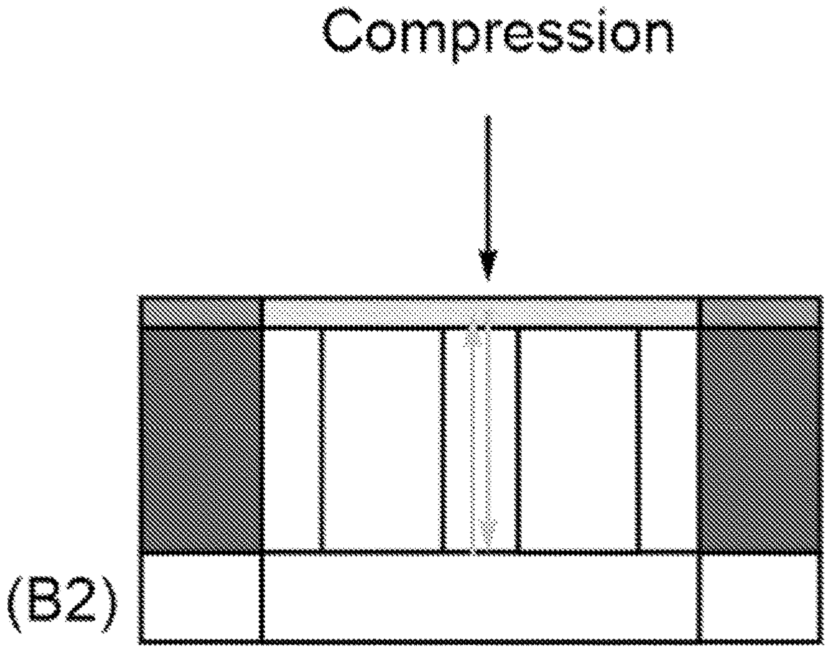
FIG. 31B is a side view schematic of the sensor in FIG. 31A under compressive loading.

FIGS. 31A-31B is example shear sensor 3100 that is operable to provide a shear displacement output signal under compressive loading which can be similar in many respects to the sensor 3000. The sensor 3100 includes one or more expandable columns 3102*a*, 3102*b* that extend from an emission surface 3104 to a reflective surface 3106. In response to a compressive force, the columns 3102*a*, 3102*b* expand laterally, e.g., in a direction of shear motion, to block or reduce light to be detected by a detection unit. In representative examples, the columns 3102*a*, 3102*b* have a high Poisson ratio, e.g., as provided by rubber, elastomer, or another suitable material.

In various examples, the compression sensing characteristics of the disclosed compression sensors can be used in conjunction with any of the shear sensors described herein. Through the signal attenuation caused by a suitable shade expander, compressive forces can be detected with an optical detector used to detect shear displacement. In some examples, compressive forces can reduce a shear sensing accuracy based on a change of light intensity. For example, green intensity will increase if green pattern area is visible to the optical detector through the window. However, the green intensity will also increase if the sensor is compressed such that the green pattern is closer to the light source and detector. Compression can also alter the mechanical behavior of the elastomeric medium shear layer. The compression sensing can then be used to calibrate the shear sensor to remove the effects of compression on the shear sensing signal to thereby improve the accuracy of the shear sensor. The compression data can also be used as an additional data stream to allow characterization of 3 axis forces. In further examples, the sensors can be configured to detect compression forces using the shade expander and without detecting shear displacement, e.g., as a dedicated compression sensor. Various reflectance patterns may be used in different examples, including patterns with a uniform reflectance (which may be particularly suited for compressive sensing without shear displacement sensing) and any of the patterns described herein.

General Considerations

As used in this application and in the claims, the singular forms "a," "an," and "the" include the plural forms unless the context clearly dictates otherwise. Additionally, the term "includes" means "comprises." Further, the term "coupled" does not exclude the presence of intermediate elements between the coupled items.

The systems, apparatus, and methods described herein should not be construed as limiting in any way. Instead, the present disclosure is directed toward all novel and non-obvious features and aspects of the various disclosed embodiments, alone and in various combinations and sub-combinations with one another. The disclosed systems, methods, and apparatus are not limited to any specific aspect or feature or combinations thereof, nor do the disclosed systems, methods, and apparatus require that any one or more specific advantages be present or problems be solved. Any theories of operation are to facilitate explanation, but the disclosed systems, methods, and apparatus are not limited to such theories of operation.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed systems, methods, and apparatus can be used in conjunction with other systems, methods, and apparatus. Additionally, the description sometimes uses terms like "produce" and "provide" to describe the disclosed methods. These terms are high-level abstractions of the actual operations that are performed. The actual operations that correspond to these terms will vary depending on the particular implementation and are readily discernible by one of ordinary skill in the art.

In some examples, values, procedures, or apparatus' are referred to as "lowest", "best", "minimum," or the like. It will be appreciated that such descriptions are intended to indicate that a selection among many used functional alternatives can be made, and such selections need not be better, smaller, or otherwise preferable to other selections.

As used herein, optical radiation or light beams refers to electromagnetic radiation at wavelengths of between about 100 nm and 10 μm, typically between about 200 nm and 2 μm, and more typically up to about 900 nm in color-based examples. Many disclosed examples use light emitting diodes, but other light sources can be suitable, including laser diodes, and other laser or light emission sources. In some examples, propagating optical radiation is referred to as one or more beams which can have diameters, shapes, cross-sectional areas, and beam divergences. Such beam parameters can depend on beam wavelength and the optical systems used for beam shaping, including lens arrangements, diffusers, or other optical components where suitable. For convenience, optical radiation is referred to as light in some examples and need not be at visible wavelengths. Reflectance generally refers to the ability of surfaces to reflect light differently and the proportion of light striking a surface which is reflected off the surface. The term "surface" is used in connection with relating optical components, and it will be appreciated surfaces can include various features, including edges, planes, threads, serrations, textures, chamfers, notches, detents, clamping members, etc., and such surfaces can be arranged in orientations other than parallel or perpendicular to different features of optical components where convenient.

There are several advantages to disclosed technology as compared to other shear sensors, including a) allowing differentiation of directional shear measurements, b) not requiring wire connections on both sides of the shearing bodies, c) since shear force is measured as the ratio of two resistances, calculated shear force can be independent of light intensity, thus the sensor can be misaligned up to 5 mm without impacting its performance, and d) relatively simple circuitry or electronic components can be used, making example sensors low-cost, robust, and easy to use.

Disclosed techniques may be, for example, embodied as software or firmware instructions carried out by a digital computer. For instance, any of the disclosed shear or displacement measurement techniques can be performed by a computer or other computing hardware (e.g., MCU, CPLD, ASIC, System-on-Chip, RISC, FPGA, etc.) that is part of a shear stress sensor or related measurement system. The shear sensor or measurement system can be programmed or configured to receive optical detector data associated with displacement of shearing bodies and perform the desired shear stress, strain, and/or displacement measurement computations (e.g., any of the measurement techniques disclosed herein). The computer can be a computer system comprising one or more processors (processing devices) and tangible, non-transitory computer-readable media (e.g., one or more optical media discs, volatile memory devices (such as DRAM or SRAM), or nonvolatile memory or storage devices (such as hard drives, NVRAM, and solid state drives (e.g., Flash drives)). The one or more processors can execute computer-executable instructions stored on one or more of the tangible, non-transitory computer-readable media, and thereby perform any of the disclosed techniques. For instance, software for performing any of the disclosed embodiments can be stored on the one or more volatile, non-transitory computer-readable media as computer-executable instructions, which when executed by the one or more processors, cause the one or more processors to perform any of the disclosed measurement techniques. The results of the computations can be stored (e.g., in a suitable data structure or lookup table) in the one or more tangible, non-transitory computer-readable storage media and/or can also be output to the user, for example, by communicating to a remote computing device, or by displaying, on a display device, shear stress, strain, and/or displacement values, changes, mappings, etc., with a graphical user interface.

In view of the many possible embodiments to which the principles of the disclosed technology may be applied, it should be recognized that the illustrated embodiments are only representative examples and should not be taken as limiting the scope of the disclosure. Alternatives specifically addressed in these sections are merely exemplary and do not constitute all possible alternatives to the embodiments described herein. For instance, various components of systems described herein may be combined in function and use. We therefore claim all that comes within the scope of the appended claims.

We claim:

1. A sensor, comprising:

an optical source situated in relation to a first surface and configured to emit a beam directed to an opposing surface having a spatially variable reflectance pattern; and an optical detector that comprises a single detection element situated in relation to the optical source to detect a portion of the beam reflected by the opposing surface and to produce an output signal that varies based on (i) a relative displacement between the reflectance pattern and the optical detector and (ii) a spatially variable reflectance resulting from the relative displacement, and that provides multi-axis displacement information along perpendicular shear axes.

2. The sensor of claim 1, further comprising an intermediate layer situated adjacent to the optical source and optical detector, wherein the layer is configured to deform to provide the displacement through a mechanical coupling with the opposing surface.

3. The sensor of claim 2, wherein the intermediate layer includes one or more windows situated to receive and transmit the beam and the reflected portion through the one or more windows.

4. The sensor of claim 2, wherein the intermediate layer comprises an elastomer transducer layer.

5. The sensor of claim 4, wherein the elastomer transducer layer comprises a thickness and curing characteristics configured to define a shear modulus.

6. The sensor of claim 2, further comprising a sensor housing configured to support the optical source, optical detector, and/or intermediate layer in fixed relation to each other.

7. The sensor of claim 6, further comprising a base plate attached to the sensor housing, and/or intermediate layer, wherein the base plate comprises the opposing surface.

8. The sensor of claim 6, wherein the optical detector comprises an aperture mask configured to define the amount of the detected portion by controlling the amount of area of the opposing surface viewed by the optical detector.

9. The sensor of claim 8, wherein the spatially variable reflectance pattern comprises a repeating reflectance pattern and the aperture mask comprises a repeating aperture mask pattern associated with the repeating reflectance pattern.

10. The sensor of claim 9, wherein respective repetition periods of the repeating reflectance pattern and repeating reflectance pattern are configured to provide a tolerance for recalibrating the sensor after a slip displacement between the optical detector and the opposing surface.

11. The sensor of claim 1, wherein the spatially variable reflectance pattern comprises a spatially variable color reflectance pattern configured to reflect light by different amounts according to the spatially variable color.

12. The sensor of claim 11, wherein the spatially variable color reflectance pattern comprises a first pattern area having a first color profile, a pair of second pattern areas having a common second color profile and situated on opposing sides of the first pattern area along a first shear axis, and a pair of third pattern areas having a common third color profile and situated on opposing sides of the first pattern area along a second shear axis perpendicular to the first shear axis.

13. The sensor of claim 12, wherein the spatially variable color reflectance pattern further comprises four fourth pattern area having a fourth color profile having a reflectance common with the second and third color profiles, wherein the four fourth pattern areas are situated in a corner relationship to the first pattern area and the second and third opposing pattern areas.

14. The sensor of claim 12, wherein the optical source comprises a red, green, blue (RGB) light emitting diode (LED).

15. The sensor of claim 14, wherein the first color profile is a green color configured to reflect the green light of the RGB LED, the second color profile is one of blue or red color configured to reflect the corresponding blue or red light of the RGB LED, and the third color profile is other one of the blue or red color configured to reflect the corresponding blue or red light of the RGB LED, wherein the fourth color profile is a magenta color configured to reflect both the blue and the red light of the RGB LED.

16. The sensor of claim 1, further comprising a processor and memory configured with processor-executable instructions that cause the processor to:

vary the spectral content of the beam produced by the optical source over time, receive the output signal from the optical detector and associate different output signal times with the timing of the variable spectral content, and determine a reflectance change associated with the relative displacement.

17. The sensor of claim 16, wherein the memory is configured with processor-executable instructions that cause the processor to measure, based on the reflectance change, a shear stress and/or displacement between (i) the opposing surface and the (ii) optical source and optical detector.

18. The sensor of claim 1, wherein the spatially variable reflectance pattern comprises a spatially variable gray scale reflectance pattern configured to reflect light by different amounts according to an intensity dependent gray scale spatial variation.

19. The sensor of claim 1, wherein the optical source comprises a white light source.

20. The sensor of claim 1, wherein the optical detector comprises one or more optical filters configured to attenuate light outside of a selected wavelength or wavelength range.

21. The sensor of claim 20, wherein the one or more optical filters comprise a plurality of bandpass filters configured to attenuate different wavelengths or wavelength ranges of a spectrum of light of the beam reflected by the opposing surface.

22. The sensor of claim 20, further comprising a processor and memory configured with processor-executable instructions that cause the processor to:

receive the output signal from the optical detector, wherein the optical detector is configured to detect a variation of spectral content of the reflected beam based on the optical filters, and determine a reflectance change associated with the relative displacement and the detected variation of spectral content.

23. The sensor of claim 22, wherein the memory is configured with processor-executable instructions that cause the processor to measure, based on the reflectance change, a shear stress and/or displacement between (i) the opposing surface and the (ii) optical source and optical detector.

24. The sensor of claim 1, wherein the optical detector comprises a transducer configured to provide an output signal comprising a variable electrical quantity.

25. The sensor of claim 1, wherein the opposing surface comprises an integral or attached part of an object.

26. The sensor of claim 1, wherein the opposing surface comprises an adhesive layer arranged on one or both of a side presenting the opposing surface and a side opposite the side presenting the opposing surface.

27. The sensor of claim 26, wherein the adhesive layer is configured to adhere to a sensor housing or an elastomer transducer layer arranged between the sensor housing and the opposing surface;

wherein the adhesive layer is configured to adhere the side opposite the side presenting the opposing surface, to a shearing surface.

28. The sensor of claim 1, wherein the opposing surface comprises a randomized pixel pattern.

29. The sensor of claim 28, wherein the randomized pixel pattern is configured to provide a variation in the output signal through the relative displacement, wherein the variation is configured to provide a discrimination between a positive and negative directionality based on the randomized pixel pattern and a data classifier.

30. A prosthesis, comprising the sensor of claim 1.

31. The prosthesis of claim 30, wherein the opposing surface is arranged on a residual limb, and wherein the prosthesis comprises a prosthetic socket and the sensor housing is embedded within the socket.

32. A shoe comprising the sensor of claim 1, wherein the opposing surface is arranged at an insole of the shoe such that it is facing down towards a midsole, and wherein the sensor housing is embedded within a midsole of the shoe.

33. A method, comprising:

emitting a beam from an optical source and directing the beam to an opposing surface having a spatially variable reflectance pattern; and with a single detection element of an optical detector situated in relation to the optical source, detecting a portion of the beam reflected by the opposing surface and producing an output signal that varies based on (i) a relative displacement between the reflectance pattern and the optical detector and (ii) a spatially variable reflectance resulting from the relative displacement and that provides multi-axis displacement information along perpendicular shear axes.

* * * * *